(12) United States Patent
Ambrose et al.

(10) Patent No.: US 7,638,327 B2
(45) Date of Patent: Dec. 29, 2009

(54) BAFF RECEPTOR ANTIBODIES AND METHODS

(75) Inventors: Christine M. Ambrose, Reading, MA (US); Jeffrey S. Thompson, Stoneham, MA (US)

(73) Assignee: Biogen IDEC MA Inc., Cambridge, MA (US)

( * ) Notice: Subject to any disclaimer, the term of this patent is extended or adjusted under 35 U.S.C. 154(b) by 323 days.

(21) Appl. No.: 11/426,236

(22) Filed: Jun. 23, 2006

(65) Prior Publication Data

US 2006/0240517 A1    Oct. 26, 2006

Related U.S. Application Data

(62) Division of application No. 10/380,703, filed as application No. PCT/US01/28006 on Sep. 6, 2001, now Pat. No. 7,112,421.

(60) Provisional application No. 60/312,185, filed on Aug. 14, 2001, provisional application No. 60/268,499, filed on Feb. 13, 2001, provisional application No. 60/234,140, filed on Sep. 21, 2000, provisional application No. 60/233,152, filed on Sep. 18, 2000.

(51) Int. Cl.
| | |
|---|---|
| A61K 39/395 | (2006.01) |
| C12N 5/12 | (2006.01) |
| C07K 16/28 | (2006.01) |
| G01N 33/563 | (2006.01) |
| G01N 33/567 | (2006.01) |
| G01N 33/577 | (2006.01) |

(52) U.S. Cl. .................. 435/334; 435/344; 435/7.2; 435/7.21; 435/7.23; 435/7.24; 424/133.1; 424/138.1; 424/139.1; 424/143.1; 424/135.1; 530/387.3; 530/387.7; 530/388.22; 530/388.8; 530/389.7

(58) Field of Classification Search ................ None
See application file for complete search history.

(56) References Cited

U.S. PATENT DOCUMENTS

| | | | |
|---|---|---|---|
| 5,969,102 | A | 10/1999 | Bram et al. |
| 6,297,367 | B1 | 10/2001 | Tribouley |
| 6,316,222 | B1 | 11/2001 | Bram et al. |
| 6,403,770 | B1 | 6/2002 | Yu et al. |
| 6,475,986 | B1 | 11/2002 | Aggarwal |
| 6,475,987 | B1 | 11/2002 | Shu |
| 6,541,224 | B2 | 4/2003 | Yu et al. |
| 6,551,795 | B1 | 4/2003 | Rubenfield et al. |
| 6,869,605 | B2 | 3/2005 | Browning et al. |
| 6,875,846 | B2 | 4/2005 | Rennert et al. |
| 7,083,785 | B2 | 8/2006 | Browning et al. |
| 2002/0172674 | A1 | 11/2002 | Jeffrey et al. |
| 2003/0082175 | A1 | 5/2003 | Schneider et al. |
| 2003/0092164 | A1 | 5/2003 | Gross et al. |
| 2003/0095967 | A1 | 5/2003 | MacKay et al. |
| 2003/0194743 | A1 | 10/2003 | Beltzer et al. |
| 2006/0240518 | A1 | 10/2006 | Ambrose et al. |
| 2006/0240519 | A1 | 10/2006 | Ambrose et al. |
| 2006/0240520 | A1 | 10/2006 | Ambrose et al. |

FOREIGN PATENT DOCUMENTS

| | | |
|---|---|---|
| EP | 0 869 180 A1 | 10/1998 |
| WO | WO 97/33902 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | WO 99/11791 | 3/1999 |
| WO | WO 99/12964 | 3/1999 |
| WO | WO 99/12965 | 3/1999 |
| WO | WO 99/33980 | 7/1999 |
| WO | WO 00/26244 | 5/2000 |
| WO | WO 00/39295 | 7/2000 |
| WO | WO 00/40716 | 7/2000 |
| WO | WO 00/43032 | 7/2000 |
| WO | WO 00/50597 | 8/2000 |
| WO | WO 00/50633 | 8/2000 |
| WO | WO 00/58362 | 10/2000 |
| WO | WO 01/12812 A2 | 2/2001 |
| WO | WO 01/24811 | 4/2001 |
| WO | WO 02/02641 | 1/2002 |
| WO | WO 02/18620 | 3/2002 |
| WO | WO 02/38766 | 5/2002 |
| WO | WO 02/092620 | 11/2002 |
| WO | WO 03/014294 | 2/2003 |
| WO | WO 03/024991 | 3/2003 |
| WO | WO 03/035846 | 5/2003 |
| WO | WO 03/055979 | 7/2003 |
| WO | WO 2004/035735 | 4/2004 |
| WO | WO 2005/005462 | 1/2005 |

OTHER PUBLICATIONS

Lin et al., Anti-BR3 antibodies: a new class of B-cell immunotherapy combining cellular depletion and survival blockade, Blood 110(12): 3959-3967, Dec. 2007.*

(Continued)

*Primary Examiner*—Lorraine Spector
*Assistant Examiner*—Claire Kaufman
(74) *Attorney, Agent, or Firm*—Finnegan, Henderson, Farabow, Garrett & Dunner, L.L.P

(57) ABSTRACT

Disclosed are nucleic acids encoding BAFF-R polypeptides, as well as antibodies to BAFF-R polypeptides and pharmaceutical compositions including the same. Methods of treating tumorigenic and autoimmune conditions using the nucleic acids, polypeptides, antibodies and pharmaceutical compositions of this invention are also provided.

44 Claims, 28 Drawing Sheets

OTHER PUBLICATIONS

Vugmeyster et al., A soluble BAFF antagonist, BR3-Fc, decreased peripheral blood B cells and lymphoid tissu marginal zone and follicular B cells in cynomolgus monkeys, Am. J. Path. 168(2):476-489, Feb. 2006.*

Database Accession No. AI250289, XP002206618.^ GenBank.

Database Accession No. Z99716.4, XP002206619.^ GenBank.

Do et al., Attenuation of Apoptosis Underlies B Lymphocyte Stimulator Enhancement of Humoral Immune Response. (2000). J. Exp. Med., 192(7):953-964.

Domingues, H.M., Rational Design Strategies to Improve Cytokine Foldability and Minimization of a Functional Motif: The IL-4 Case. (1999). Thesis University of Utrecht, p. 48, line 25-p. 51, line 6, p. 94; table III.

Executed Declaration of Jurg Tschopp, dated Dec. 18, 2003.

Executed Declaration of Pascal Schneider, dated Dec. 18, 2003.

GenBank Accession No. AK008142, Published Feb. 16, 2001.

Gordon et al., BAFF/Blys Receptor 3 Comprises a Minimal TNF Receptor-Like Module that Encodes a Highly Focused Ligand-Binding Site. (2003). Biochemistry, 42:5977-5983.

Gras et al., BCMAp: an integral membrane protein in the Golgi apparatus of human mature B lymphocytes. (1995). Intl. Immunol., 7(7):1093-1106.

Gross et al., TACI and BCMA are receptors for a TNF homologue implicated in B-cell autoimmune disease. (2000). Nature, 404:995-999.

Hahne et al., April, a New Ligand of the Tumor Necrosis Factor Family, Stimulates Tumor Cell Growth. (1998). J. Exp. Med., 188(6):1185-1190.

International Search Report for International Application No. PCT/US01/28006, mailed Mar. 28, 2003.

Kashii et al., Constitutive Expression and Role of the TNF Family Ligands in Apoptotic Killing of Tumor Cells by Human NK Cells. (1999). J. Immunol., 163:5358-66.

Kayagaki et al., BAFF/BlyS Receptor 3 Binds the B Cell Survival Factor BAFF Ligand through a Discrete Surface Loop and Promotes Processing of NF-$\kappa$B2. (2002). Immunity., vol. 10, 17(4):515-524.

Khare et al., The role of TALL-1 and April in immune regulations. (2001). Trends Immunol. 22(2): 61-63.

Khare et al., Severe B cell hyperplasia and autoimmune disease in TALL-1 transgenic mice. (2000). Proceedings of the Natl. Acad. of Sci. USA, 97(7):3370-3375.

Kwon et al., Single Amino Acid Substitutions of $a_1$—Antitrypsin That Confer Enhancement in Thermal Stability. (1994). J. Biol. Chem., 269:9627-9631.

Laabi et al., A new gene, BCM, on chromosome 16 is fused to the interleukin 2 gene by a t(4;16)(q26,p13) translocation in a malignant T cell lymphoma. (1992). EMBO J., 11:3897-3904.

Laabi et al., The BCMA gene, preferentially expressed during B lymphoid maturation, 13 bidirectionally transcribed. (1994). Nucleic Acids Res., 22(7):1147-1154.

Mackay et al., Mice Transgenic for BAFF Develop Lymphocytic Disorders Along with Autoimmune Manifestations. (1999). J. Exp. Med., 190(11):1697-1710.

Madry et al., The characterization of murine BCMA gene defines it as a new member of the tumor necrosis factor receptor superfamily. (1998). Intl. Immunol., 10(11):1693-1702.

Marsters et al., Interaction of the TNF Homologues BLyS and April with the TNF Receptor Homologues BCMA and TACI. (2000). Curr. Biol., 10:785-788.

Moore et al., BLyS: Member of the Tumor Necrosis Factor Family and B Lymphocyte Stimulator. (1999). Science, 282:260-263.

Mukhopadhyay et al., Identification and Characterization of a Novel Cytokine, Thank, a TNF Homologue That Activates Apoptosis, Nuclear Factor-$\kappa$B, and c-Jun $NH_2$-Terminal Kinase. (1999). J. Biol. Chem., 274:15978-15981.

Partial International Search Report for International Application No. PCT/US01/28006, mailed Sep. 6, 2002.

Riken Genome Exploration Research Group Phase II Team and Fantom Consortium. Functional annotation of a full-length mouse cDNA collection. (2001). Nature, 685-690, vol. 409.

Excerpt from Supplementary Table 1 to: Riken Genome Exploration Research Group Phase II Team and Fantom Consortium. Functional annotation of a full-length mouse cDNA collection. (2001). Nature, 685-690, vol. 409.

Schein C.H., Production of Soluble Recombinant Proteins in Bacteria. (1989). Biotechnology, 7:1141-1149.

Schiemann et al., An Essential Role for BAFF in the Normal Development of B Cells Through a BCMA-Independent Pathway. (2001). Science, 293:2111-2114.

Schneider et al., BAFF, a Novel Ligand of the Tumor Necrosis Factor Family, Stimulates B Cell Growth. (1999). J. Exp. Med., 189:1747-1756.

Shu et al., TALL-1 is a novel member of the TNF family that is down-regulated by mitogens, (1999). Leukocyte Biol. 65:680-683.

Thompson et al., BAFF Binds to the Tumor Necrosis Factor Receptor-like Molecule B Cell Maturation Antigen and is Important for Maintaining the Peripheral B Cell Population. (2000). J. Exp. Med., 192:129-135.

Thompson et al., BAFF-R, A Newly Identified TNF Receptor That Specifically Interacts with BAFF. (2001). Science, 293:2108-211.

Von Bülow et al., NT-AT Activation Induced by a CAML-Interacting Member of the Tumor Necrosis Factor Receptor Superfamily. (1997). Science, 278:138-141.

Waldschmidt et al., Long Live the Mature B-Cell—A Baffling Mystery Resolved. (2001). Science, 293:2012-2013.

Ward et al., Blocking of adhesion molecules in vivo as anti-inflammatory therapy. (1994). Ther. Immunol. 1:165-71.

Ware C.F., April and BAFF Connect Autoimmunity and Cancer. (2000). J. Exp. Med., 192(11):F35-37.

Wood et al., Prolines and Amyloidogenicity in Fragments of the Alzheimer's Peptide β/A4. (1995). Biochemistry, 34:724-730.

Wu et al., Tumor Necrosis Factor (TNF) Receptor Superfamily Member TACI is a Hight Affinity Receptor of TNF Family Members April and BlyS. (2000). J. Biol. Chem. 275(45):35478-35485.

Yan et al., Identification of a Novel Receptor for B Lymphocyte Stimulator that is Mutated in a Mouse Strain with Severe B Cell Deficiency. (2001). Curr. Biol., 11:1547-1552.

Yu et al., April and TALL-1 and receptors BCMA and TACI: system for regulating humoral immunity. (2000). Nat. Immun., 1:252-256.

* cited by examiner

Figure 1A
Sequence of the JST576 cDNA clone

```
   1  GCACCATGAG GCGAGGGCCC CGGAGCCTGC GGGGCAGGGA CGCGCCAGCC
  51  CCCACGCCCT GCGTCCCGGC CGAGTGCTTC GACCTGCTGG TCCGCCACTG
 101  CGTGGCCTGC GGGCTCCTGC GCACGCCGCG GCCGAAACCG GGTAAGGGGG
 151  ACCCACGGGG CGCGCGGCGC CGGCAGCTGC GGGGAGAACG GGCCCCGAT
 201  CGCCAGGGCG CAGGCAGAGC CCGACCCCC GGGGGCGCCG AGGGCTGAAA
 251  GGACCCTGTG GGCAGGGCCT GGAGGGGCCC GCGATCACCG CGTGGCCCTC
 301  ACCGCCGCCT CTCTCCCTCC CCTTGTCCAC CGCCCCCGG CTGTCCCTCC
 351  CCTCCCCGGC CAGCCTCGCC CCCCTCCGCC CCTCCCCGTC CCCGCTCCTC
 401  CCTCCCCTCG GCCCCCTGGC CTCCCTCCCT GTCCCCTCCC GAAGCAGCCG
 451  GGGCCAGCAG CCCTGCGCCC AGGACGGCGC TGCAGCCGCA GGAGTCGGTG
 501  GGCGCGGGGG CCGGCGAGGC GGCGCTGCCC CTGCCCGGGC TGCTCTTTGG
 551  CGCCCCCGCG CTGCTGGGCC TGGCACTGGT CCTGGCGCTG GTCCTGGTGG
 601  GTCTGGTGAG CTGGAGGCGG CGACAGCGGC GGCTTCGCGG CGCGTCCTCC
 651  GCAGAGGCCC CCGACGGAGA CAAGGACGCC CCAGAGCCCC TGGACAAGGT
 701  CATCATTCTG TCTCCGGGAA TCTCTGATGC CACAGCTCCT GCCTGGCCTC
 751  CTCCTGGGGA AGACCCAGGA ACCACCCCAC CTGGCCACAG TGTCCCTGTG
 801  CCAGCCACAG AGCTGGGCTC CACTGAACTG GTGACCACCA AGACGGCCGG
 851  CCCTGAGCAA CAATAGCAGG GAGCCGGCAG GAGGTGGCCC CTGCCCTCCC
 901  TCTGGACCCC CAGCCAGGGG CTTGGAAATC AAATTCAGCT CTTCACTCCA
 951  GCATGCACAT GCCCTCTTTC TGGGACCAGG CTAACCCTGC AGAAGCACAG
1001  ACACTACAGA CCACAGCATT CAGCCCCAT GGAGTTTGGT GTGCTTGCCT
1051  TTGGCTTCAG ACCTCACCAT CTTTGACAGC CCTTGAAGGT GGTAGCCCAG
1101  CTCCTGTTCC TGTGCCTTCA AAAGGCTGGG GCACTATGAG TAAAAGACCG
1151  CTTTTAAAAT GGGGAAGGCA CCATTAAGCC AAAATGAATC TGAAAAAAGA
1201  C
```

Figure 1B
Sequence of EST AI250289

```
  1  GTCGACCCAC GCGTCCGCCC ACGCGTCCGG TGCGGCGGCG TCGGCACCAT
 51  GAGGCGAGGG CCCCGGAGCC TGCGGGGCAG GGACGCGCCA GCCCCACGC
101  CCTGCGTCCC GGCCGAGTGC TTCGACCTGC TGGTCCGCCA CTGCGTGGCC
151  TGCGGGCTCC TGCGCACGCC GCGGCCGAAA CCGGGTAAGG GGGACCCACG
201  GGGCGCGCGG CGCCGGCAGC TGCGGGGAGA ACGGGCCCC GATCGCCAGG
251  GCGCAGGCAG AGCCCCGACC CCCGGGGGCG CCGAGGGCTG AAAGGACCCT
301  GTGGGCAGGG CCTGGAGGGG CCCGCGATCA CCGCGTGGCC CTCACCGCCG
351  CCTCTCTCCC TCCCCTTGTC CACCGCCCCC CGGCTGTCCC TCCCCTCCCC
401  GGCCAGCCTC GCCCCCCTCC GCCCCTCCCC GTCCCCGCTC CTCCCTCCCC
451  TCGGCCCCCT GGCCTCCCTC CCTGTCCCCT CCCGAAGCAG CCGGGGCCAG
501  CAGCCCTGCG CCCAGGACGG CGCTGCAGCC GCAGGAGTCG GTGGGCGCGG
551  GGGCCGGCGA GGCGGCGCTG CCCCTGCCCG GCTGCTCTT TGGCGCCCC
601  GCGCTGCTGG GCCTGGCACT GGTCCTGGCG CTGGTCCTGG TGGGTCTGGT
651  GAGCTGGAGG CGGCGACAGC GGCGGCTTCG CGGCGCGTCC TCCGCAGAGG
701  CCCCCGACGG AGACAAGGAC GCCCCAGAGC CCCTGGACAA GGTCATCATT
751  CTGTCTCCGG GAATCTCTGA TGCCACAGCT CCTGCCTGGC CTCCTCCTGG
801  GGAAGACCCA GGAACCACCC CACCTGGCCA CAGTGTCCCT GTGCCAGCCA
851  CAGAGCTGGG CTCCACTGAA CTGGTGACCA CCAAGACGGC CGGCCCTGAG
901  CAACAATAGC AGGGAGCCGG CAGGAGGTGG CCCCTGCCCT CCCTCTGGAC
951  CCCCAGCCAG GGGCTTGGAA ATCAAATTCA GCTCTTCACT CC
```

Figure 2A

Sequence of JST576 Predicted by GENSCAN

```
  1  GGCGCGCCGC ACCATGAGGC GAGGGCCCCG GAGCCTGCGG GGCAGGGACG
 51  CGCCAGCCCC CACGCCCTGC GTCCGGCCG  AGTGCTTCGA CCTGCTGGTC
101  CGCCACTGCG TGGCCTGCGG GCTCCTGCGC ACGCCGCGGC CGAAACCGGC
151  AGCCGGGGCC AGCAGCCCTG CGCCCAGGAC GGCGCTGCAG CCGCAGGAGT
201  CGGTGGGCGC GGGGGCCGGC GAGGCGGCGC TGCCCCTGCC CGGGCTGCTC
251  TTTGGCGCCC CCGCGCTGCT GGGCCTGGCA CTGGTCCTGG CGCTGGTCCT
301  GGTGGGTCTG GTGAGCTGGA GGCGGCGACA GCGGCGGCTT CGCGGCGCGT
351  CCTCCGCAGA GGCCCCCGAC GGAGACAAGG ACGCCCCAGA GCCCCTGGAC
401  AAGGTCATCA TTCTGTCTCC GGGAATCTCT GATGCCACAG CTCCTGCCTG
451  GCCTCCTCCT GGGGAAGACC CAGGAACCAC CCCACCTGGC CACAGTGTCC
501  CTGTGCCAGC CACAGAGCTG GGCTCCACTG AACTGGTGAC CACCAAGACG
551  GCCGGCCCTG AGCAACAATA GCAGGGAGCC GGCAGGAGGT GGCCCCTGCC
601  CTCCCTCTGG ACCCCCAGCC AGGGGCTTGG AAATCAAATT CAGCTCTTCA
651  CTCCAGCATG CACATGCCCT CTTTCTGGGA CCAGGCTAAC CCTGCAGAAG
701  CACAGACACT ACAGACCACA GCATTCAGCC CCATGGAGT  TTGGTGTGCT
751  TGCCTTTGGC TTCAGACCTC ACCATCTTTG ACAGCCCTTG AAGGTGGTAG
801  CCCAGCTCCT GTTCCTGTGC CTTCAAAAGG CTGGGGCACT ATGAGTAAAA
851  GACCGCTTTT AAAATGGGGA AGGCACCATT AAGCCAAAAT GAATCTGAAA
901  AAAGAC
```

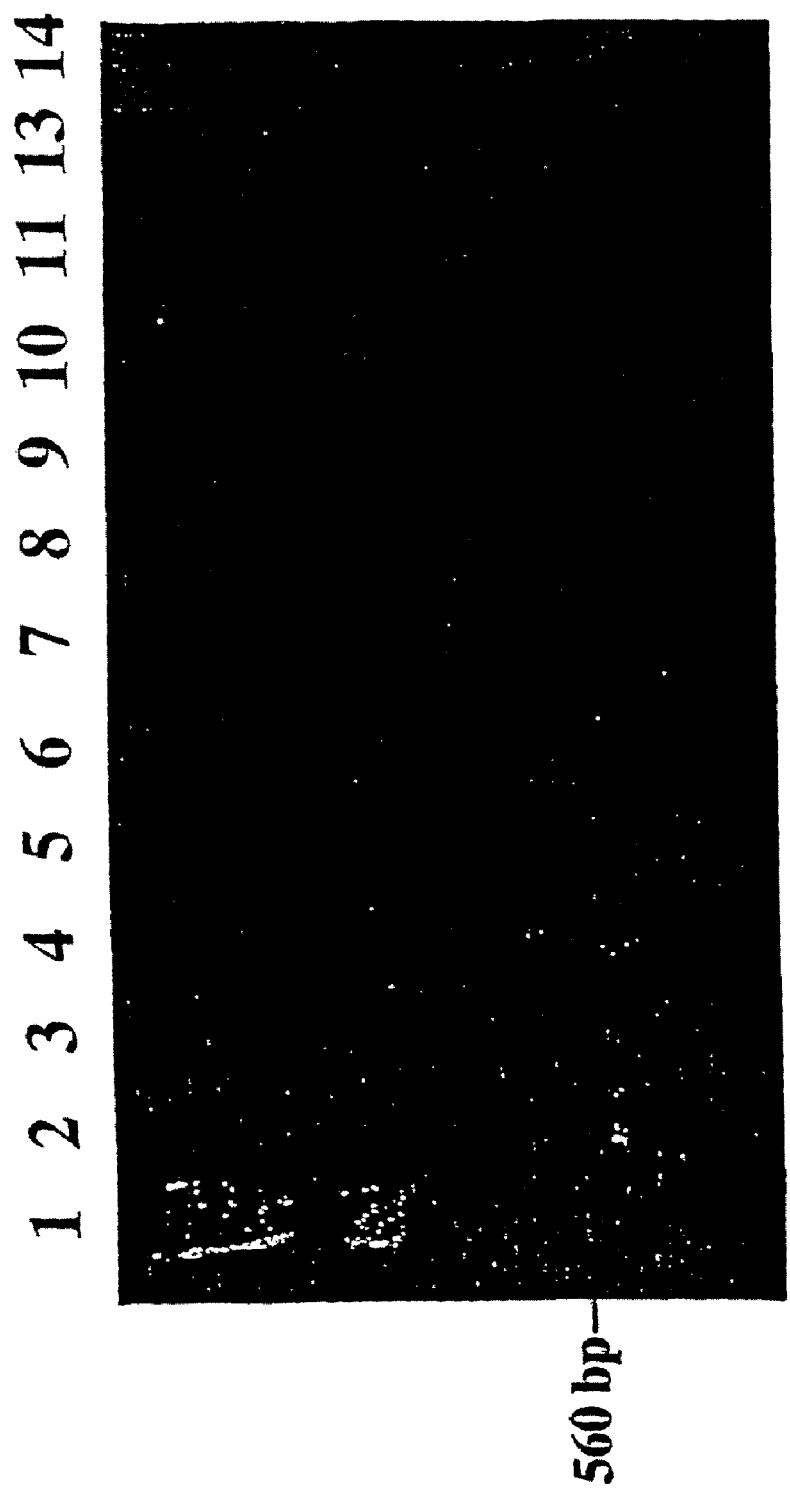

Figure 2C

JST576 Sequence without the Intron

```
  1  GGCGCGCCGC ACCATGAGGC GAGGGCCCCG GAGCCTGCGG GGCAGGGACG
 51  CGCCAGCCCC CACGCCCTGC GTCCGGCCG  AGTGCTTCGA CCTGCTGGTC
101  CGCCACTGCG TGGCCTGCGG GCTCCTGCGC ACGCCGCGGC CGAAACCGGC
151  CGGGGCCAGC AGCCCTGCGC CCAGGACGGC GCTGCAGCCG CAGGAGTCGG
201  TGGGCGCGGG GGCCGGCGAG GCGGCGCTGC CCTGCCCGG  GCTGCTCTTT
251  GGCGCCCCG  CGCTGCTGGG CCTGGCACTG GTCCTGGCGC TGGTCCTGGT
301  GGGTCTGGTG AGCTGGAGGC GGCGACAGCG GCGGCTTCGC GGCGCGTCCT
351  CCGCAGAGGC CCCCGACGGA GACAAGGACG CCCCAGAGCC CCTGGACAAG
401  GTCATCATTC TGTCTCCGGG AATCTCTGAT GCCACAGCTC CTGCCTGGCC
451  TCCTCCTGGG GAAGACCCAG GAACCACCCC ACCTGGCCAC AGTGTCCCTG
501  TGCCAGCCAC AGAGCTGGGC TCCACTGAAC TGGTGACCAC CAAGACGGCC
551  GGCCCTGAGC AACAATAGCA GGGAGCCGGC AGGAGGTGGC CCCTGCCCTC
601  CCTCTGGACC CCCAGCCAGG GGCTTGGAAA TCAAATTCAG CTCTTCACTC
651  CAGCATGCAC ATGCCCTCTT TCTGGGACCA GGCTAACCCT GCAGAAGCAC
701  AGACACTACA GACCACAGCA TTCAGCCCCC ATGGAGTTTG GTGTGCTTGC
751  CTTTGGCTTC AGACCTCACC ATCTTTGACA GCCCTTGAAG GTGGTAGCCC
801  AGCTCCTGTT CCTGTGCCTT CAAAAGGCTG GGGCACTATG AGTAAAAGAC
851  CGCTTTTAAA ATGGGGAAGG CACCATTAAG CCAAAATGAA TCTGAAAAAA
901  GAC
```

FIGURE 2D

Human BAFF-R Amino Acid Sequence

```
GGGCGCCTAC AATCTCAGCT ACTCGGGAGG CTGAGGCAGA GAATTGTTTG AACCCGGGAG
                                                    *    T  R  E

GCAGAGCTTG CAGTGAGCCG AGATAGCGCC ATTGCACTCC AGCCTGGGCG ACAGAGCGAG
 A  E  L    A  V  S  R   D  S  A   I  A  L   Q  P  G  R   Q  S  E

ACTCCGTCTC AAAAAAAAAA AAAGAAAAGA AAGGGGGGCC CCAGGCGAGC TCGGTCCCAC
 T  P  S    Q  K  K  K   K  K  R   K  G  G    P  R  R  A   R  S  H

CCAGCAGGCG GGGGCGGGGC AGGGCAGAGT GCTCCCCCCG CCCCCGCTT CCTCCCCGAG
 P  A  G    G  G  A    G  Q  S    A  P  P    P  P  R  F   L  P  E

GGCCCCGGAG CCCAGCTCAG CCTCAGTCCC CGCAGCTTGT GCGGCGGCGT CGGCACCATG
 G  P  G    A  Q  L  S   L  S  P   R  S  L    C  G  G  V   G  T  M

AGGCGAGGGC CCCGGAGCCT GCGGGGCAGG GACGCGCCAG CCCCCACGCC CTGCGTCCCG
 R  R  G    P  R  S  L   R  G  R   D  A  P    A  P  T  C   V  P

GCCGAGTGCT TCGACCTGCT GGTCCGCCAC TGCGTGGCCT GCGGGCTCCT GCGCACGCCG
 A  E  C    F  D  L  L   V  R  H   C  V  A    C  G  L  L   R  T  P

CGGCCGAAAC CGGCCGGGGC CAGCAGCCCT GCGCCCAGGA CGGCGCTGCA GCCGCAGGAG
 R  P  K    P  A  G  A   S  S  P   A  P  R    T  A  L  Q   P  Q  E

TCGGTGGGCG CGGGGGCCGG CGAGGCGGCG CTGCCCCTGC CCGGGCTGCT CTTTGGCGCC
 S  V  G    A  G  A  G   E  A  A   L  P  L    P  G  L  L   F  G  A

CCCGCGCTGC TGGGCCTGGC ACTGGTCCTG GCGCTGGTCC TGGTGGGTCT GGTGAGCTGG
 P  A  L    L  G  L  A   L  V  L   A  L  V    L  V  G  L   V  S  W

AGGCGGCGAC AGCGGCGGCT TCGCGGCGCG TCCTCCGCAG AGGCCCCCGA CGGAGACAAG
 R  R  R    Q  R  R  L   R  G  A   S  S  A    E  A  P  D   G  D  K

GACGCCCCAG AGCCCCTGGA CAAGGTCATC ATTCTGTCTC CGGGAATCTC TGATGCCACA
 D  A  P    E  P  L  D   K  V  I   I  L  S    P  G  I  S   D  A  T

GCTCCTGCCT GGCCTCCTCC TGGGGAAGAC CCAGGAACCA CCCCACCTGG CCACAGTGTC
 A  P  A    W  P  P  P   G  E  D   P  G  T    T  P  P  G   H  S  V

CCTGTGCCAG CCACAGAGCT GGGCTCCACT GAACTGGTGA CCACCAAGAC GGCCGGCCCT
 P  V  P    A  T  E  L   G  S  T   E  L  V    T  T  K  T   A  G  P

GAGCAACAAT AGCAGGGAGC CGGCAGGAGG TGGCCCCTGC CCTCCCTCTG GACCCCAGC
 E  Q  Q    *

CAGGGGCTTG GAAATCAAAT TCAGCTCTTC ACTCCAGCAT GCACATGCCC TCTTTCTGGG
ACCAGGCTAA CCCTGCAGAA GCACAGACAC TACAGACCAC AGCATTCAGC CCCCATGGAG
TTTGGTGTGC TTGCCTTTGG CTTCAGACCT CACCATCTTT GACAGCCCTT GAAGGTGGTA
GCCCAGCTCC TGTTCCTGTG CCTTCAAAAG GCTGGGGCAC TATGAGTAAA AGACCGCTTT
TAAAATGGGG AAGGCACCAT TAAGCCAAAA TGAATCTGAA AAAAGAC
```

Figure 4A

Murine BAFF-R Sequence

```
   1  GAATTCGGCA CGAGCCCAGA CTCGGAACTG TCCCAGCTGC ATGAGGCGGC
  51  GACATGGGCG CCAGGAGACT CCGGGTCCGA AGCCAGAGGA GCCGGGACAG
 101  CTCGGTGCCC ACCCAGTGCA ATCAGACCGA GTGCTTCGAC CCTCTGGTGA
 151  GAAACTGCGT GTCCTGTGAG CTCTTCCACA CGCCGGACAC TGGACATACA
 201  AGCAGCCTGG AGCCTGGGAC AGCTCTGCAG CCTCAGGAGG GCTCCGCGCT
 251  GAGACCCGAC GTGGCGCTGC TCGTCGGTGC CCCCGCACTC CTGGGACTGA
 301  TACTGGCGCT GACCCTGGTG GGTCTAGTGA GTCTGGTGAG CTGGAGGTGG
 351  CGTCAACAGC TCAGGACGGC CTCCCCAGAC ACTTCAGAAG GAGTCCAGCA
 401  AGAGTCCCTG GAAAATGTCT TTGTACCCTC CTCAGAAACC CCTCATGCCT
 451  CAGCTCCTAC CTGGCCTCCG CTCAAAGAAG ATGCAGACAG CGCCCTGCCA
 501  CGCCACAGCG TCCCGGTGCC CGCCACAGAA CTGGGCTCCA CCGAGCTGGT
 551  GACCACCAAG ACAGCTGGCC AGAGCAATA GCAGCAGTGG AGGCTGGAAC
 601  CCAGGGATCT CTACTGGGCT TGTGGACTTC ACCCAACAGC TTGGGAAAGA
 651  ACTTGGCCCT TCAGTGACGG AGTCCTTTGC CTGGGGGCG AACCCGGCAG
 701  AACCAGACAC TACAGGCCAC ATGAGATTGC TTTTGTGTTA GCTCTTGACT
 751  TGAGAACGTT CCATTTCTGA GATGGTTTTT AAGCCTGTGT GCCTTCAGAT
 801  GGTTGGATAG ACTTGAGGGT TGCATATTTA ATCTCTGTAG TGAGTCGGAG
 851  ACTGGAAACT TAATCTCGTT CTAAAAATTT TGGATTACTG GGCTGGAGGT
 901  ATGGCTCAGC AGTTCGGTTT GTGTGCTGTT CTAGCCGAGG ACTCCAGTTG
 951  TTCAGCTTCC CGGAACTCAG ATCTGGCAGC TTAAGACCAC CTGTCACTCC
1001  AGCCCCTGGA ACATCCTTGC CTCCAAAGGC ACCAGCACTC ATTTGCTCTA
1051  GAGCACACAC ACACACACAC ACACACACAC ACACACACAC ACACACACAT
1101  ATGCATGCAT GCACACTTAA AAATGTCAAA ATTAGCGGCT GGAGAAATTC
1151  ATGGTCAACA GCGCTTACTG TGATTCCAGA GGATGAGAGT TTGATTCCCA
1201  GAATGCACTG CGGGTGGCTC ATTACTGAGC ATAACTTTTG CTTCAGGGA
1251  CCTGATGCCT CTGGACTTCA TGGGCATCTG TATTCACGTG CACATCCTAC
1301  ACACACACAC ACACACACAC ACAGACATAC ACACACACAC ACTCTTTTAC
1351  AAATGATAAA ATATAAGATA GGCATGGTGG TACACACCTT TAATCCCAAC
1401  ATTGGGGAAG CAAAGGCAGG CAGGTAACTG AGTTGGAGGC CATCCTGGTC
1451  TACATAGCAA GTTCCAGGCT AACCAGAGCT AAATGGTGAG ACCAAGTCTC
1501  AAAATAATAC TCCCCCCCCA AAAAAAAAA ACTTTTAAAT TTTGATTTTT
1551  TTCTTTTATT ATTATTTTTT ATATTAATTT CATGGTGTTT AGAAGTGGTA
1601  TACTTAGATG GTGACTAAGA GGAGGTAAAG CCATCAGGAC TGAGCCCCTA
1651  ACATACAAGG AGAAAGCAGA GACAATGAAC ACGCCCCTCT CCTGCTGTGT
1701  GCCAGCTCTG GACCACCAGC CAGAGGGCAA TCATCAGATG TGGGCCCTAG
1751  AACCTTCAGA GCCGAAAGCT AAATCAATCT CATTTCTTTG TAAAGCTATT
1801  TAGCCTTAGG TGTTTTGTTA CGGTGATATA AAATGGACTA ACACAGGCAC
1851  TATGAGTAAG AAGCTTTTCT TTGAGCTGGG AAAGGTACTG TTAAACCAAA
1901  ATTAATCTGA ATAAAAAAAG GCTAAGGGGA AGACACTTAA AAA
```

Figure 4B

Murine BAFF-R Amino Acid Sequence

MGARRLRVRSQRSRDSSVPTQCNQTECFDPLVRNCVSCEL

FHTPDTGHTSSLEPGTALQPQEGSALRPD VALLVGAPALLG

LILALTLVG LVSLVSW RWRQQLRTASPDTSEGVQQESLEN

VFVPSSETPHASAPTWPPLKEDADSALPRHSVPVPATELGS

TELVTTKTAGPEQ

FIGURE 9

```
  1 ATGGAGACAGACACACTCCTGTTATGGGTGCTGCTGCTCTGGGTTCCAGGTTCCACTGGT
    M  E  T  D  T  L  L  L  W  V  L  L  L  W  V  P  G  S  T  G

61 GACGTCAGGCGAGGGCCCCGGAGCCTGCGGGGCAGGGACGCGCCAGCCCCCACGCCCTGC
    D  V  R  R  G  P  R  S  L  R  G  R  D  A  P  A  P  T  P  C

121 GTCCCGGCCGAGTGCTTCGACCTGCTGGTCCGCCACTGCGTGGCCTGCGGGCTCCTGCGC
    V  P  A  E  C  F  D  L  L  V  R  H  C  V  A  C  G  L  L  R

181 ACGCCGCGGCCGAAACCGGCCGGGGCCAGCAGCCCTGCGCCCAGGACGGCGCTGCAGCCG
    T  P  R  P  K  P  A  G  A  S  S  P  A  P  R  T  A  L  Q  P

241 CAGGAGTCGGTGGGCGCGGGGGCCGGCGAGGCGGCGGTCGACAAAACTCACACATGCCCA
    Q  E  S  V  G  A  G  A  G  E  A  A  V  D  K  T  H  T  C  P

301 CCGTGCCCAGCACCTGAACTCCTGGGGGGACCGTCAGTCTTCCTCTTCCCCCCAAAACCC
    P  C  P  A  P  E  L  L  G  G  P  S  V  F  L  F  P  P  K  P

361 AAGGACACCCTCATGATCTCCCGGACCCCTGAGGTCACATGCGTGGTGGTGGACGTGAGC
    K  D  T  L  M  I  S  R  T  P  E  V  T  C  V  V  V  D  V  S

421 CACGAAGACCCTGAGGTCAAGTTCAACTGGTACGTGGACGGCGTGGAGGTGCATAATGCC
    H  E  D  P  E  V  K  F  N  W  Y  V  D  G  V  E  V  H  N  A

481 AAGACAAAGCCGCGGGAGGAGCAGTACAACAGCACGTACCGTGTGGTCAGCGTCCTCACC
    K  T  K  P  R  E  E  Q  Y  N  S  T  Y  R  V  V  S  V  L  T

541 GTCCTGCACCAGGACTGGCTGAATGGCAAGGAGTACAAGTGCAAGGTCTCCAACAAAGCC
    V  L  H  Q  D  W  L  N  G  K  E  Y  K  C  K  V  S  N  K  A

601 CTCCCAGCCCCCATCGAGAAAACCATCTCCAAAGCCAAAGGGCAGCCCCGAGAACCACAG
    L  P  A  P  I  E  K  T  I  S  K  A  K  G  Q  P  R  E  P  Q

661 GTGTACACCCTGCCCCCATCCCGGGATGAGCTGACCAAGAACCAGGTCAGCCTGACCTGC
    V  Y  T  L  P  P  S  R  D  E  L  T  K  N  Q  V  S  L  T  C

721 CTGGTCAAAGGCTTCTATCCCAGCGACATCGCCGTGGAGTGGGAGAGCAATGGGCAGCCG
    L  V  K  G  F  Y  P  S  D  I  A  V  E  W  E  S  N  G  Q  P

781 GAGAACAACTACAAGACCACGCCTCCCGTGTTGGACTCCGACGGCTCCTTCTTCCTCTAC
    E  N  N  Y  K  T  T  P  P  V  L  D  S  D  G  S  F  F  L  Y

841 AGCAAGCTCACCGTGGACAAGAGCAGGTGGCAGCAGGGGAACGTCTTCTCATGCTCCGTG
    S  K  L  T  V  D  K  S  R  W  Q  Q  G  N  V  F  S  C  S  V

901 ATGCATGAGGCTCTGCACAACCACTACACGCAGAAGAGCCTCTCCCTGTCTCCGGGAAA
    M  H  E  A  L  H  N  H  Y  T  Q  K  S  L  S  L  S  P  G  K

961 TGA
```

Figure 13:
A
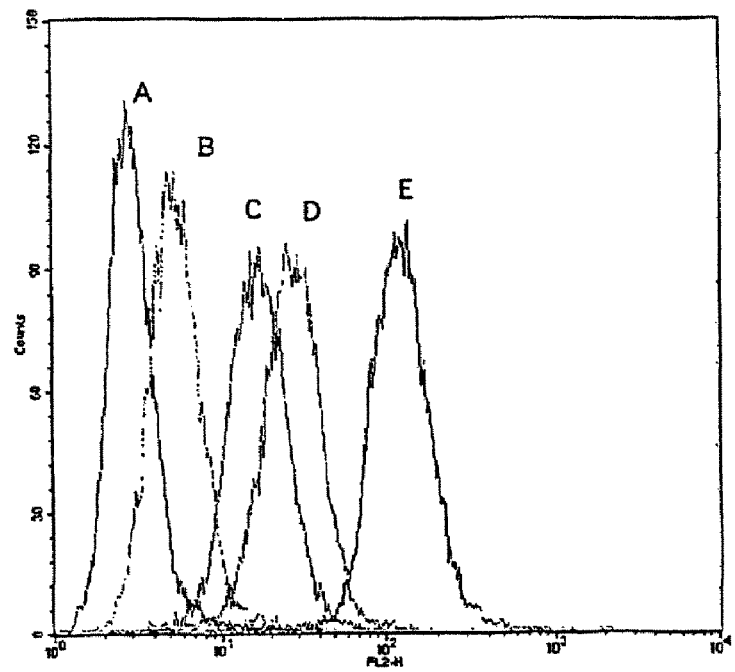
B
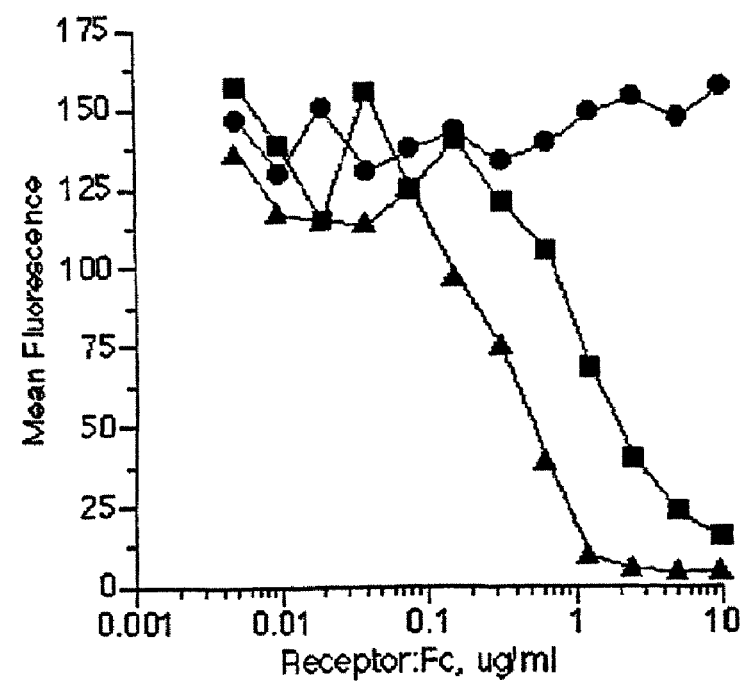

BAFF-R-Fc Treatment Results in a Reduction in Spleen Weight

Mice received 200 μg of HIgG, mBAFF-R-Fc or hBAFF-R-Fc on days 1, 4, 8, 11, 15, 18, 22 and 25. Mice were euthanized on day 28, spleens were harvested and weights were recorded.

Human and mouse BAFF-R-Fc Treatment Reduces the Number of Splenic B220+ B Cells

Mice received 200 µg of HIgG, mBAFF-R-Fc or hBAFF-R-Fc on days 1, 4, 8, 11, 15, 18, 22 and 25. Mice were euthanized on day 28 and spleens were harvested for analysis of B cell number.

Mice received 200 µg of HIgG, mBAFF-R-Fc or hBAFF-R-Fc on days 1, 4, 8, 11, 15, 18, 22 and 25. Peripheral blood was collected prior to sacrifice on day 28, and the percent of B220+ lymphocytes was determined.

Figure 19
A
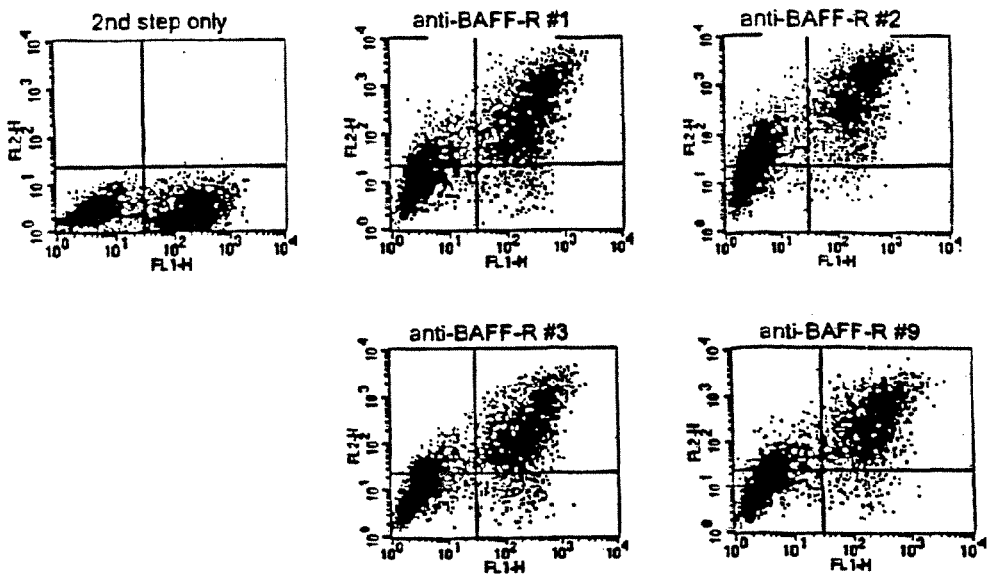
B
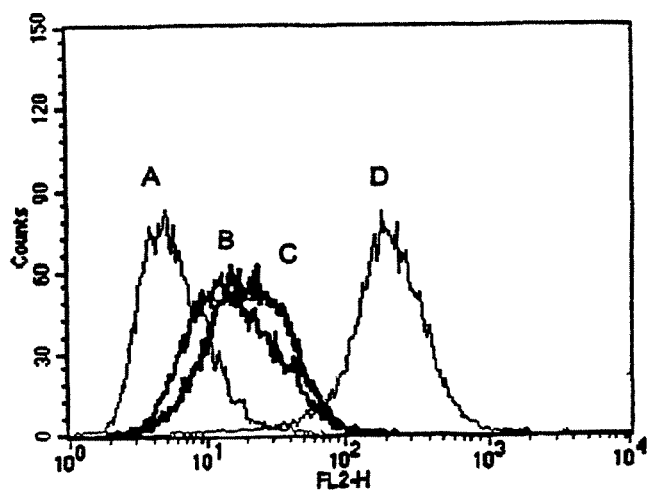

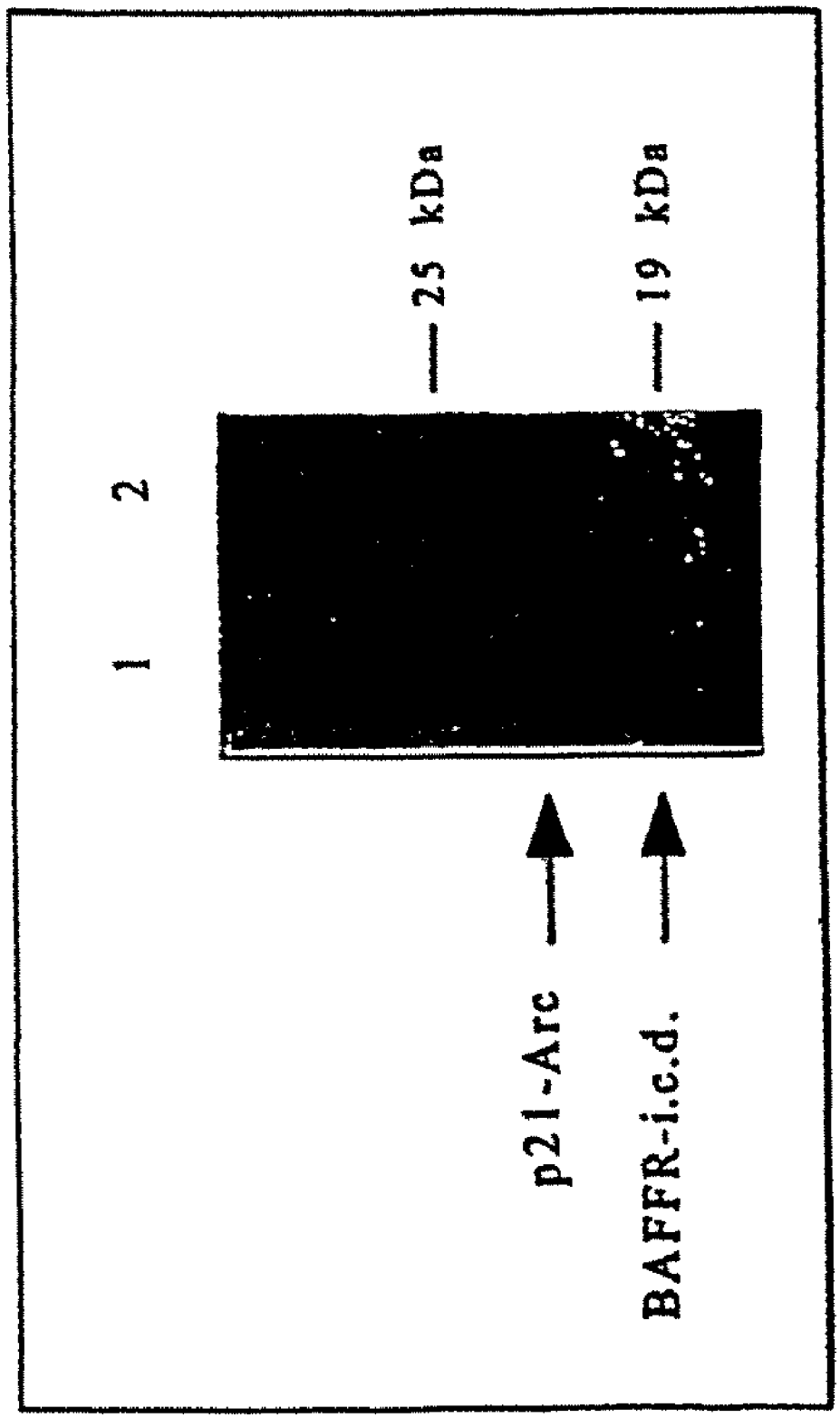

BAFF RECEPTOR ANTIBODIES AND METHODS

This application is a divisional of U.S. application Ser. No. 10/380,703 (incorporated herein by reference), filed Jul. 28, 2003, now U.S. Pat. No. 7,112,421 which is a National Stage Entry of PCT/US01/28006, filed Sep. 6, 2001, which claims the benefit of U.S. Provisional Application No. 60/312,185, filed Aug. 14, 2001, U.S. Provisional Application No. 60/268,499, filed Feb. 13, 2001, U.S. Provisional Application No. 60/234,140, filed Sep. 21, 2000, and U.S. Provisional Application No. 60/233,152, filed Sep. 18, 2000.

FIELD OF THE INVENTION

The present invention provides a novel receptor protein. The invention generally relates to nucleic acids and polypeptides. The invention relates more particularly to nucleic acids encoding polypeptides related to a receptor to BAFF, a B-cell activating factor belonging to the Tumor Necrosis Factor ("TNF") family, which is associated with the expression of B-cells and immunoglobulins. This receptor can be employed in the treatment of cancers, lymphomas, autoimmune diseases or inherited genetic disorders involving B-cells.

BACKGROUND OF THE INVENTION

The present invention relates to a novel receptor in the TNF family. A novel receptor has been identified as the BAFF receptor ("BAFF-R").

The TNF family consists of pairs of ligands and their specific receptors referred to as TNF family ligands and TNF family receptors (Bazzoni and Beutler (1996) *N. Engl. J. Med.* 334(26):1717-1725. The family is involved in the regulation of the immune system and possibly other non-immunological systems. The regulation is often at a "master switch" level such that TNF family signaling can result in a large number of subsequent events best typified by TNF. TNF can initiate the general protective inflammatory response of an organism to foreign invasion that involves the altered display of adhesion molecules involved in cell trafficking chemokine production to drive specific cells into specific compartments, and the priming of various effector cells. As such, the regulation of these pathways has clinical potential.

Induction of various cellular responses mediated by such TNF family cytokines is believed to be initiated by their binding to specific cell receptors. At least two distinct TNF receptors of approximately 55 kDa (TNFR1) and 75 kDa (TNFR2) have been identified (Hohman et al. (1989) J. Biol. Chem. 264:14927-14934; and Brockhaus et al. (1990) Proc. Natl. Acad. Sci. USA 87:3127-3131). Extensive polymorphisms have been associated with both TNF receptor genes. Both TNFRs share the typical structure of cell surface receptors including extracellular, transmembrane and intracellular domains. The extracellular portion of type 1 and type 2 TNFRs contains a repetitive amino acid sequence pattern of four cysteine rich domains (CDRs). A similar repetitive pattern of CDRs exist in several other cell surface proteins, including p75 nerve growth factor receptor, the B-cell antigen CD40 amongst others.

The receptors are powerful tools to elucidate biological pathways because of their easy conversion to immunoglobulin fusion proteins. These dimeric soluble receptor forms are good inhibitors of events mediated by either secreted or surface bound ligands. By binding to these ligands they prevent the ligand from interacting with cell associated receptors that can signal. Not only are these receptor-Fc fusion proteins useful in an experimental sense, but they have been successfully used clinically in the case of TNF-R-Fc to treat inflammatory bowel disease, rheumatoid arthritis and the acute clinical syndrome accompanying OKT3 administration (Eason et al. (1996) *Transplantation* 61(2):224-228; Feldmann et al. (1996) *Int. Arch. Allergy Immunol.* 111(4):362-365; and van Dullemen et al. (1995) *Gastroenterol.* 109(1):129-135). One can envision that manipulation of the many events mediated by signaling through the TNF family of receptors will have wide application in the treatment of immune based diseases and also the wide range of human diseases that have pathological sequelae due to immune system involvement. A soluble form of a recently described receptor, osteoprotegerin, can block the loss of bone mass and, therefore, the events controlled by TNF family receptor signaling are not necessarily limited to immune system regulation (Simonet et al. (1997) *Cell* 89(2):309-319). Antibodies to the receptor can block ligand binding and hence can also have clinical application. Such antibodies are often very long-lived and may have advantages over soluble receptor-Fc fusion proteins which have shorter blood half-lives.

While inhibition of the receptor mediated pathway represents the most exploited therapeutic application of these receptors, originally it was the activation of the TNF receptors that showed clinical promise (Aggarwal and Natarajan (1996) *Eur Cytokine Netw.* 7(2):93-124). Activation of the TNF receptors can initiate cell death in the target cell and hence the application to tumors was and still is attractive (Eggermont et al. (1996) *Ann. Surg.* 224(6):756-765). The receptor can be activated either by administration of the ligand, i.e. the natural pathway or some antibodies that can crosslink the receptor are also potent agonists. Antibodies would have an advantage in oncology since they can persist in the blood for long periods whereas the ligands generally have short lifespans in the blood. As many of these receptors may be expressed more selectively in tumors or they may only signal cell death or differentiation in tumors, agonist antibodies could be good weapons in the treatment of cancer. Likewise, many positive immunological events are mediated via the TNF family receptors, e.g. host inflammatory reactions, antibody production etc. and therefore agonistic antibodies could have beneficial effects in other, non-oncological applications.

Paradoxically, the inhibition of a pathway may have clinical benefit in the treatment of tumors. For example the Fas ligand is expressed by some tumors and this expression can lead to the death of Fas positive lymphocytes thus facilitating the ability of the tumor to evade the immune system. In this case, inhibition of the Fas system could then allow the immune system to react to the tumor in other ways now that access is possible (Green and Ware (1997) *Proc. Natl. Acad. Sci. USA* 94(12):5986-90).

The TNF family ligand BAFF, also known as TALL-1, THANK, BLyS and zTNF4 (Schneider et al. (1999) *J. Exp. Med.* 189(11):1747-1756; Shu et al. (1999) *J. Leukoc. Biol.* 65(5):680-683; Mukhopadhyay et al. (1999) *J. Biol. Chem.* 274(23):15978-15981; Moore et al. (1999) *Science* 285(5425):260-263; Gross et al. (2000) *Nature* 404(6781): 995-999) enhances B cell survival in vitro (Batten et al. (2000) *J. Exp. Med.* 192(10):1453-1466) and has emerged as a key regulator of peripheral B cell populations in vivo. Mice over-expressing BAFF display mature B cell hyperplasia and symptoms of systemic lupus erythaematosus (SLE) (Mackay et al. (1999) *J. Exp. Med.* 190(11):1697-1710). As well, some SLE patients have significantly increased levels of BAFF in their serum (Zhang et al. (2001) *J. Immunol.* 166(1):6-10). It has therefore been proposed that abnormally high levels of this ligand may contribute to the pathogenesis of autoimmune diseases by enhancing the survival of autoreactive B cells (Batten et al. (2000) *J. Exp. Med.* 192(10):1453-1466).

BAFF, a type II membrane protein, is produced by cells of myeloid origin (Schneider et al. (1999) *J. Exp. Med.* 189(11): 1747-1756; Moore et al. (1999) *Science* 285(5425):260-263) and is expressed either on the cell surface or in a soluble form (Schneider et al. (1999) *J. Exp. Med.* 189(11):1747-1756). Two TNF receptor family members, BCMA and TACI have previously been shown to interact with BAFF (Gross et al. (2000) *Nature* 404:995-999; Thompson et al. (2000) *J. Exp. Med.* 192(1):129-135; Xia et al. (2000) *J. Exp. Med.* 192:137-143; Marsters et al. (2000) *Curr. Biol.* 10(13):785-788; Shu et al. (2000) *J. Leukoc. Biol.* 65(5):680-683; Wu et al. (2000) *J. Biol. Chem.* 275:35478-35485).

SUMMARY OF TE INVENTION

The present invention is based, in part, upon the discovery of "BAFF-R," a BAFF receptor protein, polynucleotide sequences and the BAFF-R polypeptides encoded by these nucleic acid sequences.

In one aspect, the invention provides an isolated nucleic acid which encodes a BAFF-R polypeptide, or a fragment or derivative thereof. The nucleic acid can include, e.g., nucleic acid sequence encoding a polypeptide at least 50% identical, or at least 90% identical, to a polypeptide comprising the amino acid sequence of FIG. 2D (SEQ ID NO:5).

The invention also provides a substantially pure nucleic acid molecule comprising a sequence that hybridizes under stringent conditions to a hybridization probe, the nucleic acid sequence of the probe consisting of the coding sequence of FIG. 2A (SEQ ID NO:3), FIG. 2C (SEQ ID NO:4) or the complement of said coding sequence.

In some embodiments, the nucleic acid sequence encodes a polypeptide having the sequence of FIG. 2D (SEQ ID NO:5) with at least one conservative amino acid substitution.

In some embodiments, the nucleic acid sequence encodes a polypeptide that binds BAFF.

The nucleic acid can include, e.g., a nucleic acid which includes the nucleotide sequence shown in FIG. 1A (SEQ ID NO:1), FIG. 1B (SEQ ID NO:2), FIG. 2A (SEQ ID NO:3), FIG. 2C (SEQ ID NO:4) and FIG. 3 (SEQ ID NO:6).

The nucleic acid can be, e.g., a genomic DNA fragment, or it can be a cDNA molecule. Also included in the invention is a vector containing one or more of the nucleic acids described herein, and a cell containing the vectors or nucleic acids described herein.

In another aspect, the invention provides a substantially pure nucleic acid molecule encoding a fusion protein comprising at least two segments, wherein one of the segments comprises a polypeptide or fragment thereof as described in the amino acid sequences set forth in the above embodiments of the invention. The invention also provides a fusion protein comprising at least two or three segments, wherein the first segment comprises a heterologous signal polypeptide, the second comprises a polypeptide or fragment thereof as described in the BAFF-R amino acid sequences set forth in the above embodiments of the invention and the third segment comprises an immunoglobulin polypeptide. Alternatively, the first segment comprises an immunoglobulin polypeptide fragment containing a signal sequence and the second segment comprises the BAFF-R polypeptide fragment.

In other aspects, the invention provides a substantially pure binding agent that specifically binds to the polypeptide of the above-stated embodiments of the invention.

The present invention is also directed to host cells transformed with a recombinant expression vector comprising any of the nucleic acid molecules described above.

In another aspect, the invention includes a pharmaceutical composition that includes a BAFF-R nucleic acid and a pharmaceutically acceptable carrier or diluent.

In a further aspect, the invention includes a substantially purified BAFF-R polypeptide, e.g., any of the polypeptides encoded by a BAFF-R nucleic acid.

The invention also includes a pharmaceutical composition that includes a BAFF-R polypeptide and a pharmaceutically acceptable carrier or diluent.

In a still further aspect, the invention provides an antibody that binds specifically to a BAFF-R polypeptide. The antibody can be, e.g., a monoclonal or polyclonal antibody. The invention also includes a pharmaceutical composition including BAFF-R antibody and a pharmaceutically acceptable carrier or diluent. The present invention is also directed to isolated antibodies that bind to an epitope on a polypeptide encoded by any of the nucleic acid molecules described above.

The present invention is further directed to kits comprising antibodies that bind to a polypeptide encoded by any of the nucleic acid molecules described above and a negative control antibody.

The invention further provides a method for producing a BAFF-R polypeptide. The method includes providing a cell containing a BAFF-R nucleic acid, e.g., a vector that includes a BAFF-R nucleic acid, and culturing the cell under conditions sufficient to express the BAFF-R polypeptide encoded by the nucleic acid. The expressed BAFF-R polypeptide is then recovered from the cell. Preferably, the cell produces little or no endogenous BAFF-R polypeptide. The cell can be, e.g., a prokaryotic cell or eukaryotic cell.

The present invention provides a method of inducing an immune response in a mammal against a polypeptide encoded by any of the nucleic acid molecules disclosed above by administering to the mammal an amount of the polypeptide sufficient to induce the immune response.

The present invention is also directed to methods of identifying a compound that binds to BAFF-R polypeptide by contacting the BAFF-R polypeptide with a compound and determining whether the compound binds to the BAFF-R polypeptide.

The present invention is also directed to methods of identifying a compound that binds a nucleic acid molecule encoding BAFF-R polypeptide by contacting BAFF-R nucleic acid with a compound and determining whether the compound binds the nucleic acid molecule.

The invention further provides methods of identifying a compound that modulates the activity of a BAFF-R polypeptide by contacting BAFF-R polypeptide with a compound and determining whether the BAFF-R polypeptide activity is modified.

The present invention is also directed to compounds that modulate BAFF-R polypeptide activity identified by contacting a BAFF-R polypeptide with the compound and determining whether the compound modifies activity of the BAFF-R polypeptide, binds to the BAFF-R polypeptide, or binds to a nucleic acid molecule encoding a BAFF-R polypeptide.

In another aspect, the invention provides a method of diagnosing a B-cell mediated condition, e.g., an autoimmune disorder or cancer, in a subject. The method includes providing a protein sample from the subject and measuring the amount of BAFF-R polypeptide in the subject sample. The amount of BAFF-R in the subject sample is then compared to the amount of BAFF-R polypeptide in a control protein sample. An alteration in the amount of BAFF-R polypeptide in the subject protein sample relative to the amount of BAFF-R polypeptide in the control protein sample indicates the subject has a B-cell mediated condition. A control sample is preferably taken from a matched individual, i.e., an individual of similar age, sex, or other general condition but who is not suspected of having the condition. Alternatively, the control sample may be taken from the subject at a time when the subject is not suspected of having the disorder. In some embodiments, the BAFF-R polypeptide is detected using a BAFF-R anybody.

In a further aspect, the invention includes a method of diagnosing a B-cell mediated condition, e.g., autoimmune disorder in a subject. The method includes providing a nucleic acid sample, e.g., RNA or DNA, or both, from the subject and measuring the amount of the BAFF-R nucleic acid in the subject nucleic acid sample. The amount of BAFF-R nucleic acid sample in the subject nucleic acid is then compared to the amount of BAFF-R nucleic acid in a control sample. An alteration in the amount of BAFF-R nucleic acid in the sample relative to the amount of BAFF-R in the control sample indicates the subject has an autoimmune condition.

In a further aspect, the invention includes a method of diagnosing a tumorigenic or autoimmune condition in a subject. The method includes providing a nucleic acid sample from the subject and identifying at least a portion of the nucleotide sequence of a BAFF-R nucleic acid in the subject nucleic acid sample. The BAFF-R nucleotide sequence of the subject sample is then compared to a BAFF-R nucleotide sequence of a control sample. An alteration in the BAFF-R nucleotide sequence in the sample relative to the BAFR-R nucleotide sequence in said control sample indicates the subject has such a condition.

In a still farther aspect, the invention provides method of treating or preventing or delaying a B-cell mediated condition. The method includes administering to a subject in which such treatment or prevention or delay is desired a BAFF-R nucleic acid, a BAFF-R polypeptide, or an anti-BAFF-R antibody in an amount sufficient to treat, prevent, or delay a tumorigenic or immunoregulatory condition in the subject.

The conditions diagnosed, treated, prevented or delayed using the BAFF-R nucleic acid molecules, polypeptides or antibodies can be a cancer or an immunoregulatory disorder. Diseases include those that are autoimmune in nature such as systemic lupus erythematosus, rheumatoid arthritis, myasthenia gravis, autoimmune hemolytic anemia, idiopathic thrombocytopenia purpura, anti-phospholipid syndrome, Chagas' disease, Grave's disease, Wegener's granulomatosis, poly-arteritis nodosa and rapidly progressive glomerulonephritis. The therapeutic agent also has application in plasma cell disorders such as multiple myeloma, Waldenstrom's macroglobulinemia, heavy-chain disease, primary or immunocyte-associated amyloidosis, and monoclonal gammopathy of undetermined significance (MGUS). Oncology targets include B cell carcinomas, leukemias, and lymphomas.

Compositions and methods of treatment using the nucleic acids, polypeptides and antibodies of the present invention can be used with any condition associated with undesired cell proliferation. In particular, the present invention can be used to treat tumor cells which express BAFF and/or BAFF-R.

Compositions of the invention comprising BAFF-R agonists (such as antibodies that bind to BAFF-R and mimic BAFF) also may be used to treat immune deficiencies marked by low amounts of B cells, for example. Such disorders may be caused by radiation and/or chemotherapy, for example.

In another aspect of the invention a method for decreasing aggregation of a recombinantly expressed protein is provided. The method comprises comparison of homologs of a protein or fusion protein thereof to determine conserved domains and non-identical amino acids within conserved regions. Generally, at least one non-polar amino acid is changed to an uncharged polar amino acid or to a proline, alanine or serine.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1A shows the DNA sequence of the BJAB cDNA (SEQ ID NO:1) cloned in pJST576.

FIG. 1B shows the complete DNA sequence of the cDNA of the IMAGE clone 2000271 (EST AI250289) (SEQ ID NO:2).

FIG. 2A shows the nucleotide sequence of JST576 with an intron removed as predicted by the GENESCAN program (SEQ ID NO:3).

FIG. 2B shows a 1% agarose gel of PCR products obtained for BAFF-R using either first strand cDNA generated from BJAB or IM-9 RNA or on JST576 cDNA. Lane 1. Lambda DNA HindIII digest. Lane 2. BJAB oligo dT primed BAF-225/BAF-191. Lane 3. BJAB oligo dT primed BAF-226/BAF-191. Lane 4. BJAB random primed BAF-225/BAF-191. Lane 5. BJAB random primed BAF-226/BAF-191. Lane 6. IM-9 oligo dT primed BAF-225/BAF-191. Lane 7. IM-9 oligo dT primed BAF-226/BAF-191. Lane 8. IM-9 random primed BAF-225/BAF-191. Lane 9. IM-9 random primed BAF-226/BAF-191. Lane 10. JST576 cDNA BAF-225/BAF-191. Lane 11. JST576 cDNA BAF-226/BAF-191. Lane 12. No template BAF-225/BAF-191. Lane 13. No template BAF-226BAF-191.

FIG. 2C shows the mature JST576(BAFF-R) sequence (SEQ ID NO:4) (also GenBank Accession No. AF373846) determined by sequencing bulk PCR product flanking the predicted intron from BJAB first stand cDNA.

FIG. 2D shows the amino acid sequence of BAFF-R (JST576) (SEQ ID NO:5). The A (Ala) residue in bold indicates the sequence resulting from the use of the alternative splice acceptor site. The predicted transmembrane domain is boxed and the putative stop transfer signal is underlined.

FIG. 3 depicts the spliced version of JST576 (SEQ ID NO:6) containing 5' UTR sequence obtained by RT-PCR from human spleen first strand cDNA, and the deduced amino acid sequence (SEQ ID NO:7). This sequence contains an upstream stop codon in frame with the ATG.

FIG. 4A shows the sequence of the murine BAFF-R cDNA (SEQ ID NO:8) (also GenBank Accession No. AF373847).

FIG. 4B shows the amino acid sequence of murine BAFF-R (SEQ ID NO:9). The Cys residues are bold and underlined and the predicted transmembrane region is boxed.

FIG. 9 depicts the nucleic acid sequence (SEQ ID NO:11) and its derived amino acid sequence (SEQ ID NO:12) of a gene encoding a human BAFF-R:Fc: nucleic acid residues 1-63 encode the murine IgG-kappa signal sequence; nucleic acid residues 64-66 were used to introduce a restriction enzyme site, nucleic acid residues 67-276 encode part of the BAFF-R extracellular domain, nucleic acid residues 277-279 were used to introduce a restriction enzyme site, and nucleic acid residues 280-960 encode the Fc region of human IgG1.

FIG. 13 shows that human BAFF-R:Fc blocks human BAFF binding to BJAB cells. The results of FACS analysis are shown in FIG. 13A. Curve E represents biotinylated BAFF binding to BJAB cells in the absence of BAFF-R:Fc. Curves B-D represent the ability of BAFF to bind to BJAB cells in the presence of 5 ug/ml, 1 ug/ml or 0.2 ug/ml, respectively. Curve A is the second step only curve. FIG. 13B illustrates the ability of various concentrations of BAFF-R:Fc (squares) compared to TACI:Fc (triangles) or a nonspecific fusion protein, LT_R:Fc (circles), to block the binding of BAFF to the receptor expressing BJAB cells.

FIG. 19A shows FACS data from supernatants of four clones that produce antibodies that bind BAFF-R. Also shown is control supernatant which does not contain antibodies that binds BAFF-R.

FIG. 19B shows a histogram showing that two clones that block BAFF binding to BAFF-R. (a) shows the no BAFF control; (b) shows the blocking ability of the antibody from clone 2; (c) shows the blocking ability of the antibody from clone 9; and (d) shows the curve from a control antibody that does not bind BAFF-R.

FIG. 21 shows an autoradiograph of proteins immunoprecipitated using lysates prepared from BAFF-R-i.c.d. (BAFF-R intracellular domain) (lane 1), or control vector- (lane 2) transfected cells. Approximately 6×10$^6$ 293E cells were transfected with a construct encoding BAFFR-i.c.d. or mock plasmid. After 48 hours, the cells were metabolically labeled with $^{35}$S for 24 hours, lysed with lysis buffer, precleared, and immunoprecipitated with an antimyc mAb, 9E10. The immunoprecipitates were separated by 10-20% SDS PAGE under reducing condition.

DETAILED DESCRIPTION OF THE INVENTION

Figure 4C:
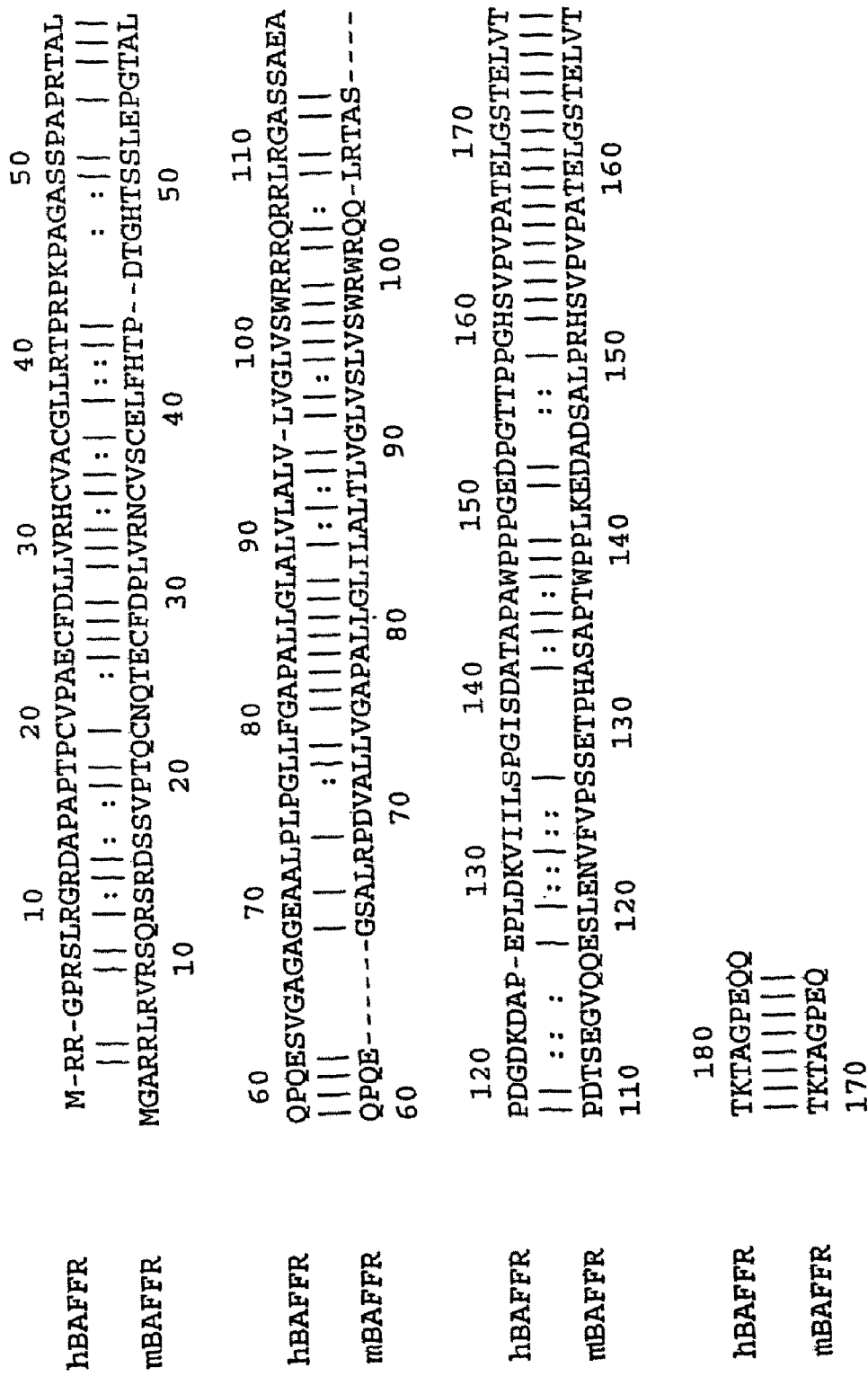
FIG. 4C shows the homology between human (SEQ ID NO:10) and murine (SEQ ID NO:9) BAFF-R protein sequences.

The reference works, patents, patent applications, and scientific literature, including accession numbers to GenBank database sequences, that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

The present invention discloses BAFF-R nucleic acids, isolated nucleic acids that encode BAFF-R polypeptide or a portion thereof, BAFF-R polypeptides, vectors containing these nucleic acids, host cells transformed with the BAFF-R nucleic acids, anti-BAFF-R antibodies, and pharmaceutical compositions. Also disclosed are methods of making BAFF-R polypeptides, as well as methods of screening, diagnosing, treating conditions using these compounds, and methods of screening compounds that modulate BAFF-R polypeptide activity.

The BAFF-R nucleic acids and polypeptides, as well as BAFF-R antibodies, as well as pharmaceutical compositions discussed herein, are useful, inter alia, in treating cancer and/or immunoregulatory conditions. These disorders include, e.g., B cell-mediated diseases that are autoimmune in nature such as systemic lupus erythematosus, rheumatoid arthritis myasthenia gravis, autoimmune hemolytic anemia, idiopathic thrombocytopenia purpura, anti-phospholipid syndrome, Chagas' disease, Grave's disease, Wegener's granulomatosis, poly-arteritis nodosa and rapidly progressive glomerulonephritis. This therapeutic agent also has application in plasma cell disorders such as multiple myeloma, Waldenstrom's macroglobulinemia, heavy-chain disease, primary or immunocyte-associated amyloidosis, and monoclonal gammopathy of undetermined significance (MGUS). Oncology targets include B cell carcinomas, leukemias, and lymphomas.

BAFF-R Nucleic Acids

One aspect of the invention pertains to isolated nucleic acid molecules that encode BAFF-R proteins or biologically active portions thereof. Also included are nucleic acid fragments sufficient for use as hybridization probes to identify BAFF-R-encoding nucleic acids (e.g., BAFF-R mRNA) and fragments for use as polymerase chain reaction (PCR) primers for the amplification or mutation of BAFF-R nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt) or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BAFF-R nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

Figure 2D:
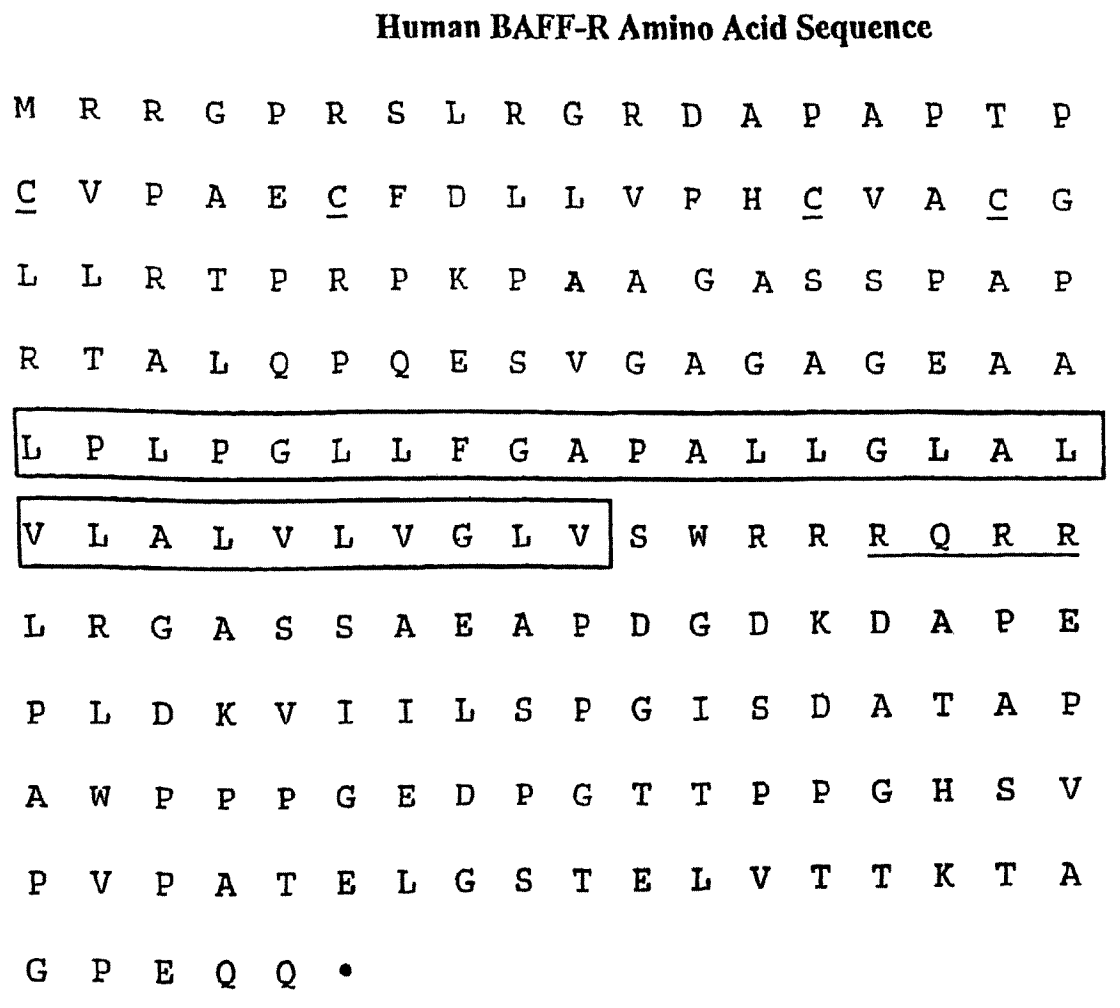

A nucleic acid molecule of the present invention, e.g., a nucleic acid molecule having the nucleotide sequence of FIG. 1A (SEQ ID NO:1), FIG. 1B (SEQ ID NO:2), FIG. 2A (SEQ ID NO:3), FIG. 2C (SEQ ID NO:4) and FIG. 3 (SEQ ID NO:6), or a complement of any of these nucleotide sequences, can be isolated using standard molecular biology techniques and the sequence information provided herein. Using all or a portion of the nucleic acid sequences of FIG. 1A, B, 2A, C and 3 as a hybridization probe, BAFF-R nucleic acid sequences can be isolated using standard hybridization and cloning techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., $C_{URRENT}$ PROTOCOLS IN MOLECULAR BIOLOGY, John Wiley & Sons, New York, N.Y., 1993).

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to BAFF-R nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nt and as many as 50 nt, preferably about 15 nt to 30 nt. They may be chemically synthesized and may be used as probes.

In another embodiment, an isolated nucleic acid molecule of the invention comprises a nucleic acid molecule that is a complement of the nucleotide sequence shown in FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6). In another embodiment, an isolated nucleic acid molecule of the invention comprises a nucleic acid molecule that is a complement of the nucleotide sequence shown in FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6), or a portion of this nucleotide sequence. A nucleic acid molecule that is complementary to the nucleotide sequence shown in FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6) is one that is sufficiently complementary to the nucleotide sequence shown in FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6) that it can hydrogen bond with little or no mismatches to the nucleotide sequence shown in FIG. 1A (SEQ ID NO:1), FIG. 1B (SEQ ID NO:2), FIG. 2A (SEQ ID NO:3), FIG. 2C (SEQ ID NO:4) and FIG. 3 (SEQ ID NO:6) thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6), e.g., a fragment that can be used as a probe or primer or a fragment encoding a biologically active portion of BAFF-R. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 45%, 50%, 70%, 80%, 95%, 98%, or even 99% identity (with a preferred identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (1981) *Adv. Appl. Math.* 2:482489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of BAFF-R polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a BAFF-R polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human BAFF-R protein. Homologous nucleic acid sequences include those nucleic acid sequences that encode conservative amino acid substitutions (see below) in FIG. 2D (SEQ ID NO:5) as well as a polypeptide having BAFF-R activity. A homologous amino acid sequence does not encode the amino acid sequence of a human BAFF-R polypeptide.

The nucleotide sequence determined from the cloning of the human BAFF-R gene allows for the generation of probes and primers designed for use in identifying and/or cloning BAFF-R homologues in other cell types, e.g., from other tissues, as well as BAFF-R homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of any of FIG. 1A (SEQ ID NO:1), FIG. 1B (SEQ ID NO:2), FIG. 2A (SEQ ID NO:3), FIG. 2C (SEQ ID NO:4) and FIG. 3 (SEQ ID NO:6) or an anti-sense strand nucleotide sequence of any of FIG. 1A (SEQ ID NO:1), FIG. 1B (SEQ ID NO:2), FIG. 2A (SEQ ID NO:3), FIG. 2C (SEQ ID NO:4), and 3 (SEQ ID NO:6) or of a naturally occurring mutant of any of FIG. 1A (SEQ ID NO:1), FIG. B (SEQ ID NO:2), FIG. 2A (SEQ ID NO:3), FIG. 2C (SEQ ID NO:4), and FIG. 3 (SEQ ID NO:6).

Probes based on the human BAFF-R nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a BAFF-R protein, such as by measuring a level of a BAFF-R-encoding nucleic acid in a sample of cells from a subject e.g., detecting BAFF-R mRNA levels or determining whether a genomic BAFF-R gene has been mutated or deleted.

"A polypeptide having a biologically active portion of BAFF-R" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of BAFF-R" can be prepared by isolating a portion of any of FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6) that encodes a polypeptide having a BAFF-R biological activity (biological activities of the BAFF-R proteins are described below), expressing the encoded portion of BAFF-R protein (e.g., by recombinant expression in vitro) and assessing the activity of the encoded portion of BAFF-R. For example, a nucleic acid fragment encoding a biologically active portion of BAFF-R can optionally include a BAFF binding domain. In another embodiment, a nucleic acid fragment encoding a biologically active portion of BAFF-R includes one or more regions.

BAFF-R Variants

The invention on further encompasses nucleic acid molecules that differ from the nucleotide sequences shown in FIG. 1A (SEQ ID NO:1), FIG. 1B (SEQ ID NO:2), FIG. 2A (SEQ ID NO:3), FIG. 2C (SEQ ID NO:4), and 3 (SEQ ID NO:6) due to degeneracy of the genetic code. These nucleic acids thus encode the same BAFF-R protein as that encoded by the nucleotide sequence shown in FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6). In another embodiment, an isolated nucleic acid molecule of the invention has a nucleotide sequence encoding a protein having an amino acid sequence shown in FIG. 2D (SEQ ID NO:5).

In addition to the human BAFF-R nucleotide sequence shown in any of FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6), it will be appreciated by those skilled in the art that DNA sequence polymorphisms that lead to changes in the amino acid sequences of BAFF-R may exist within a population (e.g., the human population). Such genetic polymorphism in the BAFF-R gene may exist among individuals within a population due to natural allelic variation. As used herein, the terms "gene" and "recombinant gene" refer to nucleic acid molecules comprising an open reading frame encoding a BAFF-R protein, preferably a mammalian BAFF-R protein. Such natural allelic variations can typically result in 1-5% variance in the nucleotide sequence of the BAFF-R gene. Any and all such nucleotide variations and resulting amino acid polymorphisms in BAFF-R that are the result of natural allelic variation and that do not alter the functional activity of BAFF-R are intended to be within the scope of the invention.

Moreover, nucleic acid molecules encoding BAFF-R proteins from other species, and thus that have a nucleotide sequence that differs from the human sequences of FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6) are intended to be within the scope of the invention. Nucleic acid molecules corresponding to natural allelic variants and homologues of the BAFF-R cDNAs of the invention can be isolated based on their homology to the human BAFF-R nucleic acids disclosed herein using the human cDNAs, or a portion thereof, as a hybridization probe according to standard hybridization techniques under stringent hybridization conditions. For example, a soluble human BAFF-R cDNA can be isolated based on its homology to human membrane-bound BAFF-R. Likewise, a membrane-bound human BAFF-R cDNA-can be isolated based on its homology to soluble human BAFF-R Accordingly, in another embodiment, an isolated nucleic acid molecule of the invention is at least 6 nucleotides in length and hybridizes under stringent conditions to the nucleic acid molecule comprising the nucleotide sequence of any of FIG. 1A (SEQ ID NO:1), FIG. 1B (SEQ ID NO:2), FIG. 2A (SEQ ID NO:3), FIG. 2C (SEQ ID NO:4), and FIG. 3 (SEQ ID NO:6). In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding BAFF-R proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide. Stringent conditions are known to those skilled in the art and can be found in CURRNT PROTOCOLS IN MOLECULAR BIOLOGY, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1, SEQ ID NO:2, SEQ ID NO:3, SEQ ID NO:4, SEQ ID NO:6 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of any of FIG. 1A (SEQ ID NO:1), FIG. 1B (SEQ ID NO:2), FIG. 2A (SEQ ID NO:3), FIG. 2C (SEQ ID NO:4), and 3 (SEQ ID NO:6) or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al., Eds., CURRENT PROTOCOLS IN MOLECULAR BIOLOGY, John Wiley & Sons, NY, 1993; and Kriegler, GENE TRANSFER AND EXPRESSION, A LABORATORY MANUAL, Stockton Press, NY, 1990.

In a third embodiment, a nucleic acid that is hybridizable to the nucleic acid molecule comprising the nucleotide sequence of any of FIG. 1A (SEQ ID NO:1), FIG. 2B(SEQ ID NO:2), FIG. 2A (SEQ ID NO:3), FIG. 2C (SEQ ID NO:4), and FIG. 3 (SEQ ID NO:6) or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that maybe used are well known in the art (e.g., as employed for cross-species hybridizations). See, e.g. Ausubel et at, Eds., CURRENT PROTOCOLS IN MOLECULAR BIOLOGY, John Wiley & Sons, NY, 1993; and Kriegler, GENE TRANSFER AND EXPRESSION, A LABORATORY MANUAL, Stockton Press, NY, 1990; Shilo and Weinberg (1981) *Proc Natl. Acad. Sci. USA* 78:6789-6792.

Conservative Mutations

In addition to naturally-occurring allelic variants of the BAFF-R sequence that may exist in the population, the skilled artisan will further appreciate that changes can be introduced by mutation into the nucleotide sequence of FIG. 2A (SEQ ID NO:3), FIG. 2C (SEQ ID NO:4), FIG. 3 (SEQ ID NO:6) thereby leading to changes in the amino acid sequence of the encoded BAFF-R protein, without altering the functional ability of the BAFF-R protein. For example, nucleotide substitutions leading to amino acid substitutions at "non-essential" amino acid residues can be made in the sequence of any of FIG. 2A (SEQ ID NO:3), FIG. 2C (SEQ ID NO:4), and FIG. 3 (SEQ ID NO:6). A "non-essential" amino acid residue is a residue that can be altered from the wild-type sequence of BAFF-R without altering the biological activity, whereas an "essential" amino acid residue is required for biological activity. For example, amino acid residues that are conserved among the BAFF-R proteins of the present invention, are predicted to be particularly unamenable to alteration.

In addition, amino acid residues that are conserved among family members of the BAFF-R proteins of the present invention, are also predicted to be particularly unamenable to alteration. For example, BAFF-R proteins of the present invention can contain at least one domain that is a typically conserved region in TNF family members. As such, these conserved domains are not likely to be amenable to mutation. Other amino acid residues, however, (e.g., those that are not conserved or only semi-conserved among members of the BAFF-R proteins) may not be essential for activity and thus are likely to be amenable to alteration.

Another aspect of the invention pertains to nucleic acid molecules encoding BAFF-R proteins that contain changes in amino acid residues that are not essential for activity. Such BAFF-R proteins differ in amino acid sequence from FIG. 2D (SEQ ID NO:5), yet retain biological activity. In one embodiment, the isolated nucleic acid molecule-comprises a nucleotide sequence encoding a protein, wherein the protein comprises an amino acid sequence at least about 45% homologous to the amino acid sequence of FIG. 2D (SEQ ID NO:5). Preferably, the protein encoded by the nucleic acid molecule is at least about 60% homologous to FIG. 2D (SEQ ID NO:5), more preferably at least about 70%, 80%, 90%, 95%, 98%, and most preferably at least about 99% homologous to FIG. 2D (SEQ ID NO:5).

An isolated nucleic acid molecule encoding a BAFF-R-protein homologous to the protein of FIG. 2D can be created by introducing one or more nucleotide substitutions, additions or deletions into the nucleotide sequence of FIG. 2A (SEQ ID NO:3), FIG. 2C (SEQ ID NO:4), and FIG. 3 (SEQ ID NO:6) such that one or more amino acid substitutions, additions or deletions are introduced into the encoded protein Mutations can be introduced into FIG. 2A (SEQ ID NO:3), FIG. 2C (SEQ ID NO:4), or FIG. 3 (SEQ ID NO:6), for example, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in BAFF-R is replaced with another amino acid residue from the same side chain family. Alternatively, in another embodiment, mutations can be introduced randomly along all or part of a BAFF-R coding sequence, such as by saturation mutagenesis, and the resultant mutants can be screened for BAFF-R biological activity to identify mutants that retain activity. Following mutagenesis of any of FIG. 2A (SEQ ID NO:3), FIG. 2C (SEQ ID NO:4), and FIG. 3 (SEQ ID NO:6), the encoded protein can be expressed by any recombinant technology known in the art and the activity of the protein can be determined.

In one embodiment, a mutant BAFF-R protein can be assayed or (1) the ability to form protein:protein interactions with other BAFF-R proteins, other cell-surface proteins, or biologically active portions thereof, (2) complex formation between a mutant BAFF-IR protein and a BAFF-R ligand; (3) the ability of a mutant BAFF-R protein to bind to an intracellular target protein or biologically active portion thereof; (e.g., avidin proteins); 4) the ability to bind BAFF; or (5) the ability to specifically bind a BAFF-R protein antibody.

The invention provides specific mutants encoding a BAFF-R:Fc polypeptide designed to alleviate aggregation of expressed protein while maintaining BAFF binding activity. Such mutants, include, for example, clones encoding the amino acid sequences of JST661 (SEQ ID NO:17), JST662 (SEQ ID NO:18), JST663 (SEQ ID NO:19), JST673 (SEQ ID NO:20), JST674 (SEQ ID NO:21), JST675 (SEQ ID NO:22), JST672 (SEQ ID NO:23), JST676 (SEQ ID NO:24), JST671 (SEQ ID NO:25), JST677 (SEQ ID NO:26), and JST678 (SEQ ID NO:27). Other embodiments include mutants encoding a BAFF-R or BAFF-R:Fc polypeptide that has similar aggregation characteristics to native human BAFF-R or BAFF-R:Fc polypeptide, but also bind BAFF, including, for example, sequences comprising the amino acid sequences of JST659 (SEQ ID NO:15), JST660 (SEQ ID NO:16), JST664 (SEQ ID NO:28), JST668 (SEQ ID NO:29), JST665 (SEQ ID NO:30), JST666 (SEQ ID NO:31), and JST667 (SEQ ID NO:32). Other embodiments include mutants encoding a BAFF-R or BAFF-R:Fc polypeptide wherein conserved amino acids between human and mouse BAFF-R are changed to other conserved amino acids and wherein the binding activity of BAFF-R or BAFF-R:Fc polypeptide to BAFF is retained. In other embodiments, the mutants encode a BAFF-R or BAFF-R:Fc polypeptide having amino acids that are not conserved between human and mouse BAFF-R which have been changed to other amino acids. Preferably, at least one nonpolar amino acid is changed to a proline residue or an uncharged polar amino acid.

Antisense

Another aspect of the invention pertains to isolated antisense nucleic acid molecules that are hybridizable to or complementary to the nucleic acid molecule comprising the nucleotide sequence of FIG. 2A, C, 3 or, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire BAFF-R coding strand, or to only a portion thereof. Nucleic acid molecules encoding fragments, homologs, derivatives and analogs of a BAFF-R protein of any of FIG. 2A (SEQ ID NO:3), FIG. 2C (SEQ ID NO:4), FIG. 3 (SEQ ID NO:6) or antisense nucleic acids complementary to a BAFF-R nucleic acid sequence of any of FIG. 2A (SEQ ID NO:3), FIG. 2C (SEQ ID NO:4), FIG. 3 (SEQ ID NO:6) are additionally provided.

In one embodiment, an antisense nucleic acid molecule is antisense to a "coding region" of the coding strand of a nucleotide sequence encoding BAFF-R. The term "coding region" refers to the region of the nucleotide sequence comprising codons which are translated into amino acid residues (e.g., the protein coding region of human BAFF-R corresponds to nucleotides 13 to 568 of FIG. 2A (SEQ ID NO:3), or nucleotides 13 to 565 of FIG. 2C (SEQ ID NO:4) or nucleotides 298 to 849 of FIG. 3 (SEQ ID NO:6)). In another embodiment, the antisense nucleic acid molecule is antisense to a "noncoding region" of the coding strand of a nucleotide sequence encoding BAFF-R. The term "noncoding region" refers to 5' and 3' sequences which flank the coding region that are not translated into amino acids (i.e., also referred to as 5' and 3' untranslated regions).

Given the coding strand sequences encoding BAFF-R disclosed herein, antisense nucleic acids of the invention can be designed according to the rules of Watson and Crick or Hoogsteen base pairing. The antisense nucleic acid molecule can be complementary to the entire coding region of BAFF-R mRNA, but more preferably is an oligonucleotide that is antisense to only a portion of the coding or noncoding region of BAFF-R mRNA. For example, the antisense oligonucleotide can be complementary to the region surrounding the translation start site of BAFF-R mRNA. An antisense oligonucleotide can be for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid, (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BAFF-R protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an a-anomeric nucleic acid molecule. An a-anomeric nucleic acid molecule forms specific double-stranded hybrids with complementary RNA in which, contrary to the usual b-units, the strands run parallel to each other (Gaultier et al. (1987) *Nucl. Acids Res.* 15:6625-6641). The antisense nucleic acid molecule can also comprise a 2'-O-methylribonucleotide (Inoue et al. (1987) *Nucl. Acids Res.* 15:6131-6148) or a chimeric RNA-DNA analogue (Inoue et al. (1987) *FEBS Lett.* 215:327-330).

Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave BAFF-R mRNA transcripts to thereby inhibit translation of BAFF-R mRNA. A ribozyme having specificity for a BAFF-R-encoding nucleic acid can be designed based upon the nucleotide sequence of a BAFF-R DNA disclosed herein (i.e., SEQ ID NO:3, SEQ ID NO:4, SEQ ID NO:6). For example, a derivative of a Tetrahymena L-19 IVS RNA can be constructed in which the nucleotide sequence of the active site is complementary to the nucleotide sequence to be cleaved in a BAFF-R-encoding mRNA. See, e.g., Cech et al.

U.S. Pat. No. 4,987,071; and Cech et al. U.S. Pat. No. 5,116,742. Alternatively, BAFF-R mRNA can be used to select a catalytic RNA having a specific ribonuclease activity from a pool of RNA molecules. See, e.g., Bartel et al., (1993) *Science* 261:1411-1418.

Alternatively, BAFF-R gene expression can be inhibited by targeting nucleotide sequences complementary to the regulatory region of the BAFF-R (e.g., the BAFF-R promoter and/or enhancers) to form triple helical structures that prevent transcription of the BAFF-R gene in target cells. See generally, Helene (1991) *Anticancer Drug Des.* 6: 569-84; Helene et al. (1992) *Ann. N.Y. Acad. Sci.* 660:27-36; and Maher (1992) *Bioassays* 14:807-15.

In various embodiments, the nucleic acids of BAFF-R can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg. Med. Chem.* 4:5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neural backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) *Bioorg. Med. Chem.* 4:5-23; Perry-O'Keefe et al. (1996) *Proc. Natl. Acad. Sci. USA* 93:14670-675.

PNAs of BAFF-R can be used in therapeutic and diagnostic applications. For example, PNAs can be used as antisense or antigene agents for sequence-specific modulation of gene expression by, e.g., inducing transcription or translation arrest or inhibiting replication. PNAs of BAFF-R can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) *Bioorg. Med. Chem.* 4:5-23); or as probes or primers for DNA sequence and hybridization (Hyrup et al. (1996), *Bioorg. Med. Chem.* 4:5-23; Perry-O'Keefe (1996) *Proc. Natl. Acad. Sci. USA* 93:14670-675).

In another embodiment, PNAs of BAFF-R can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of BAFF-R can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) *Bioorg. Med. Chem.* 4:5-23). The synthesis of PNA-DNA chimeras can be performed as described in Hyrup (1996) *Bioorg. Med. Chem.* 4:5-23; and Finn et al. (1996) *Nucl. Acids Res.* 24:3357-63. For example, a DNA chain can be synthesized on a solid support using standard phosphoramidite coupling chemistry, and modified nucleoside analogs, e.g., 5'-(4-methoxytrityl) amino-5'-deoxy-thymidine phosphoramidite, can be used between the PNA and the 5' end of DNA (Mag et al. (1989) *Nucl. Acids Res.* 17:5973-88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg. Med. Chem. Lett.* 5:1119-11124.

In other embodiments, the oligonucleotide may include other appended groups such as peptides (e.g.; for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization triggered cleavage agents (see, e.g., Krol et al., (1988) *BioTechniques* 6:958-976) or intercalating agents (see, e.g., Zon, (1988) *Pharm. Res.* 5:539-549). To this end, the oligonucleotide may be conjugated to another molecule, e.g., a peptide, a hybridization triggered cross-linking agent, a transport agent, a hybridization-triggered cleavage agent, etc.

BAFF-R Polypeptides

One aspect of the invention pertains to isolated BAFF-R proteins, and biologically active portions thereof, or derivatives, fragments, analogs or homologs thereof Also provided are polypeptide fragments suitable for use as immunogens to raise anti-BAFF-R antibodies. In one embodiment, native BAFF-R proteins can be isolated from cells or tissue sources by an appropriate purification scheme using standard protein purification techniques. In another embodiment, BAFF-R proteins are produced by recombinant DNA techniques. Alternative to recombinant expression, a BAFF-R protein or pol),peptide can be synthesized chemically using standard peptide synthesis techniques.

An "isolated" or "purified" protein or biologically active portion thereof is substantially free of cellular material or other contaminating proteins from the cell or tissue source from which the BAFF-R protein is derived, or substantially free from chemical precursors or other chemicals when chemically synthesized. The language "substantially fee of cellular material" includes preparations of BAFF-R protein in which the protein is separated from cellular components of the cells from which it is isolated or recombinantly produced. In one embodiment, the language "substantially free of cellular material" includes preparations of BAFF-R protein having less than about 30% (by dry weight) of non-BAFF-R protein (also referred to herein as a "contaminating protein"), more preferably less than about 20% of non-BAFF-R protein, still more preferably less than about 10% of non-BAFF-R protein, and most preferably less than about 5% non-BAFF-R protein. When the BAFF-R protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BAFF-R protein in which the protein is separated from chemical precursors or other chemicals that are involved in the synthesis of the protein. In one embodiment, the language "substantially free of chemical precursors or other chemicals" includes preparations of BAFF-R protein having less than about 30% (by dry weight) of chemical precursors or non-BAFF-R chemicals, more preferably less than about 20% chemical precursors or non-BAFF-R chemicals, still more preferably less than about 10% chemical precursors or non-BAFF-R chemicals, and most preferably less than about 5% chemical precursors or non-BAFF-R chemicals.

Biologically active portions of a BAFF-R protein include peptides comprising ammo acid sequences sufficiently homologous to or derived from the amino acid sequence of the BAFF-R protein, e.g., the amino acid sequence shown in SEQ ID NO:5 that include fewer amino acids than the full length BAFF-R proteins, and exhibit at least one activity of a BAFF-R protein. Typically, biologically active portions comprise a domain or motif with at least one activity of the BAFF-R protein. A biologically active portion of a BAFF-R protein can be a polypeptide which is, for example, 10, 25, 50, 100 or more amino acids in length.

A biologically active portion of a BAFF-R protein of the present invention may contain at least one of the above-identified domains conserved between the BAFF-R proteins. An alternative biologically active portion of a BAFF-R protein may contain at least two of the above-identified domains. Another biologically active portion of a BAFFXR protein may contain at least three of the above-identified domains. Yet another biologically active portion of a BAFF-R protein of the present invention may contain at least four of the above-identified domains.

Moreover, other biologically active portions, in which other regions of the protein are deleted, can be prepared by recombinant techniques and evaluated for one or more of the functional activities of a native BAFF-R protein.

In an embodiment, the BAFF-R protein has an amino acid sequence shown in FIG. 2D (SEQ ID NO:5). In other embodiments, the BAFF-R protein is substantially homologous to FIG. 2D (SEQ ID NO:5) and retains the functional activity of the protein of FIG. 2D (SEQ ID NO:5), yet differs in amino acid sequence due to natural allelic variation or mutagenesis, as described in detail below. Accordingly, in another embodiment the BAFF-R protein is a protein that comprises an amino acid sequence at least about 45% homologous 40 the amino acid sequence of FIG. 2D (SEQ ID NO:5) and retains the functional activity of the BAFF-R proteins of FIG. 2D (SEQ ID NO:5).

In some embodiments, the invention includes specific mutants of BAFF-R:Fc polypeptide designed to alleviate aggregation of expressed protein while maintaining BAFF binding activity. Such mutants, include, for example, clones encoding the amino acid sequences of JST661 (SEQ ID NO:17), JST662 (SEQ ID NO:18), JST663 (SEQ ID NO:19), JST673 (SEQ ID NO:20), IST674 (SEQ ID NO0.21), JST675 (SEQ ID NO:22), JST672 (SEQ ID NO:23), JST676 (SEQ ID NO:24), JST671 (SEQ ID NO:25), JST677(SEQ ID) NO:26), and JST678 (SEQ ID NO:27). Other embodiments include mutants encoding a BAFF-R or BAFF-R:Fc polypeptide that has similar aggregation characteristics to native human BAFF-R R or BAFF-R:Fc polypeptide, but also bind BAFF, including, for example, sequences comprising the amino acid sequences of JST659 (SEQ ID NO:15), JST660 (SEQ ID NO:16), JST664 (SEQ ID NO:28), JST668 (SEQ ID NO:29), JST665 (SEQ ID NO:30), JST666 (SEQ ID NO:31), and JST667 (SEQ ID NO:32). Other embodiments include mutants encoding a BAFF-R or BAFF-R:Fc polypeptide wherein conserved amino acids between human and mouse BAFF-R are changed to other conserved amino acids and wherein the binding activity of BAFF-R or BAFF-R:Fc polypeptide to BAFF is retained. In other embodiments, the mutants encode a BAFF-R or BAFF-R:Fc polypeptide having amino acids that are not conserved between human and mouse BAFF-R which have been changed to other amino acids. Preferably, nonpolar amino acids are mutated to proline or uncharged polar amino acids.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at tat position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See Needleman and Wunsch (1970) *J. Mol. Biol.* 48:443-453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in FIG. 2A (SEQ ID NO:3), FIG. 2C (SEQ ID NO:4), FIG. 3 (SEQ ID NO:6).

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides BAFF-R chimeric or fusion proteins. As used herein, a BAFF-R "chimeric protein" or "fusion protein" comprises a BAFF-R polypeptide operatively linked to a non-BAFF-R polypeptide. A "BAFF-R polypeptide" refers to a polypeptide having an amino acid sequence corresponding to BAFF-R, whereas a "non-BAFF-R polypeptide" refers to a polypeptide having an amino acid sequence corresponding to a protein that is not substantially homologous to the BAFF-R protein, e.g., a protein that is different from the BAFF-R protein and that is derived from the same or a different organism. Within a BAFF-R fusion protein the BAFF-R polypeptide can correspond to all or a portion of a BAFF-R protein. In one embodiment, a BAFF-R fusion protein comprises at least one biologically active portion of a BAFF-R protein. In another embodiment, a BAFF-R fusion protein comprises at least two biologically active portions of a BAFF-R protein. In yet another embodiment, a BAFF-R fusion protein comprises at least three biologically active portions of a BAFF-R protein. Within the fusion protein, the term "operatively linked" is intended to indicate that the BAFF-R polypeptide and the non-BAFF-R polypeptide are fused in-frame to each other. The non-BAFF-R polypeptide can be fused to the N-terminus or C-terminus of the BAFF-R polypeptide. The non-BAFF-R polypeptide may be, for example, the Fc portion of an antibody. This may be operatively joined to either the N-terminus or the C-terminus of the BAFF-R polypeptide. Fc-target protein fusions have been described in Lo et al. (1998) *Protein Engineering* 11:495-500, and U.S. Pat. Nos. 5,541,087 and 5,726,044. The disclosures of which are herein incorporated by reference.

For example, in one embodiment a BAFF-R fusion protein comprises a BAFF-R domain operably linked to the extracellular domain of a second protein. Such fusion proteins can be further utilized in screening assays for compounds which modulate BAFF-R activity (such assays are described in detail below).

In yet another embodiment, the fusion protein is a GST-BAFF-R fusion protein in which the BAFF-R sequences are fused to the C-terminus of the GST (i.e., glutathione S-transferase) sequences. Such fusion proteins can facilitate the purification of recombinant BAFF-R.

In another embodiment, the fusion protein is a BAFF-R protein containing a heterologous signal sequence at its N-terminus. For example, since BAFF-R does not contain its own signal sequence, a heterologous signal sequence must be fused to the 5' end of the BAFF-R coding sequence for efficient secretion of the BAFF-R fusion protein. Expression and/or secretion of BAFF-R can be increased through use of different heterologous signal sequences.

In yet another embodiment, the fusion protein is a BAFF-R-immunoglobulin fusion protein in which the BAFF-R sequences comprising one or more domains are fused to sequences derived from a member of the immunoglobulin protein family. The BAFF-R-immunoglobulin fusion proteins of the invention can be incorporated into pharmaceutical compositions and administered to a subject to inhibit an interaction between a BAFF-R ligand and a BAFF-R protein on the surface of a cell, to thereby suppress BAFF-R-mediated signal transduction in vivo. The BAFF-R-immunoglobulin fusion proteins can be u to affect the bioavailability of a BAFF-R cognate ligand. Inhibition of the BAFF-R ligand/BAFF-R interaction may be useful therapeutically for both the treatment of proliferative and differentiative disorders, as well as modulating (e.g. promoting or inhibiting) cell survival. Moreover, the BAFF-R-immunoglobulin fusion proteins of the invention can be used as immunogens to produce anti-BAFF-R antibodies in a subject, to purify BAFF-R ligands, and in screening assays to identify molecules that inhibit the interaction of BAFF-R with a BAFF-R ligand.

A BAFF-R chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. Eds. CURRENT PROTOCOLS IN MOLECULAR BIOLOGY, John Wiley & Sons, 1992). Moreover, many expression vectors are commercially available that already encode a fusion moiety (e.g., a GST polypeptide). A BAFF-R-encoding nucleic acid can be cloned into such an expression vector such that the fusion moiety is linked in-frame to the BAFF-R protein.

In a preferred embodiment, the BAFF-R fusion is provided by the nucleic acid (SEQ ID NO:11) and amino acid (SEQ ID NO:12) sequences of FIG. 9.

BAFF-R Agonists and Antagonists

The present invention also pertains to variants of the BAFF-R proteins that function as either BAFF-R agonists (mimetics) or as BAFF-R antagonists. Variants of the BAFF-R protein can be generated by mutagenesis, e.g., discrete point mutation or truncation of the BAFF-R protein. An agonist of the BAFF-R protein can retain substantially the same, or a subset of, the biological activities of the naturally occurring form of the BAFF-R protein An antagonist of the BAFF-R protein can inhibit one or more of the activities of the naturally occurring form of the BAFF-R protein by, for example, competitively binding to a downstream or upstream member of a cellular signaling cascade which includes the BAFF-R protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the BAFF-R proteins.

Variants of the BAFF-R protein that function as either BAFF-R agonists (mimetics) or as BAFF-R antagonists can be identified by screening combinatorial libraries of mutants, e.g., truncation mutants, of the BAFF-R protein for BAFF-R protein agonist or antagonist activity. In one embodiment, a variegated library of BAFF-R variants is generated by combinatorial mutagenesis at the nucleic acid level and is encoded by a variegated gene library. A variegated library of BAFF-R variants can be produced by, for example, enzymatically ligating a mixture of synthetic oligonucleotides into gene sequences such that a degenerate set of potential BAFF-R sequences is expressible as individual polypeptides, or alternatively, as a set of larger fusion proteins (e.g., for phage display) containing the set of BAFF-R sequences therein. There are a variety of methods which can be used to produce libraries of potential BAFF-R variants from a degenerate oligonucleotide sequence. Chemical synthesis of a degenerate gene sequence can be performed in an automatic DNA synthesize, and the synthetic gene then ligated into an appropriate expression vector. Use of a degenerate set of genes allows for the provision, in one mixture, of all of the sequences encoding the desired set of potential BAFF-R sequences. Methods for synthesizing degenerate oligonucleotides are known in the art (see, e.g., Narang (1983) *Tetrahedron* 39:3; Itakura et al. (1984) *Ann. Rev. Biochem.* 53:323; Itakura et al. (1977) *Science* 198:1056-1063; Ike et al. (1983) *Nucl. Acids Res.* 11:477-488.

Polypeptide Libraries

In addition, libraries of fragments of the BAFF-R protein coding sequence can be used to generate a variegated population of BAFF-R fragments for screening and subsequent selection of variants of a BAFF-R protein. In one embodiment, a library of coding sequence fragments can be generated by treating a double stranded PCR fragment of a BAFF-R coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the BAFF-R protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of BAFF-R proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify BAFF-R variants (Arkin and Yourvan (1992) *Proc. Natl. Acad. Sci. USA* 89:7811-7815; Delgrave et al. (1993) *Protein Engineering* 6:327-331).

Anti-BAFF-R Antibodies

An isolated BAFF-R protein, or a portion or fragment thereof, can be used as an immunogen to generate antibodies that bind BAFF-R using standard techniques for polyclonal and monoclonal antibody preparation. The full-length BAFF-R protein can be used or, alternatively, the invention provides antigenic peptide fragments of BAFF-R for use as immunogens. The antigenic peptide of BAFF-R comprises at least 8 amino acid residues of the amino acid sequence shown in FIG. 2D (SEQ ID NO:5) and encompasses an epitope of BAFF-R such that an antibody raised against the peptide forms a specific immune complex with BAFF-R. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of BAFF-R that are located on the surface of the protein, e.g., hydrophilic regions.

As disclosed herein, BAFF-R protein sequence of FIG. 2D (SEQ ID NO:5), or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as BAFF-R. Such antibodies include, but are not limited to, polyclonal, monoclonal, chimeric, single chain, Fab and Fab')₂ fragments, and an Fab expression library. In a specific embodiment, antibodies to human BAFF-R proteins are disclosed. Various procedures known within the art may be used for the production of polyclonal or monoclonal antibodies to a BAFF-R protein sequence of FIG. 2D (SEQ ID NO:5) or derivative, fragment, analog or homolog thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed BAFF-R protein or a chemically synthesized BAFF-R polypeptide. The preparation can further include an adjuvant. Various adjuvants used to increase the immunological response include, but are not limited to, Freund's (complete and incomplete), mineral gels (e.g. aluminum hydroxide), surface active substances (e.g., lysolecithin, pluronic polyols, polyanions, peptides, oil emulsions, dinitrophenol, etc.), human adjuvants such as Bacille Calmette-Guerin-MCG) and *Corynebacterium parvum*, or similar immunostimulatory agents. If desired, the antibody molecules directed against BAFF-R can be isolated from the mammal (e.g., from the blood) and further purified by well-known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of BAFF-R. A monoclonal antibody composition thus typically displays a single binding affinity for a particular BAFF-protein with which it immunoreacts. For preparation of monoclonal antibodies directed towards a particular BAFF-R protein, or derivatives, fragments, analogs or homologs thereof, any technique that provides for the production of antibody molecules by continuous cell line culture may be utilized. Such techniques include, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96). Human monoclonal antibodies may be utilized in the practice of the present invention and may be produced by using human hybridomas (see Cote et al. (1983) *Proc. Natl. Acad. Sci. USA* 80:2026-2030) or by transforming human B-cells with Epstein Barr Virus in vitro (see Cole et al. in MONOCLONAL ANTIBODIES AND CANCER THERAPY, Alan R. Liss, Inc., 1985 pp. 77-96).

According to the invention, techniques can be adapted for the production of single-chain antibodies specific to a BAFF-R protein (see e.g., U.S. Pat. No. 4,946,778). In addition, methods can be adapted for the construction of Fab expression libraries (see e.g., Huse et al. (1989) *Science* 246: 1275-1281) to allow rapid and effective identification of monoclonal Fab fragments with the desired specificity for a BAFF-R protein or derivatives, fragments, analogs or homologs thereof. Non-human antibodies can be "humanized" by techniques well known in the art. See e.g., U.S. Pat. No. 5,225,539. Antibody fragments that contain the idiotypes to a BAFF-R protein may be produced by techniques known in he art including, but not limited to: (i) an F(ab')₂ fragment produced by pepsin digestion of an antibody molecule; (ii) an Fab fragment generated by reducing the disulfide bridges of an F(ab')₂ fragment; (iii) an Fab fragment generated by the treatment of the antibody molecule with papain and a reducing agent and (iv) Fv fragments.

Additionally, recombinant anti-BAFF-R antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314: 446-449; Shaw et al. (1988) *J. Natl. Cancer Inst.* 80:1553-1559); Morrison (1985) *Science* 229:1202-1207; Oi et al. (1986) *Biotechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141: 4053-4060.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a BAFF-R protein is facilitated by generation of hybridomas that bind to the fragment of a BAFF-R protein possessing such a domain. Antibodies that are specific for one or more domains within a BAFF-R protein, e.g., domains spanning the above-identified conserved regions of BAFF-R family proteins, or derivatives, fragments, analogs or homologs thereof, are also provided herein.

Anti-BAFF-R antibodies may be used in methods known within the art relating to the localization and/or quantitation of a BAFF-R protein (e.g. for use in measuring levels of the BAFF-R protein within appropriate physiological samples, for use in diagnostic methods, for use in imaging the protein, and the like). In a given embodiment, antibodies for BAFF-R proteins, or derivatives, fragments, analogs or homologs thereof, that contain the antibody derived binding domain, are utilized as pharmacologically-active compounds (hereinafter "Therapeutics").

An anti-BAFF-R antibody (e.g., monoclonal antibody) can be used to isolate BAFF-R by standard techniques, such as affinity chromatography or immunoprecipitation. An anti-BAFF-R antibody can facilitate the purification of natural BAFF-R from cells and of recombinantly produced BAFF-R expressed in host cells. Moreover, an anti-BAFF-R antibody can be used to detect BAFF-R protein (e.g., in a cellular lysate or cell supernatant) in order to evaluate the abundance and pattern of expression of the BAFF-R protein. Anti-BAFF-R antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, B-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

BAFF-R Recombinant Expression Vectors and Host Cells

Another aspect of the invention pertains to vectors, preferably expression vectors, containing a nucleic acid encoding BAFF-R protein, or derivatives, fragments, analogs or homologs thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel "Gene Expression Technology" METHODS IN ENZYMOLOGY 185, Academic Press, San Diego, Calif., 1990. Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., BAFF-R proteins, mutant forms of BAFF-R, fusion proteins, etc.).

The recombinant expression vectors of the invention can be designed for expression of BAFF-R in prokaryotic or eukaryotic cells. For example, BAFF-R can be expressed in bacterial cells such as *Escherichia coli*, insect cells (using baculovirus expression vectors) yeast cells or mammalian cells. Suitable host cells are discussed further in Goeddel, "Gene Expression Technology" METHODS IN ENZYMOLOGY 185, Academic Press, San Diego, Calif., 1990. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301-315) and pET 11d (Studier et al., "Gene Expression Technology" METHODS IN ENZYMOLOGY 185, Academic Press, San Diego, Calif., 1990, pp. 60-89).

One strategy to maximize recombinant protein expression in E. coli is to express the protein in a host bacterium with an impaired capacity to proteolytically cleave the recombinant protein. See, Gottesman, "Gene Expression Technology" METHODS IN ENZYMOLOGY 185, Academic Press, San Diego, Calif., 1990, pp. 119-128. Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

In another embodiment, the BAFF-R expression vector is a yeast expression vector. Examples of vectors for expression in yeast (e.g., Saccharomyces cerivisae) include pYepSec1 (Baldari, et al., (1987) EMBO J. 6:229-234), pMFa (Kujan and Herskowitz, (1982) Cell 30:933-943), pJRY88 (Schultz et al. (1987) Gene 54:113-123), pYES2 (Invitrogen Corporation, San Diego, Calif.), and for P. pastoris include pPIC family of vectors (Invitrogen Corp, San Diego, Calif.).

Alternatively, BAFF-R can be expressed in insect cells using baculovirus expression vectors. Baculovirus vectors available for expression of proteins in cultured insect cells (e.g., SF9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840-842) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2ND ED., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter, U.S. Pat. No. 4,873,316 and European Application Publication No. 264,166). Developmentally-regulated promoters are also encompassed, e.g., the murine box promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation That is, the DNA molecule is operatively linked to a regulatory sequence in a manner that allows for expression (by transcription of the DNA molecule) of an RNA molecule that is antisense to BAFF-R mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) "Antisense RNA as a molecular tool for genetic analysis," Reviews—Trends in Genetics, 1(1).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, BAFF-R protein can be expressed in bacterial cells such as E. coli, insect cells, yeast or mammalian cells such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terns "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. MOLECULAR CLONING: A LABORATORY MANUAL 2ND ED., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that coffer resistance to drugs, such as G418, hygromycin and methotrexate. Nucleic acid encoding a selectable marker can be introduced into a host cell on the same vector as that encoding BAFF-R or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) BAFF-R protein. Accordingly, the invention further provides methods for producing BAFF-R protein using the host cells of the invention. In one embodiment, the method comprises culturing the host cell of invention (into which a recombinant expression vector encoding BAFF-R has been introduced) in a suitable medium such that BAFF-R protein is produced. In another embodiment, the method further comprises isolating BAFF-R from the medium or the host cell.

Transgenic Animals

The host cells of the invention can also be used to produce nonhuman transgenic animals. For example, in one embodiment, a host cell of the invention is a fertilized oocyte or an embryonic stem cell into which BAFF-R-coding sequences have been introduced. Such host cells can then be used to create non-human transgenic animals in which exogenous BAFF-R sequences have been introduced into their genome or homologous recombinant animals in which endogenous BAFF-R sequences have been altered. Such animals are useful for studying the function and/or activity of BAFF-R and for identifying and/or evaluating modulators of BAFF-R activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BAFF-R gene has been altered by homologous recombination between the endogenous gene and an exogenous DNA molecule introduced into a cell of the animal, e.g., an embryonic cell of the animal, prior to development of the animal.

A transgenic animal of the invention can be created by introducing BAFF-R-encoding nucleic acid into the male pronuclei of a fertilized oocyte, e.g. by microinjection, retroviral infection, and allowing the oocyte to develop in a pseudopregnant female foster animal. The human BAFF-R DNA sequence of FIG. 2A (SEQ ID NO:3), FIG. 2C (SEQ ID NO:4), FIG. 3 (SEQ ID NO:6) can be introduced as a transgene into the genome of a non-human animal. Alternatively, a nonhuman homologue of the human BAFF-R gene, such as a mouse BAFF-R gene (FIG. 4A) (SEQ ID NO:8), can be isolated based on hybridization to the human BAFF-R cDNA (described further above) and used as a transgene. Intronic sequences and polyadenylation signals can also be included in the transgene to increase the efficiency of expression of the transgene. A tissue-specific regulatory sequence(s) can be operably lied to the BAFF-R transgene to direct expression of BAFF-R protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan in MANIPULATING THE MOUSE EMBRYO, Cold Spring Harbor Laboratory Press, Cold Spring Harbor, N.Y., 1986. Similar methods are used for production of other transgenic animals. A transgenic founder animal can be identified based upon the presence of the BAFF-R transgene in its genome and/or expression of BAFF-R mRNA in tissues or cells of the animals. A transgenic founder animal can then be used to breed additional animals carrying the transgene. Moreover, transgenic animals carrying a transgene encoding BAFF-R can further be bred to other transgenic animals carrying other transgenes.

To create a homologous recombinant animal, a vector is prepared which contains at least a portion of a BAFF-R gene into which a deletion, addition or substitution has been introduced to thereby alter, e.g., functionally disrupt, the BAFF-R gene. The BAFF-R gene can be a human gene (e.g., FIG. 2A (SEQ ID NO:3), FIG. 2C (SEQ ID NO:4), FIG. 3 (SEQ ID NO:6)), but more preferably, is a non-human homologue of a human BAFF-R gene. For example, a mouse homologue (FIG. 4a) of human BAFF-R gene of FIG. 2A (SEQ ID NO:3), FIG. 2C (SEQ ID NO:4), FIG. 3 (SEQ ID NO:6) can be used to construct a homologous recombination vector suitable for altering an endogenous BAFF-R gene in the mouse genome. In one embodiment, the vector is designed such that, upon homologous recombination, the endogenous BAFF-R gene is functionally disrupted (i.e., no longer encodes a functional protein; also referred to as a "knock out" vector).

Alternatively, the vector can be designed such that, upon homologous recombination, the endogenous BAFF-R gene is mutated or otherwise altered but still encodes functional protein (e.g., the upstream regulatory region can be altered to thereby alter the expression of the endogenous BAFF-R protein). In the homologous recombination vector, the altered portion of the BAFF-R gene is flanked at its 5' and 3' ends by additional nucleic acid of the BAFF-R gene to allow for homologous recombination to occur between the exogenous BAFF-R gene carried by the vector and an endogenous BAFF-R gene in an embryonic stem cell. The additional flanking BAFF-R nucleic acid is of sufficient length for successful homologous recombination with the endogenous gene. Typically, several kilobases of flanking DNA (both at the 5' and 3' ends) are included in the vector. See e.g., Thomas et al. (1987) *Cell* 51:503 for a description of homologous recombination vectors. The vector is introduced into an embryonic stem cell line (e.g., by electroporation) and cells in which the introduced BAFF-R gene has homologously recombined with the endogenous BAFF-R gene are selected (see e.g., Li et al. (1992) *Cell* 69:915).

The selected cells are then injected into a blastocyst of an animal (e.g., a mouse) to form aggregation chimeras. See e.g., Bradley, in TERATOCARCINOMAS AND EMBRYONIC STEM CELLS: A PRACTICAL APPROACH, Robertson, Ed. IRL, Oxford, 1987, pp. 113-152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr. Opin. Biotechnol.* 2:823-829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *S. cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810-813. In brief, a cell, e.g., a somatic cell, from the transgenic animal can be isolated and induced to exit the growth cycle and enter $G_0$ phase. The quiescent cell can then be fused, e.g. through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The BAFF-R nucleic acid molecules, BAFF-R proteins, and anti-BAFF-R antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a BAFF-R protein or anti-BAFF-R antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, erg., as described in U.S. Pat. Nos. 5,703,055. Delivery can thus also include, e.g., intravenous injection, local administration (see U.S. Pat. No. 5,328,470) or stereotactic injection (see e.g., Chen et al. (1994) *Proc. Natl. Acad. Sci.* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration, Uses and Methods of the Invention The nucleic acid molecules, proteins, protein homologues, and antibodies described herein can be used in one or more of the following methods: (a) screening assays; (b) detection assays (e.g., chromosomal mapping, tissue typing, forensic biology), (c) predictive medicine (e.g., diagnostic assays, prognostic assays, monitoring clinical trials, and pharmacogenomics); and (d) methods of treatment (e.g., therapeutic and prophylactic). As described herein, in one embodiment, a BAFF-R protein of the invention has the ability to bind BAFF.

The isolated nucleic acid molecules of the invention can be used to express BAFF-R protein (e.g., via a recombinant expression vector in a host cell in gene therapy applications), to detect BAFF-R mRNA (e.g., in a biological sample) or a genetic lesion in a BAFF-R gene, and to modulate BAFF and/or BAFF-R activity, as described further below. In addition, the BAFF-R proteins can be used to screen drugs or compounds that modulate the BAFF-R activity or expression as well as to treat disorders characterized by insufficient or excessive production of BAFF and/or BAFF-R protein; or production of BAFF-R protein forms that have decreased or aberrant activity compared to BAFF-R wild type protein. In addition, the anti-BAFF-R antibodies of the invention can be used to detect and isolate BAFF-R proteins and modulate BAFF and/or BAFF-R activity.

This invention further pertains to novel agents identified by the above-described screening assays and uses thereof for treatments as described herein.

Screening Assays

The invention provides a method (also referred to herein as a "screening assay") for identifying modulators, i.e., candidate or test compounds or agents (e.g. peptides, peptidomimetics, small molecules or other drugs) that bind to BAFF-R proteins or have a stimulatory or inhibitory effect on, for example, BAFF-R expression or BAFF-R activity.

In one embodiment, the invention provides assays for screening candidate or test compounds which bind to or modulate the activity of a BAFF-R protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145-167).

Examples of methods for the synthesis of molecular libraries can be found in the art, for example in: DeWitt et al. (1993) *Proc. Natl. Acad. Sci. USA* 90:6909-6013; Erb et al. (1994) *Proc. Natl. Acad. Sci. USA* 91:11422-11426; Zuckermann et al. (1994) *J. Med. Chem.* 37:2678-2685; Cho et al. (1993) *Science* 261:1303; Carrell et al. (1994) *Angew Chem. Int. Ed. Engl.* 33:2059; Carell et al. (1994) *Angew Chem. Int. Ed. Engl.* 33:2061; and Gallop et al. (1994) *J. Med. Chem.* 37:1233-1251.

Libraries of compounds may be presented in solution (e.g., Houghten (1992) *Biotechniques* 13:412421), or on beads (Lam (1991) *Nature* 354:82-84), on chips (Fodor (1993) *Nature* 364:555-556), bacteria (Ladner U.S. Pat. No. 5,223,409), spores (Ladner U.S. Pat. No. 5,223,409), plasmids (Cull et al. (1992) *Proc. Natl. Acad. Sci. USA* 89:1865-1869) or on phage (Scott and Smith (1990) *Science* 249:386-390; Devlin (1990) *Science* 249:404-406; Cwirla et al. (1990) *Proc. Natl. Acad. Sci. USA* 87:6378-6382; Felici (1991) *J. Mol. Biol.* 222:301-310; Ladner U.S. Pat. No. 5,223,409).

In one embodiment, an assay is a cell-based assay in which a cell which expresses a membrane-bound form of BAFF-R protein or a biologically active portion thereof, on the cell surface is contacted with a test compound and the ability of the test compound to bind to a BAFF-R protein determined. The cell, for example, can of mammalian origin or a yeast cell. Determining the ability of the test compound to bind to the BAFF-R protein can be accomplished, for example, by coupling the test compound with a radioisotope or enzymatic label such that binding of the test compound to the BAFF-R protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one-embodiment, the assay comprises contacting a cell which expresses a membrane-bound form of BAFF-R protein, or a biologically active portion thereof, on the cell surface with a known compound which binds BAFF-R to form an assay mixture, contacting the assay mixture with a test compound, and determining the ability of the test compound to interact with a BAFF-R protein, wherein determining the ability of the test compound to interact with a BAFF-R protein comprises determining the ability of the test compound to preferentially bind to BAFF-R or a biologically active portion thereof as compared to the known compound.

In another embodiment, an assay is a cell-based assay comprising contacting a cell expressing a membrane-bound form of BAFF-R protein, or a biologically active portion thereof, on the cell surface with a test compound and determining the ability of the test compound to modulate (e.g., stimulate or inhibit) the activity of the BAFF-R protein or biologically active portion thereof. Determining the ability of the test compound to modulate the activity of BAFF-R or a biologically active portion thereof can be accomplished, for example, by determining the ability of the BAFF-R protein to bind to or interact with a BAFF-R target molecule. As used herein, a "target molecule" is a molecule with which a BAFF-R protein binds or interacts in nature, for example, a molecule on the surface of a cell which expresses a BAFF-R protein, a molecule on the surface of a second cell, a molecule in the extracellular milieu, a molecule associated with the internal surface of a cell membrane or a cytoplasmic molecule. A BAFF-R target molecule can be a non-BAFF-R molecule or a BAFF-R protein or polypeptide of the present invention. In one embodiment, a BAFF-R target molecule is a component of a signal transduction pathway that facilitates transduction of an extracellular signal (e.g., a signal generated by binding of a compound to a membrane-bound BAFF-R molecule) through the cell membrane and into the cell. The target, for example, can be a second intercellular protein that has catalytic activity or a protein that facilitates the association of downstream signaling molecules with BAFF-R.

Determining the ability of the BAFF-R protein to bind to or interact with a BAFF-R target molecule can be accomplished by one of the methods described above for determining direct binding. In one embodiment, determining the ability of the BAFF-R protein to bind to or interact with a BAFF-R target molecule can be accomplished by determining the activity of the target molecule. For example, the activity of the target molecule can be determined by detecting induction of a cellular second messenger of the target (i.e. intracellular $Ca^{2+}$, diacylglycerol, IP3, etc.), detecting catalytic/enzymatic activity of the target an appropriate substrate, detecting the induction of a reporter gene (comprising a BAFF-R-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a BAFF-R protein or biologically active portion thereof with a test compound and determining the ability of the test compound to bind to the BAFF-R protein or biologically active portion thereof. Binding of the test compound to the BAFF-R protein can be determined either directly or indirectly as described above. In one embodiment, the assay comprises contacting the BAFF-R protein or biologically active portion thereof with a known compound which binds BAFF-R to form an assay mixture, contacting the assay mixture with a test compound, and determining the ability of the test compound to interact with a BAFF-R protein, wherein determining the ability of the test compound to interact with a BAFF-R protein comprises determining the ability of the test compound to preferentially bind to BAFF-R or biologically active portion thereof as compared to the known compound.

In another embodiment, an assay is a cell-free assay comprising contacting BAFF-R protein or biologically active portion thereof with a test compound and determining the ability of the test compound to modulate (e.g., stimulate or inhibit) the activity of the BAFF-R protein or biologically active portion thereof. Determining the ability of the test compound to modulate the activity of BAFF-R can be accomplished, for example, by determining the ability of the BAFF-R protein to bind to a BAFF-R target molecule by one of the methods described above for determining direct binding. In an alternative embodiment, determining the ability of the test compound to modulate the activity of BAFF-R can be accomplished by determining the ability of the BAFF-R protein further modulate a BAFF-R target molecule. For example, the catalytic/enzymatic activity of the target molecule on an appropriate substrate can be determined as previously described.

In yet another embodiment, the cell-free assay comprises contacting the BAFF-R protein or biologically active portion thereof with a known compound which binds BAFF-R to form an assay mixture, contacting the assay mixture with a test compound, and determining the ability of the test compound to interact with a BAFF-R protein, wherein determining the ability of the test compound to interact with a BAFF-R protein comprises determining the ability of the BAFF-R protein to preferentially bind to or modulate the activity of a BAFF-R target molecule.

The cell-free assays of the present invention are amenable to use of both the soluble form or the membrane-bound form of BAFF-R. In the case of cell-free assays comprising the membrane-bound form of BAFF-R, it may be desirable to utilize a solubilizing agent such that the membrane-bound form of BAFF-R is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-(3-cholamidopropyl)dimethylamminiol-1-propane sulfonate (CHAPS), 3-(3-cholamidopropyl)dimethylamminiol-2-hydroxy-1-propane sulfonate (CHAPSO), or N-dodecyl-N,N-dimethyl-3-ammonio-1-propane sulfonate.

In more than one embodiment of the above assay methods of the present invention, it may be desirable to immobilize either BAFF-R or its target molecule to facilitate separation of complexed from uncomplexed forms of one or both of the proteins, as well as to accommodate automation of the assay. Binding of a test compound to BAFF-R, or interaction of BAFF-R with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-BAFF-R fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or BAFF-R protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of BAFF-R binding or activity determined using standard techniques.

Other techniques for immobilizing proteins on matrices can also be used in the screening assays of the invention. For example, either BAFF-R or its target molecule can be immobilized utilizing conjugation of biotin and streptavidin. Biotinylated BAFF-R or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with BAFF-R or target molecules, but which do not interfere with binding of the BAFF-R protein to its target molecule, can be derivatized to the wells of the plate, and unbound target or BAFF-R trapped in the wells by antibody conjugation. Methods for detecting such complexes, in addition to those described above for the GST-immobilized complexes, include immunodetection of complexes using antibodies reactive with the BAFF-R or target molecule, as well as enzyme-linked assays that rely on detecting an enzymatic activity associated with the BAFF-R or target molecule.

In another embodiment, modulators of BAFF-R expression are identified in a method wherein a cell is contacted with a candidate compound and the expression of BAFF-R mRNA or protein in the cell is determined. The level of expression of BAFF-R mRNA or protein in the presence of the candidate compound is compared to the level of expression of BAFF-R mRNA or protein in the absence of the candidate compound. The candidate compound can then be identified as a modulator of BAFF-R expression based on this comparison. For example, when expression of BAFF-R mRNA or protein is greater (statistically significantly greater) in the presence of the candidate compound than in its absence, the candidate compound is identified as a stimulator of BAFF-R mRNA or protein expression. Alternatively, when expression of BAFF-R mRNA or protein is less (statistically significantly less) in the presence of the candidate compound than in its absence, the candidate compound is identified as an inhibitor of BAFF-R mRNA or protein expression. The level of BAFF-R mRNA or protein expression in the cells can be determined by methods described herein for detecting BAFF-R mRNA or protein.

In yet another aspect of the invention, the BAFF-R proteins can be used as "bait proteins" in a two-hybrid assay or three hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO 94/10300), to identify other proteins that bind to or interact with BAFF-R ("BAFF-R-binding proteins" or "BAFF-R-bp") and modulate BAFF-R activity. Such BAFF-R-binding proteins are also likely to be involved in the propagation of signals-by the BAFF-R proteins as, for example, upstream or downstream elements of the BAFF-R pathway.

The two-hybrid system is based on the modular nature of most transcription factors, which consist of separable DNA-binding and activation domains. Briefly, the assay utilizes two different DNA constructs. In one construct, the gene that codes for BAFF-R is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in viva, forming a BAFF-R-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with BAFF-R.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the BAFF-R, sequences, described herein, can be used to map the location of the BAFF-R genes, respectively, on a chromosome. The mapping of the BAFF-R sequences to chromosomes is an important first step in correlating these sequences with genes associated with disease.

Briefly, BAFF-R genes can be mapped to chromosomes by preparing PCR primers (preferably 15-25 bp in length) from the BAFF-R sequences. Computer analysis of the BAFF-R, sequences can be used to rapidly select primers that do not span more than one exon in the genomic DNA, thus complicating the amplification process. These primers can then be used for PCR screening of somatic cell hybrids containing individual chromosomes of a given species. Only those hybrids containing the species-specific gene corresponding to the BAFF-R sequences will yield an amplified fragment.

PCR mapping of somatic cell hybrids is a rapid procedure for assigning a particular sequence to a particular chromosome. Three or more sequences can be assigned per day using a single thermal cycler. Using the BAFF-R sequences to design oligonucleotide primers, sublocalization can be achieved with panels of fragments from specific chromosomes.

Fluorescence in situ hybridization (FISH) of a DNA sequence to a metaphase chromosomal spread can farther be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with (Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see Verma et al. HUMAN CHROMOSOMES: A MANUAL OF BASIC TECHNIQUES, Pergamon Press, N.Y., 1988.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data Such data are found, for example, in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, for example, Egeland et al (1987) *Nature*, 325:783-787.

Moreover, differences in the DNA sequences between individuals affected and unaffected with a disease associated with the BAFF-R gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The BAFF-R sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the BAFF-R sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The BAFF-R sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of FIG. 1A (SEQ ID NO:1), FIG. 1B (SEQ ID NO:2), FIG. 2A (SEQ ID NO:3), FIG. 2B (SEQ ID NO:4), FIG. 3 (SEQ ID NO:6) can comfortably provide positive individual identification with a panel of perhaps 10 to 1,000 primers that each yield a noncoding amplified sequence of 100 bases. If predicted coding sequences, such as those in FIG. 1A (SEQ ID NO:1), FIG. 1B (SEQ ID NO:2), FIG. 2A (SEQ ID NO:3), FIG. 2B (SEQ ID NO:4), FIG. 3 (SEQ ID NO:6) are used, a more appropriate number of primers for positive individual identification would be 500-2,000.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining BAFF-R protein and/or nucleic acid expression as well as BAFF-R activity, in the context of a biological sample (e.g., blood, serum, cells, tissue) to thereby determine whether an individual is afflicted with a disease or disorder, or is at risk of developing a disorder, associated with aberrant BAFF-R expression or activity. The invention also provides for prognostic (or predictive) assays for determining whether an individual is at risk of developing a disorder associated with BAFF-R protein, nucleic acid expression or activity. For example, mutations in a BAFF-R gene can be assayed in a biological sample. Such assays can be used for prognostic or predictive purpose to thereby prophylactically treat an individual prior to the onset of a disorder characterized by or associated with BAFF-R protein, nucleic acid expression or activity.

Another aspect of the invention provides methods for determining BAFF-R protein, nucleic acid expression or BAFF-R activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of BAFF-R in clinical trials.

These and other agents are described in further detail in the following sections.

Diagnostic Assays

An exemplary method for detecting the presence or absence of BAFF-R in a biological sample involves obtaining a biological sample from a test subject and contacting the biological sample with a compound or an agent capable of detecting BAFF-R protein or nucleic acid (e.g., mRNA, genomic DNA) that encodes BAFF-R protein such that the presence of BAFF-R is detected in the biological sample. An agent for detecting BAFF-R mRNA or genomic DNA is a labeled nucleic acid probe capable of hybridizing to BAFF-R mRNA or genomic DNA. The nucleic acid probe can be, for example, a full-length BAFF-R nucleic acid, such as the nucleic acids of any of FIG. 1A (SEQ ID NO:1), FIG. 1B (SEQ ID NO:2), FIG. 2A (SEQ ID NO:3), FIG. 2B (SEQ ID NO:4), FIG. 3 (SEQ ID NO:6) or a portion thereof, such as an oligonucleotide of at least 15, 30, 50, 100, 250 or 500 nucleotides in length and sufficient to specifically hybridize under stringent conditions to BAFF-R mRNA or genomic DNA. Other suitable probes for use in the diagnostic assays of the invention are described herein.

An agent for detecting BAFF-R protein is an antibody capable of binding to BAFF-R protein, preferably an antibody with a detectable label. Antibodies can be polyclonal, or more preferably, monoclonal. An intact antibody, or a fragment thereof (e.g., Fab or F(ab')$_2$) can be used. The tern "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, sells and biological fluids isolated from a subject, as well as tissues, cells and fluids present within a subject. That is, the detection method of the invention can be used to detect BAFF-R mRNA, protein, or genomic DNA in a biological sample in vitro as well as in vivo. For example, in vitro techniques for detection of BAFF-R mRNA include Northern hybridizations and in situ hybridizations. In vitro techniques for detection of BAFF-R protein include enzyme linked immunosorbent assays (ELISAs), Western blots, immunoprecipitations and immunofluorescence. In vitro techniques for detection of BAFF-R genomic DNA include Southern hybridizations. Furthermore, in vivo techniques for detection of BAFF-R protein include introducing into a subject a labeled anti-BAFF-R antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting BAFF-R protein, mRNA, or genomic DNA, such that the presence of BAFF-R protein, mRNA or genomic DNA is detected in the biological sample, and comparing the presence of BAFF-R protein, mRNA or genomic DNA in the control sample with the presence of BAFF-R protein, mRNA or genomic DNA in the test sample.

The invention also encompasses kits for detecting the presence of BAFF-R in a biological sample. For example, the kit can comprise: a labeled compound or agent capable of detecting BAFF-R protein or mRNA in a biological sample; means for determining the amount of BAFF-R in the sample; and means for comparing the amount of BAFF-R in the sample with a standard. The compound or agent can be packaged in a suitable container. The kit can further comprise instructions for using the kit to detect BAFF-R protein or nucleic acid.

Prognostic Assays

The diagnostic methods described herein can furthermore be utilized to identify subjects having or at risk of developing a disease or disorder associated with aberrant BAFF-R expression or activity. For example, the assays described herein, such as the preceding diagnostic assays or the following assays, can be utilized to identify a subject having or at risk of developing a disorder associated with BAFF-R protein, nucleic acid expression or activity in, e.g., autoimmune conditions such as autoimmune hemolytic anemia and systemic lupus erythematosus. Alternatively, the prognostic assays can be utilized to identify a subject having or at risk for developing a disease or disorder. Thus, the present invention provides a method for identifying a disease or disorder associated with aberrant BAFF-R expression or activity in which a test sample is obtained from a subject and BAFF-R protein or nucleic acid (e.g., mRNA, genomic DNA) is detected, wherein the presence of BAFF-R protein or nucleic acid is diagnostic for a subject having or at risk of developing a disease or disorder associated with aberrant BAFF-R expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant BAFF-R expression or activity. For example, such methods can be used to determine whether a subject can be effectively treated with an agent for a disorder. Thus, the present invention provides methods for determining whether a subject can be effectively treated with an agent for a disorder associated with aberrant BAFF-R expression or activity in which a test sample is obtained and BAFF-R protein or nucleic acid is detected (e.g., wherein the presence of BAFF-R protein or nucleic acid is diagnostic for a subject that can be administered the agent to treat a disorder associated with aberrant BAFF-R expression or activity.)

The methods of the invention can also be used to detect genetic lesions in a BAFF-R gene, thereby determining if a subject with the lesioned gene is at risk for, or suffers from, a tumorigenic or autoimmune disorder. In various embodiments, the methods include detecting, in a sample of cells from the subject, the presence or absence of a genetic lesion characterized by at least one of an alteration affecting the integrity of a gene encoding a BAFF-R-protein, or the mis-expression of the BAFF-R gene. For example, such genetic lesions can be detected by ascertaining the existence of at least one of (1) a deletion of one or more nucleotides from a BAFF-R gene; (2) an addition of one or more nucleotides to a BAFF-R gene; (3) a substitution of one or more nucleotides of a BAFF-R gene, (4) a chromosomal rearrangement of a BAFF-R gene; (5) an alteration in the level of a messenger RNA transcript of a BAFF-R gene, (6) aberrant modification of a BAFF-R gene, such as of the methylation pattern of the genomic DNA, (7) the presence of a non-wild type splicing pattern of a messenger RNA transcript of a BAFF-R gene, (8) a non-wild type level of a BAFF-R-protein, (9) allelic loss of a BAFF-R gene, and (10) inappropriate post-translational modification of a BAFF-R-protein. As described herein, there are a large number of assay techniques known in the art which can be used for detecting lesions in a BAFF-R gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the BAFF-R-gene (see Abravaya et al. (1995) *Nucl. Acids Res.* 23:675-682). This method can include the steps of collecting a sample of cells from a patient, isolating nucleic acid (e.g., genomic, mRNA or both) from the cells of the sample, contacting the nucleic acid sample with one or more primers that specifically hybridize to a BAFF-R gene under conditions such that hybridization and amplification of the BAFF-R gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., (1990) *Proc. Natl. Acad. Sci. USA* 87:1874-1878), transcriptional amplification system (Kwoh, et al. (1989) *Proc. Natl. Acad. Sci. USA* 86:1173-1177), Q-Beta Replicase (Lizardi et al. (1988) *BioTechnology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a BAFF-R gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in BAFF-R can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Med.* 2:753-759). For example, genetic mutations in BAFF-R can be identified in two-dimensional arrays containing light-generated DNA probes as described in Cronin et al. (1996) *Human Mutation* 7:244-255. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the BAFF-R gene and detect mutations by comparing the sequence of the sample BAFF-R with the corresponding wild-type (control) sequence. Examples of sequencing reactions include those based on techniques developed by Maxim and Gilbert (1977) *Proc. Natl. Acad. Sci. USA* 74:560 or Sanger (1977) *Proc. Natl. Acad. Sci. USA* 74:5463. It is also contemplated that any of a variety of automated sequencing procedures can be utilized when performing the diagnostic assays (Naeve et al. (1995) *Biotechniques* 19:448), including sequencing by mass spectrometry (see, e.g., PCT International Publ. No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the BAFF-R gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type BAFF-R sequence with potentially mutant RNA or DNA obtained from a tissue sample. The double-stranded duplexes are treated with an agent that cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci USA* 85:4397; Saleeba et al. (1992) *Methods Enzymol.* 217:286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in BAFF-R cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a BAFF-R sequence, e.g., a wild-type BAFF-R sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in BAFF-R genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766, see also Cotton (1993) *Mutat. Res.* 285:125-144; Hayashi (1992) *Genet. Anal. Tech. Appl.* 9:73-79). Single-stranded DNA fragments of sample and control BAFF-R nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) Nature 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucl. Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a BAFF-R gene.

Furthermore, any cell type or tissue, in which BAFF-R is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on BAFF-R activity (e.g., BAFF-R gene expression), as identified by a screening assay described herein can be administered to individuals to treat (prophylactically or therapeutically) disorders (e.g., cancer-related or autoimmune disorders). In conjunction with such treatment, the pharmacogenomics (i.e., the study of the relationship between an individual's genotype and that individuals response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of BAFF-R protein, expression of BAFF-R nucleic acid, or mutation content of BAFF-R genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum (1996) *Clin. Exp. Pharmacol. Physiol.* 23:983-985 and Linder (1997) *Clin. Chem.* 43:254-266. In general, two types of pharmacogenetic conditions can be differentiated. Genetic conditions transmitted as a single factor altering the way drugs act on the body (altered drug action)

or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of BAFF-R protein, expression of BAFF-R nucleic acid, or mutation content of BAFF-R genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a BAFF-R modulator, such as a modulator identified by one of the exemplary screening assays described herein.

Monitoring Clinical Efficacy

Monitoring the influence of agents (e.g., drugs, compounds) on the expression or activity of BAFF-R (e.g., the ability to modulate aberrant cell proliferation and/or differentiation) can be applied not only in basic drug screening, but also in clinical trials. For example, the effectiveness of an agent determined by a screening assay as described herein to increase BAFF-R gene expression, protein levels, or upregulate BAFF-R activity, can be monitored in clinical trials of subjects exhibiting decreased BAFF-R gene expression, protein levels, or downregulated BAFF-R activity. Alternatively, the effectiveness of an agent determined by a screening assay to decrease BAFF-R gene expression, protein levels, or downregulate BAFF-R activity, can be monitored in clinical trials of subjects exhibiting increased BAFF-R gene expression, protein levels, or upregulated BAFF-R activity. In such clinical trials, the expression or activity of BAFF-R and, preferably, other genes that have been implicated in, for example, a disorder, can be used as a "read out" or markers of the immune responsiveness of a particular cell.

For example, genes, including BAFF-R, that are modulated in cells by treatment with an agent (e.g., compound, drug or small molecule) that modulates BAFF-R activity (e.g., identified in a screening assay as described herein) can be identified. Thus, to study the effect of agents on cellular proliferation disorders, for example, in a clinical trial, cells can be isolated and RNA prepared and analyzed for the levels of expression of BAFF-R and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of BAFF-R or other genes. In this way, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a BAFF-R protein, mRNA, or genomic DNA in the preadministration sample; (iii) obtaining one or more post-administration samples from the subject; (iv) detecting the level of expression or activity of the BAFF-R protein, mRNA, or genomic DNA in the post-administration samples; (v) comparing the level of expression or activity of the BAFF-R protein, mRNA, or genomic DNA in the pre-administration sample with the BAFF-R protein, mRNA, or genomic DNA in the post administration sample or samples; and (vi) altering the administration of the agent to the subject accordingly. For example, increased administration of the agent may be desirable to increase the expression or activity of BAFF-R to higher levels than detected, i.e., to increase the effectiveness of the agent. Alternatively, decreased administration of the agent may be desirable to decrease expression or activity of BAFF-R to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant BAFF-R expression or activity.

Diseases and disorders that are characterized by increased (relative to a subject not suffering from the disease or disorder) levels or biological activity may be treated with therapeutics that antagonize (i.e., reduce or inhibit) activity. Therapeutics that antagonize activity may be administered in a therapeutic or prophylactic manner. Therapeutics that may be utilized include, but are not limited to, (i) a BAFF-R polypeptide, or analogs, derivatives, fragments or homologs thereof; (ii) antibodies to a BAFF-R peptide; iii) nucleic acids encoding a BAFF-R peptide; (iv) administration of antisense nucleic acid and nucleic acids that are "dysfunctional" (i.e., due to a heterologous insertion within the coding sequences of coding sequences to a BAFF-R peptide) are utilized to "knockout" endogenous function of a BAFF-R peptide by homologous recombination (see, e.g., Capecchi (1989) *Science* 244:1288-1292); or (v) modulators (i.e., inhibitors, agonists and antagonists, including additional peptide mimetic of the invention or antibodies specific to a peptide of the invention) that alter the interaction between a BAFF-R peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a BAFF-R peptide, or analogs, derivatives, fragments or homologs thereof; or an agonist that increases bioavailability.

Increased or decreased levels can be readily detected by quantifying peptide and/or RNA, by obtaining a patient tissue sample (e.g. from biopsy tissue) and assaying it in vitro for RNA or peptide levels, structure and/or activity of the expressed peptides (or mRNAs of a BAFF-R peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with an aberrant BAFF-R expression or activity, by administering to the subject an agent that modulates BAFF-R expression or at least one BAFF-R activity. Subjects at risk for a disease that is caused or contributed to by aberrant BAFF-R expression or activity can be identified by, for example, any or a combination of diagnostic or prognostic assays as described herein. Administration of a prophylactic agent can occur prior to the manifestation of symptoms characteristic of the BAFF-R aberrancy, such that a disease or disorder is prevented or, alternatively, delayed in its progression. Depending on the type of BAFF-R aberrancy, for example, a BAFF-R agonist or BAFF-R antagonist agent can be used for treating the subject. The appropriate agent can be determined based on screening assays described herein.

Another aspect of the invention pertains to methods of modulating BAFF-R expression or activity for therapeutic purposes. The modulatory method of the invention involves contacting a cell with an agent that modulates one or more of the activities of BAFF-R protein activity associated with the cell. An agent that modulates BAFF-R protein activity can be an agent as described herein, such as a nucleic acid or a protein, a naturally-occurring cognate ligand of a BAFF-R protein, a peptide, a BAFF-R peptidomimetic, or other small molecule. In one embodiment, the agent stimulates one or more BAFF-R protein activity. Examples of such stimulatory agents include active BAFF-R protein and a nucleic acid molecule encoding BAFF-R that has been introduced into the cell. In another embodiment, the agent inhibits one or more BAFF-R protein activity. Examples of such inhibitory agents include antisense BAFF-R nucleic acid molecules and anti-BAFF-R antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a BAFF-R protein or nucleic acid molecule. In one embodiment, the method involves administering an agent (e.g., an agent identified by a screening assay described herein), or combination of agents that modulates (e.g. upregulates or downregulates) BAFF-R expression or activity. In another embodiment, the method involves administering a BAFF-R protein or nucleic acid molecule as therapy to compensate for reduced or aberrant BAFF-R expression or activity.

In one embodiment, the invention provides methods of using BAFF-R. Included in such methods are methods of inhibiting B cell growth, dendritic cell-induced B cell growth and maturation or immunoglobulin production in an animal using BAFF-R polypeptide comprising at least a BAFF binding portion of BAFF-R. Other embodiments include methods of stimulating B-cell growth, dendritic cell-induced B-cell growth and maturation or immunoglobulin production in an animal using BAFF-R polypeptide (such as by transfecting cells which are deficient in BAFF-R with vectors to allow efficient expression of BAFF-R, or by administering antibodies that bind BAFF-R and mimic BAFF).

In another embodiment, the invention provides methods of using BAFF-R in the treatment of autoimmune diseases, hypertension, cardiovascular disorders, renal disorders, B-cell lympho-proliferate disorders, immunosuppressive diseases, organ transplantation, and HIV. Also included are methods of using agents for treating, suppressing or altering an immune response involving a signaling pathway between BAFF-R and its ligand, and methods of inhibiting inflammation by administering an antibody specific for a BAFF-R or an epitope thereof.

The methods of the present invention are preferably carried out by administering a therapeutically effective amount of a BAFF-R polypeptide, a chimeric molecule comprising a BAFF-R polypeptide fused to a heterologous amino acid sequence, or an anti-BAFF-R antibody homolog.

In one embodiment, the invention provides pharmaceutical compositions comprising a BAFF-R polypeptide and a pharmaceutically acceptable excipient.

In another embodiment, the invention provides chimeric molecules comprising BAFF-R polypeptide fused to a heterologous polypeptide or amino acid sequence. An example of such a chimeric molecule comprises a BAFF-R fused to a Fc region of an immunoglobulin or an epitope tag sequence.

In another embodiment, the invention provides an antibody that specifically binds to a BAFF-R polypeptide. Optionally, the antibody is a monoclonal antibody.

In one embodiment of the invention is a method of treating a mammal for a condition associated with undesired cell proliferation by administering to the mammal a therapeutically effective amount of a composition comprising an BAFF-R antagonist, wherein the BAFF-R antagonist comprises a polypeptide that antagonizes the interaction between BAFF-R and its cognate receptor or receptors, with a pharmaceutically acceptable recipient.

In a preferred embodiment the cognate receptor of BAFF on the surface of the cell is BAFF-R.

The method can be used with any BAFF-R antagonist that has a polypeptide that antagonizes the interaction between BAFF and its cognate receptor or receptors. Examples of BAFF-R antagonists include but are not limited to soluble BAFF-R polypeptide, soluble chimeric BAFF-R molecules, including but not limited to BAFF-R-IgG-Fc and anti-BAFF-R antibody homologs.

The method of the invention can be used with any condition associated with undesired cell proliferation. In particular the methods of the present invention can be used to treat tumor cells which express BAFF and/or BAFF-R.

Examples of cancers whose cell proliferation is modulated by BAFF may be screened by measuring in vitro the level of BAFF and/or BAFF-R message expressed in tumor tissue libraries. Tumor tissue libraries in which BAFF and/or BAFF-R message is highly expressed would be candidates.

Alternatively, one may screen for candidates searching the public and private databases (i.e., Incyte database) with, for example, the full length human BAFF cDNA sequence.

The BAFF-R antagonists of the subject invention which are used in treating conditions associated with undesired cell proliferation, in particular tumor therapy, advantageously inhibit tumor cell growth greater than 10%, 20%, 30% or 40% and most advantageously greater than 50%. The BAFF-R antagonists are obtained through screening. For example, BAFF-R antagonists can be selected on the basis of growth inhibiting activity (i.e., greater than 10%, 20%, 30%, 40% or 50%) against the human colon carcinoma HT29 or human lung carcinoma A549 which are derived from a colon and lung tumor respectively.

Another embodiment of the invention, provides methods of inhibiting B-cell and non-B cell growth, dendritic cell-induced B-cell growth and maturation or immunoglobulin production in an animal using BAFF-R polypeptides such as those described above.

The method of inhibiting B-ell and non-B cell growth, dendritic cell-induced B-cell growth and maturation or immunoglobulin production may also include administration of an anti-BAFF-R antibody (polyclonal or monoclonal) that binds to BAFF-R and inhibits the binding of BAFF to BAFF-R. Administration of the antibody thereby inhibits B-cell and non-B cell growth, dendritic cell-induced B-cell growth and maturation or immunoglobulin production. The amount of antibody that may be suitable for use may be extrapolated from the in vivo data provided herein. Various methods are known in the art to extrapolate dosages from animal experiments, including for example, extrapolation based on body weight or surface area.

In some embodiments of the invention the BAFF-R:Fc polypeptides or anti-BAFF-R antibodies are administered in an amount of about 1 to 20 mg/kg/dose. Doses may be given twice weekly, once weekly, one every two weeks or once monthly, as needed. A physician will be able to determine the proper dose by determining efficacy balanced against reducing any untoward effects of the therapy.

In another embodiment, the invention provides methods of using BAFF-R or anti-BAFF-R antibodies in the treatment of autoimmune diseases, hypertension, cardiovascular disorders, renal disorders, B-cell lympho-proliferate disorders, immunosuppressive diseases, organ transplantation, inflammation, and HIV. Also included are methods of using agents for treating, suppressing or altering an immune response involving a signaling pathway between BAFF-R and its ligand.

Methods of Inhibiting Aggregation of Expressed Protein, Including BAFF-R and BAFF-R:Fc.

The invention also provides a method for inhibiting or decreasing aggregation of expressed protein, particularly human BAFF-R or huBAFF-R:Fc, which tends to aggregate during expression, frustrating purification at high yields. In the method of the invention the amino acid sequence of a protein that tends to aggregate when expressed in a recombinant system is compared to the amino acid sequence of a homolog of the protein that exhibits less aggregation activity. The two homologs will have conserved domains and non-conserved amino acids there between and perhaps interspersed therein. In general, at least one of the non-conserved amino acids amino acids of the aggregating protein may be substituted for the amino acid in the homolog to alleviate aggregation. In some embodiments, nonpolar amino acids are substituted. Nonpolar amino acids include glycine, alanine, valine, leucine, isoleucine, proline, phenylalanine, methionine, tryptophan, and cysteine. In some embodiments nonpolar amino acids substitute for other nonpolar amino acids. Preferred nonpolar amino acids to inhibit or decrease aggregation are proline and alanine. In other embodiments, an uncharged polar amino acid is substituted for a nonpolar amino acid. Uncharged polar amino acids include asparagine, glutamine, serine, threonine and tyrosine.

In the method of the invention, substitutions are made that preferably allow the protein to retain biological activity. In general, non-conserved amino acids are amenable to substitution without appreciably affecting biological activity.

In a specific example of the method of the invention, human BAFF-R protein may have amino acid substitutions introduced at positions V20, P21, A22 and L27 of SEQ ID NO:5 (or V41, P42, A43, and L48 of SEQ ID NO:10) and various combinations thereof, which greatly alleviates aggregation of the protein. Similar strategies may be used for other proteins that tend to aggregate when expressed in recombinant systems. While not wishing to be bound by any particular theory of operation, it is believed that the substitution of uncharged polar amino acids for nonpolar amino acids imparts solubility to the protein and discourages aggregation of nonpolar regions between the proteins.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

EXAMPLES

Example 1

This example describes the molecular cloning of BAFF-R, a novel receptor for BAFF.

Materials and Methods

An oligo-dT primed cDNA library was made from BJAB cells, a human B cell line that binds human BAFF, and directionally cloned into the expression vector CH269. CH269 is a derivative of pCEP4 (Invitrogen) that contains the CMV promoter to drive expression of cloned DNA and also contains the oriP of EBV. This allows multicopy autonomous replication of these plasmids in cells that are stably transformed with EBNA-1, such as 293EBNA. The BJAB cDNA library was transfected into E. coli DH10B cells and seeded in a 96 well format as pools of approximately 2500 independent clones per well. DNA was prepared from these pools using the Qiagen BioRobot 9600. The DNA pools were transfected using Lipofectamine (Life Technologies) into 293EBNA cells seeded into fibronectin coated 6 well dishes. At 48 hours post-transfection the medium was removed and the cells washed with plate assay wash buffer (20 mM HEPES, 0.5 mg/ml bovine serum albumin, 0.1% NaN$_3$). Cell monolayers were overlaid with 100 mg/ml biotinylated human recombinant soluble myc-BAFF (myc-huBAFF) in binding buffer (PBS, 2% fetal bovine serum, 0.1% NaN$_3$) and incubated at room temperature for 1 hour. The myc-huBAFF (amino acids 136-285) used in the assay was expressed in *Pichia pastoris* and purified by anion exchange chromatography followed by gel filtration.

The BAFF solution was removed and the cells were washed and fixed by incubation with 1.8% formaldehyde-0.2% glutaraldehyde in PBS for 5 minutes. Cells were again washed and then incubated for 30 minutes with streptavidin conjugated with alkaline phosphatase (SAV-AP) (Jackson ImmunoResearch) at a 1:3000 dilution from stock in binding buffer. Cells were washed and stained with fast red/napthol phosphate Fierce). Cells binding the biotin-BAFF/SAV-AP complex were identified by the presence of a red precipitate after inspection under low power microscopy. Secondary screening entailed plating out the DH10B glycerol stocks of the BAFF binding pools for single colonies, inoculating to culture in pools of 100, and repeating the BAFF binding assay as described above. Secondary screen positive pools were similarly broken down to individual clones and assayed for BAFF binding upon transfection to 293EBNA as described above. The DNA sequence of the independent BAFF binding clones was determined.

Results

One of the BAFF binding clones was pJST576. It has in insert size of 1201 base pairs (bp) not including the poly-A tail. The sequence of the insert of pJST576 is shown in FIG. 1A (SEQ ID NO:1). BLAST analysis of this clone showed homology in the Genbank database to the chromosome 22 BAC clone HS250D10 (accession number Z99716). The entire pJST576 sequence is found within this BAC. Homology was also found to the 3' end of a human EST, AI250289 (IMAGE clone 2000271). The EST was generated from a human follicular lymphoma library. The EST AI250289 was obtained from Incyte and the sequence of the insert was determined (FIG. 1B) (SEQ ID NO:2). This sequence added 15 bp of 5' sequence to the pJST576 sequence, which is contiguous with the genomic sequence and 23 bp, which was not. The remainder of the EST sequence has perfect homology to pJST576. An open reading frame could not be identified in these clones.

Example 2

In this example, we determine that the JST576 cDNA contains an intron and then establish an open reading frame.

Methods

The GENSCAN (Burge, C. & Karlin, S. J. (1997) *Mol. Biol.* 268:78-94) exon prediction program was run on the JST576 cDNA sequence. The results of this program predicted that an intron was present in the cDNA. In order to determine if the prediction was correct, PCR analysis was performed on first strand cDNA from 2 cell lines expressing JST576. RNA was purified from approximately 107 BJAB or IM-9 cells using the RNeasy kit (Qiagen) following the manufacturers suggested protocol. RNA was quantitated and 5 µg was used for first strand cDNA reactions using the Superscript preamplification kit (Life Technologies). Both oligo dT and random hexamers were used to generate the first strand product. Synthesis of the first strand was done following the recommended protocol. Three (1 of each reaction, 10 ng of JST576 or no DNA was then used as a template for PCR using oligonucleotides flanking the predicted intron. The oligonucleotides used in the reaction are the 5' oligos BAF-225 [5'-GGCCGAGTGCTTCGACCTGCT-3'] (SEQ ID NO:33) or BAF-226 [5'-GGTCCGCCACTGCGTGGCCTG-3'] (SEQ ID NO:34) and the 3' oligo BAF-191 [5'-CACCAAGACGGCCGGCCCTGA-3'] (SEQ ID NO:35). Each reaction contained 1×Pfu buffer (Stratagene), 200 (M dNTPs, 10% DMSO, 150 ng of each oligo, and 1.25 units of Turbo Pfu polymerase (Stratagene). The reactions were run for 35 cycles at 94° C. for 30 sec., 60° C. for 1 min. and 72° C. for 1.5 min. Ten µl of each reaction was run on a 1% agarose gel. The remaining products from the BJAB and IM-9 BAF-225/191 reactions were purified using the High Pure PCR product purification kit (Roche Molecular Biochemicals) and the bulk product was subjected to DNA sequencing. In addition, PCR products using the primers BAF-225 and BAF-191 were generated from resting B cell cDNA, subcloned and individual clones were sequenced. Here 5 µl of resting B cell cDNA (Clontech) was used in a PCR reaction with the BAF-225 and BAF-191 primers as detailed above. The PCR product was then purified using the High Pure PCR product purification kit and concentrated. In order to subclone the PCR fragment, the ends of the fragment were phosphorylated and made blunt using the Sure Clone ligation kit (Amersham Pharmacia Biotech) as recommended. The resulting product was cloned into the EcoRV site of pBluescriptII (Stratagene) and transformed into *E. coli*. Individual colonies were grown up, the plasmid DNA miniprepped. Six independent isolates were sequenced.

Results

The mature nucleotide and amino acid sequence of JST576 predicted by the GENSCAN program is shown in FIG. 2A (SEQ ID NO:3). PCR products from BJAB and IM-9 reactions spanning the predicted intron are shown in FIG. 2B and confirm the existence of an intron in the JST576 cDNA clone. The predicted size of the PCR product from the JST576 cDNA is approximately 788 bp for BAF-225/BAF-191 and 767 bp for BAF-226/BAF-191. The PCR products obtained from the JST576 template are approximately this size (lanes 10 and 11). The PCR products obtained using BAF-225/BAF-191 on either oligo dT primed BJAB or IM-9 first strand cDNA (lanes 2 and 6) are the same size and significantly shorter than the product from the JST576 cDNA. The predicted size of this fragment without the predicted intron is 484 bp. The size of the PCR products is consistent with this size. The same results were obtained if BJAB or IM-9 RNA was primed with random hexamers (lanes 4 and 8). The reactions using BAF-226/BAF-191 did not work on the first strand cDNA templates. Therefore, it appears that the intron predicted by the GENSCAN program does exist in the JST576 cDNA. The sequence of the spliced product from BJAB and IM-9 RNA was confirmed by sequencing the bulk PCR product and is reflected in the sequence shown in FIG. 2C (SEQ ID NO:4). The sequence is identical to the sequence shown in FIG. 2A (SEQ ID NO:3), except for the absence of the alanine codon (GCA) at nucleotide 149 (shown in small letters). The results of sequencing 6 independent clones from the RT-PCR reaction on resting B cell cDNA indicates that both splice acceptor sites are utilized. The preferred acceptor site appears to be the product resulting in one alanine residue (5/6 clones). However, the sequence predicted by GENSCAN (SEQ ED NO:3), which contains two alanines, was observed in 1/6 clones. Therefore an open reading frame for human JST576 has been established and a single amino acid splice variant has been determined. The open reading frame predicts a protein of 184 amino acids shown in FIG. 2D (SEQ ID NO:5). The analine (A) residue in bold represents the splice variant. This protein is referred to as BAFF-R. The deduced amino acid sequence of BAFF-R includes a hydrophobic region from residues 72-100 (Hopp-Woods algorithm) and a potential transmembrane segment from residues 84-102 as analyzed by the TMPred algorithm. This region is followed by a highly charged stretch of amino acids that may function as a stop transfer signal. BAFF-R lacks an N-terminal signal sequence and is a type III membrane protein similar to the other BAFF binding proteins BCMA (Laabi et al. (1992) *EMBO J.* 11:3897-3904) and TACI (von Bulow and Bram, (1997) *Science* 278:138-141). The N-terminus is predicted to be the extracellular domain of BAFF-R and contains a 4 cysteine motif at residues 19-35 unlike any other member of the TNF receptor family. The C-terminus of BAFF-R is predicted to be the intracellular domain.

Example 3

Here we determine the DNA sequence upstream of the proposed initiating methionine for human BAFF-R including an in-frame stop codon.

Methods

A primer BAF-254 (5'GGGCGCCTACAATCTCAGCTA 3') (SEQ ID NO:36) was made to the genomic sequence present in the BAC HS250d10 (Genbank accession number Z99716), upstream of the proposed ATG and used in a PCR reaction with the oligo BAF-236 (5' GGCGGACCAGCAG-GTCGAAGCACTC 3') (SEQ ID NO:37). The template in the reaction was first strand cDNA made from human spleen RNA (Clontech) using the PCR preamplification kit as described by the manufacturer (Life Technologies). The PCR reaction contained 3 µl of the first strand reaction, 1×Pfu buffer (Stratagene), 10% DMSO, 0.2 mM dNTPs, 150 ng each primer and 1.25 units Pfu Turbo polymerase (Stratagene). The PCR product was purified using the High Pure PCR Product Purification kit following the manufacturer's directions (Roche Molecular Biochemicals). The ends of the PCR product were made blunt and phosphorylated using the Sure Clone ligation kit (Amersham Pharmacia Biotech), cloned into the EcoRV site of pBSK2 (Stratagene) and transformed into DH5 cells. Colonies resulting from the ligation were miniprepped using the Wizard system (Promega) and then sequenced using an ABI machine.

Results

The sequence of the PCR product confirms that the mRNA contains sequences directly upstream of the ATG that is contained in the genomic sequence. This sequence is underlined in the sequence shown in FIG. 3. The presence of an in-frame upstream stop codon and the absence of another methionine indicate that the methionine found in the JST576 cDNA is the correct initiating methionine.

Example 4

This example describes the cloning of the murine BAFF-R cDNA.

Methods

Approximately one million phage plaques were screened from the murine A20 cell line cDNA library purchased from Stratagene (La Jolla, Calif.) as detailed by the manufacturer. The JST576 human BAFF-R cDNA was digested with EcoNI and run on a 1% low melt gel. The 425 bp fragment containing was cut out of the gel and weighed. Three times the volume of water was added and the gel fragment was boiled for 5 min. The fragment was labeled with 50 µCi $^{32}$P-dCTP (Amersham) in a reaction containing 50 mM Tris pH 8, 5 mM MgCl$_2$, 10 µM β-mercaptoethanol, 200 mM HEPES pH 6.5, 20 (M dNTPs (except dCTP), 0.27 units of pd(N)6 hexanucleotides (Amersham Pharmacia Biotech) and 1 unit of Klenow enzyme (USB) overnight at room temperature. About one million counts per ml of probe was incubated with the filters in plaque screening buffer (50 mM Tris, 1% SDS, 1M NaCl, 0.1% Sodium Pyrophosphate, 0.2% PVP, 0.2% Ficoll, 0.2% BSA) overnight at 65° C. The filters were washed in 2×SSC and 0.1% SDS at 50° C. for 1.5 hrs (3×2 liters) and then exposed to x-ray film for 2 days. Approximately 36 positive plaques were identified. Of these 6 were plaque purified. The phagemids were released using the in vivo excision protocol detailed by Stratagene. The resulting colonies were grown up and the DNA was then miniprepped (Qiagen). The cDNA clones were sequenced.

Results

The murine BAFF-R consensus nucleotide sequence is presented as FIG. 4A (SEQ ID NO:8) and the amino acid sequence is presented in FIG. 4B (SEQ ID NO:9). Three of the clones contained a 10 amino acid deletion from amino acid 119 to 129 in the intracellular domain of murine BAFF-R. The alignment of the human and murine BAFF-R sequences illustrates that the 4 cysteine residues in the extracellular domain are conserved, that the position of the initiating methionine is similar and that the C-terminal region of the proteins is highly conserved (FIG. 4C), with the last 24 residues being identical. The sequences have approximately 56% identity overall.

Example 5

In this example, the ability of human recombinant soluble BAFF to bind to cells co-transfected with pJST576 and a GFP reporter plasmid is described.

Materials and Methods

The reporter plasmid encodes a membrane anchored GFP molecule and allows identification of transfected cells from non-transfected cells. 293EBNA cells were co-transfected with the reporter plasmid and pJST576 using Lipofectamine 2000 (Life Technologies). At 18-20 hr post-transfection, cells were detached from the plates with 5 mM EDTA in PBS and counted. The cells were washed twice with FACS buffer (PBS containing 10% fetal bovine serum, 0.1% NaN$_3$) and 2.5×10$^5$ cells were incubated for 1 hour on ice with biotinylated myc-huBAFF diluted into FACS buffer over a concentration range of 8 ng/ml to 5 ug/ml. The cells were washed with FACS buffer and incubated for 30 minutes with streptavidin conjugated with phycoerythrin (SAV-PE) (Jackson ImmunoResearch) at a 1:100 dilution from stock. The cells were again washed with FACS buffer and resuspended in 1% paraformaldehyde in FACS buffer. The cells were analyzed by FACS for GFP and PE fluorescence and the data was formatted in a four quadrant dot plot. The dots in the two rightward quadrants represent cells expressing the transfection reporter GFP. The dots in the two upper quadrants represent cells having bound biotinylated myc-huBAFF with this binding revealed by SAV-PE. The cells in the upper right quadrant are transfected cells that bind biotinylated myc-huBAFF.

Results

Figure 5:
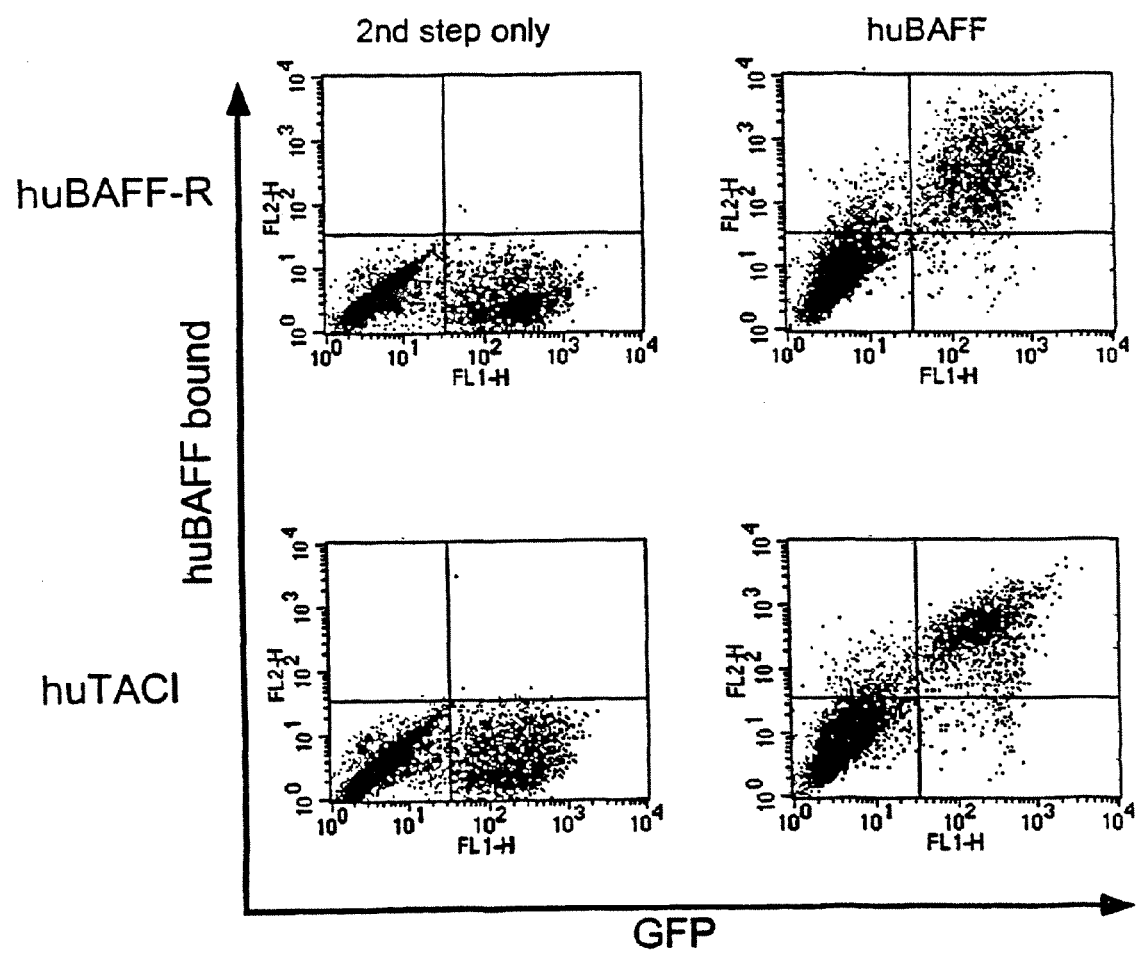
FIG. 5 depicts human BAFF binding to JST576 transfected cells. 293EBNA cells were co-transfected with pJST576 or CA336 (huTACI) and a GFP reporter construct. Cells assayed for BAFF binding with 1 ug/ml biotinylated myc-huBAFF followed by SAV-PE.

Unstained cells and cells stained only with SAV-PE show approximately 50% are GFP positive and have been co-transfected with the reporter plasmid (FIG. 5). When cells co-transfected with the GFP reporter and pJST576 are stained with 1 ug/ml biotinylated myc-huBAFF nearly all the cells in the lower right quadrant shift up, indicating BAFF binding. A similar result is seen if a plasmid expressing huTACI is co-transfected in place of pJST576. TACI is known to bind BAFF. The cells were stained with five fold dilutions of biotinylated myc-huBAFF from 5 ug/ml to 8 ng/ml and as the concentration of biotinylated myc-huBAFF decreased the intensity of the shift decreased.

Example 6

In this example, the ability of human recombinant soluble BAFF or murine recombinant soluble BAFF to bind to cells co-transfected with pJST576 and a GFP reporter plasmid is described.

Materials and Methods

Co-transfections to 293EBNA were as described in Example 5. At 18-20 hr post-transfection, cells were detached, counted, and stained for FACS analysis similar to Example 5 with the following modifications. The cells were incubated for 1 hour on ice with 5 ug/ml of either murine or human recombinant soluble flag-BAFF, followed after washing by incubation for 30 minutes with 5 ug/ml of the anti-flag monoclonal antibody M2 (Sigma Aldrich), and then revealed by incubating the washed cells for 30 minutes with PE conjugated donkey anti-mouse IgG (Jackson ImmunoResearch) at a 1:100 dilution from stock. The cells were again washed, fixed with paraformaldehyde, and analyzed by FACS for GFP and PE positive cells.

Results

Figure 6:
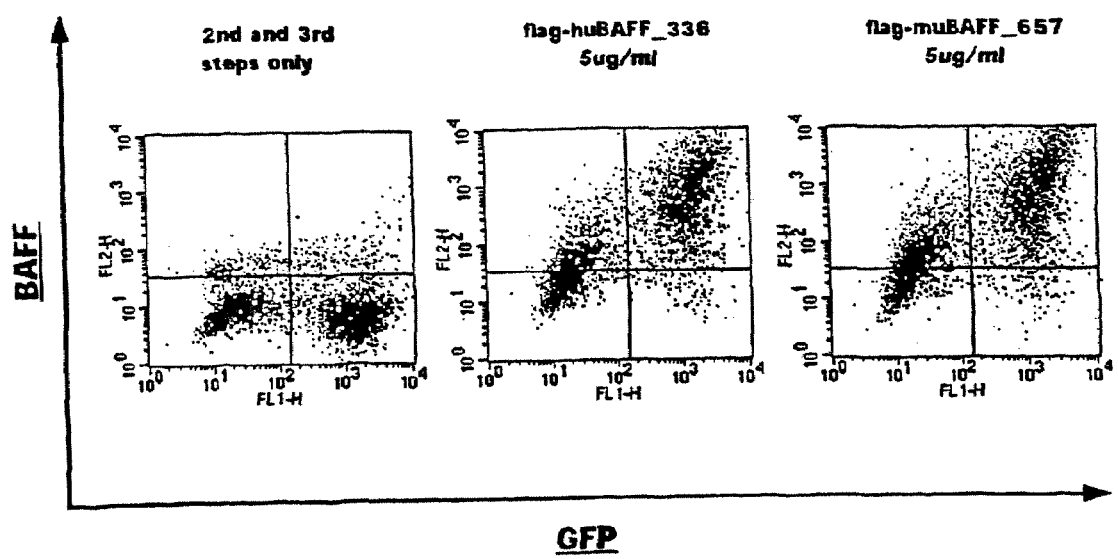
FIG. 6 shows human and murine BAFF binding to JST576 transfected cells. 293EBNA cells were co-transfected with pJST576 and a GFP reporter construct. Cells assayed 24 hr later for BAFF binding with 5 ug/ml flag-huBAFF or flag-muBAFF followed anti-flag monoclonal antibody M2 and donkey anti-mouse IgG-PE.

Approximately 50% of the cells are GFP positive and have therefore been co-transfected with the reporter plasmid (FIG. 6). When cells co-transfected with the GFP reporter and pJST576 are stained with 5 ug/ml of either human or murine recombinant soluble flag-BAFF, nearly all the cells in the lower right quadrant shift up. This indicates that both murine and human BAFF bind to cells transfected pJST576.

Example 7

In this example, the inability of murine recombinant soluble APRIL to bind to cells co-transfected with pJST576 and a GFP reporter plasmid is described.

Materials and Methods

Co-transfections to 293EBNA were as described in Example 5. At 18-20 hr post-transfection, cells were detached, counted, and stained for FACS analysis similar to Example 5 with the following modifications. The cells were incubated for 1 hour on ice with 1 ug/ml of murine recombinant soluble myc-APRIL, followed after washing by incubation for 30 minutes with 5 ug/ml of anti-murine APRIL monoclonal antibody, followed by a 30 minute incubation of the washed cells with 5 ug/ml biotinylated anti-rat IgG2b (Pharmingen), and finally revealed by incubating the washed cells for 30 minutes with SAV-PE. The cells were again washed, fixed with paraformaldehyde, and analyzed by FACS for GFP and PE positive cells.

Results

Figure 7:
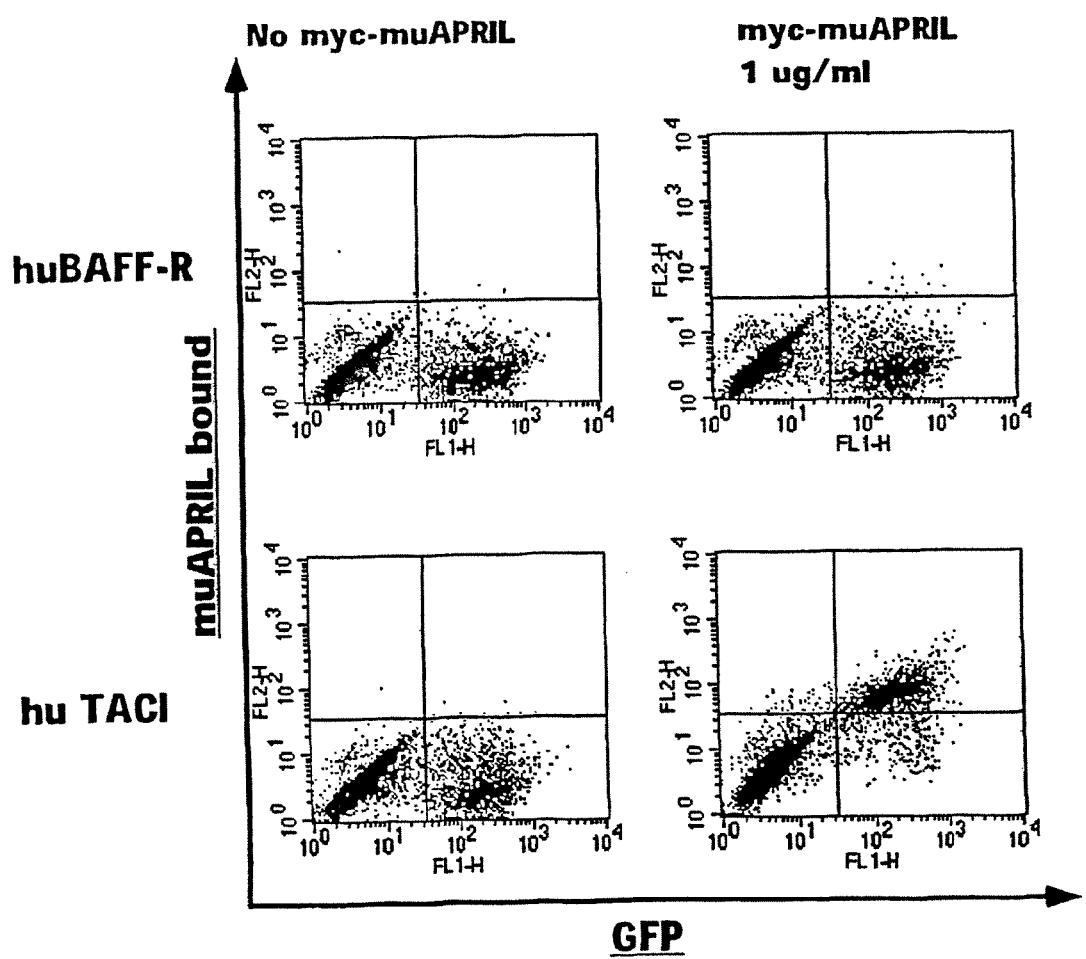
FIG. 7 shows that APRIL does not bind to JST576 transfected cells. 293EBNA cells were co-transfected with pJST576 or CA336 (huTACI) and a GFP reporter construct. Cells were assayed for APRIL binding with 1 ug/ml myc-muAPRIL followed by anti-muAPRIL rat-IgG2b, biotinylated anti-rat FcG2b, and SAV-PE.

Approximately 50% of the cells are GFP positive and have therefore been co-transfected with the reporter plasmid (FIG. 7). When cells co-transfected with the GFP reporter and pJST576 are stained with 1 ug/ml of murine myc-APRIL, none of the cells in the lower right quadrant shift up. This is in contrast to cells co-transfected with a plasmid expressing human TACI instead of pJST576. In these transfected cells, nearly all were positive for murine myc-APRIL binding. It has been previously shown that both BAFF and APRIL bind to both TACI and BCMA. Therefore the fact that APRIL does not bind to BAFF-R as expressed on pJST576 transfected cells indicates a specificity of BAFF-R for BAFF.

Example 8

This example describes the ability of BAFF-R as expressed from pJST576 to be co-immunoprecipitated by recombinant soluble human flag-BAFF.

Materials and Methods

293EBNA cells were transfected by Lipofectamine 2000 with pJST576, a vector only control, or a plasmid expressing huTACI as a positive control for BAFF binding. After 20 hours incubation the transfection medium was aspirated, the cells washed with PBS, and the media replaced with $^{35}$S labeling media (9 parts DMEM lacking methionine and cysteine to 1 part complete DMEM, supplemented with 10% dialyzed fetal bovine serum, 4 mM glutamine, and 100 µCi/ml $^{35}$S methionine and cysteine (Translabel, ICN Radiochemicals). Cells were incubated in this medium for six hours after which the media was removed. Cells were washed with PBS and then solubilized with 250 µl Extraction Buffer (1% Brij 98, 150 mM NaCl, 50 mM Tris pH 7.5). Co-immunoprecipitations were performed by incubating 75 µl of the $^{35}$S labelled cell extracts with 5 µg recombinant soluble human flag-BAFF in 1 ml DMEM-10% fetal bovine serum-0.1% NaN$_3$ overnight at 4° C. The anti-flag monoclonal antibody M2, 10 µg, and protein A-Sepharose were added and incubations continued for 2 hours. The Sepharose beads were collected by centrifugation, washed with FACS buffer, and resuspended in SDS loading buffer with beta-mercaptoethanol as a reducing agent Samples were boiled 5 minutes, centrifuged briefly to pellet the Sepharose beads, and an aliquot run on SDS-PAGE. The gel was incubated with Enlightning (New England Nuclear), dried down, and exposed to film at –80° C.

Results

Figure 8:
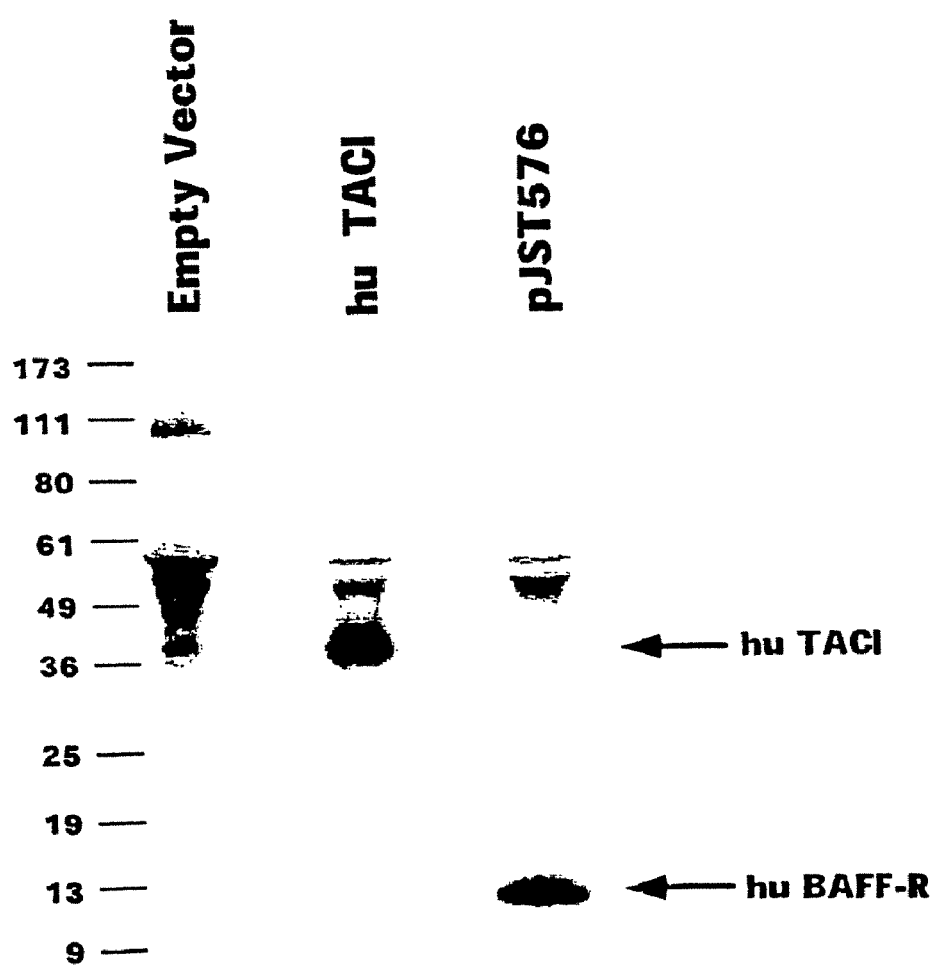
FIG. 8 shows that BAFF precipitates a protein from JST576 transfected cells. 293EBNA cells were transfected with either BAFF-R (pJST576), vector only (CH269) or huTACI (CA336) and pulsed with $^{35}$S cysteine and methionine. Extracts were immunoprecipitated with flag-huBAFF and run on a reducing SDS-PAGE gel. Molecular weight markers are indicated at left.

This co-immunoprecipitation binds flag-BAFF to the protein A Sepharose beads through the anti-flag antibody, M2. It will also bring down any proteins in the cell extract that bind to flag-BAFF, and these radiolabelled proteins will be detected by autoradiography. As 293EBNA cells do not bind BAFF, the empty vector control shows the background inherent in the procedure (FIG. 8). When extracts from cells transfected for TACI are co-immunoprecipitated with flag-BAFF, a band with an apparent molecular weight of approximately 34 kDa is observed. This is the approximate predicted molecular weight for full length human TACI (31.2 kDa), a protein known to bind BAFF. When extracts from cells transfected with pJST576 are co-immunoprecipitated with flag-BAFF, a band with an apparent molecular weight of approximately 12 kDa is observed. The predicted molecular weight for BAFF-R expressed from pJST576 is 18.9 kDa. The disparity between predicted and observed molecular weights could be due to anomalous electrophoretic mobility due to the charge or conformation of BAFF-R. Another possibility is that 12 kDa is a proteolytic fragment of BAFF-R.

Example 9

This example describes the generation of soluble forms of BAFF-R. Oligonucleotide primers complementary to pJST576 can be designed to PCR amplify the BAFF-R extracellular domain in the absence of transmembrane and intracellular domains. Typically, one includes most of the stalk, or amino acid region between the ligand binding domain and the transmembrane domain. One could vary amount of stalk region included to optimize the potency of the resultant soluble receptor. This amplified fragment would be engineered with suitable restriction sites to allow cloning to various heterologous leader sequences on the 5' end of the fragment and to various Ig fusion chimera fusion vectors at the 3' end. Alternatively, one can insert a stop signal at the 3' end of the BAFF-R extracellular domain to and make a soluble form of the receptor or use another C-terminal fusion partner without resorting to the use of an instead of using the Ig fusion chimera approach. Also, one could create an N-terminal fusion protein consisting of a fusion partner containing a signal sequence followed by the N-terminal extracellular domain of BAFF-R. The resultant vectors can be expressed in most systems used in biotechnology including yeast, insect cells, bacteria, and mammalian cells and examples exist for all types of expression. Various human Fc domains can be attached to optimize or eliminate FcR and complement interactions as desired. Alternatively, mutated forms of these Fc domains can be used to selectively remove FcR or complement interactions or the attachment of N-linked sugars to the Fc domain which has certain advantages. An example of a BAFF-R:Fc fusion molecule is shown in FIG. 9. This molecule contains the type I leader sequence from a murine Ig-k gene linked by an Aat2 restriction site to the BAFF-R extracellular domain (amino acid residues 2-71 as shown in FIG. 2D) which is in turn linked by a SaiI restriction site to the Fc domain of human IgG1.

Example 10

In this example we show the expression profile of BAFF-R in human tissues and cell lines using Northern blot analysis.

Materials and Methods

Various B and non-B cell lines were grown under the appropriate conditions. RNA was prepared from approximately $10^7$ cells using the RNeasy kit (Qiagen). The RNAs were quantified and 20 μg of each sample was run on a 1.2% formaldehyde gel as described by Sambrook et al. MOLECULAR CLONING: A LABORATORY MANUAL, 1989. The gel was blotted to a nylon membrane (BMB) and then ultraviolet (UV) cross-linked. Several human Northern blots (12 lane multi-tissue, human II and Immune system II) were purchased from Clontech. The filters was were prehybridized at 65° C. in ExpressHyb (Clontech) buffer for 30 min. and then hybridized with a randomly primed $^{32}p$ labeled EcoNI fragment from the 3' end of JST576 for about 3 hrs. The filters were washed at room temperature in 2×SSC/0.05% SDS for 45 min. and then at 50° C. in 0.1×SSC/0.1% SDS for 45 min. The filter was exposed to X-ray film for 4 days using 2 intensifying screens. In addition, several human Northern blots (12 lane multi-tissue, human II and Immune system II) were purchased from Clontech, hybridized to the JST576 probe and treated as above.

Results

Figure 10:
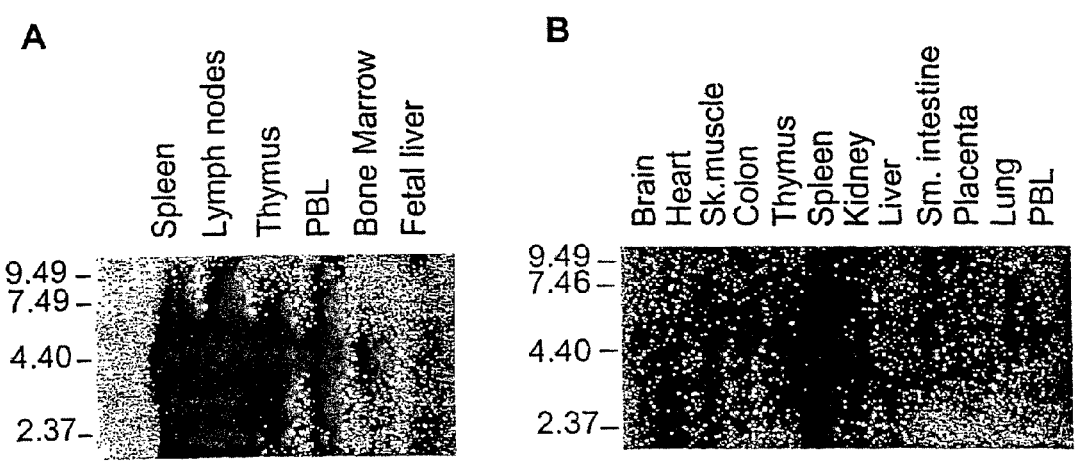
FIG. 10 depicts the results of Northern blot analysis using the EcoNI fragment of JST56 as a probe. All exposures are 4 days. 10A: Clontech human Immune II blot; 10B: Clontech human 12 lane multi-tissue blot; 10C: Clontech human multi-tissue II blot.
Figure 10C:
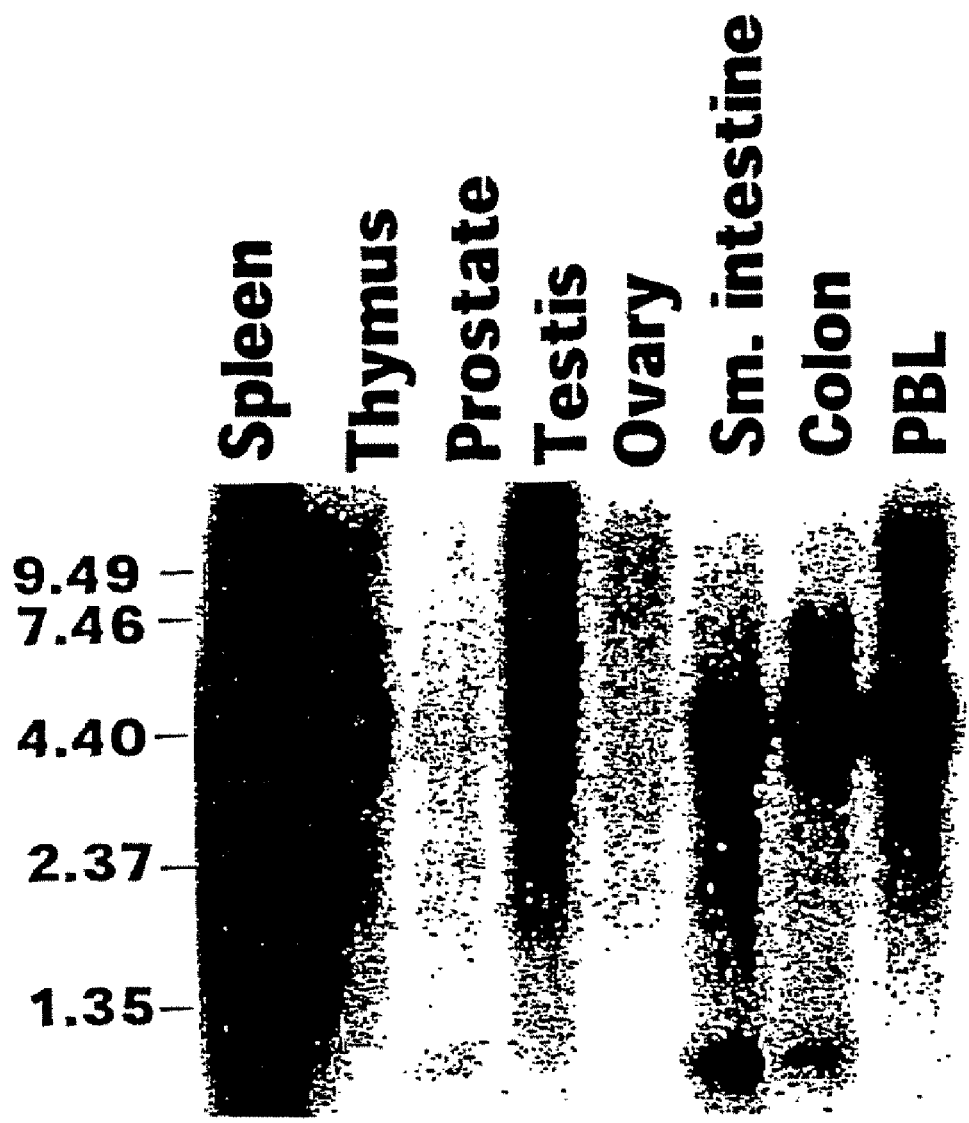
Figure 11:
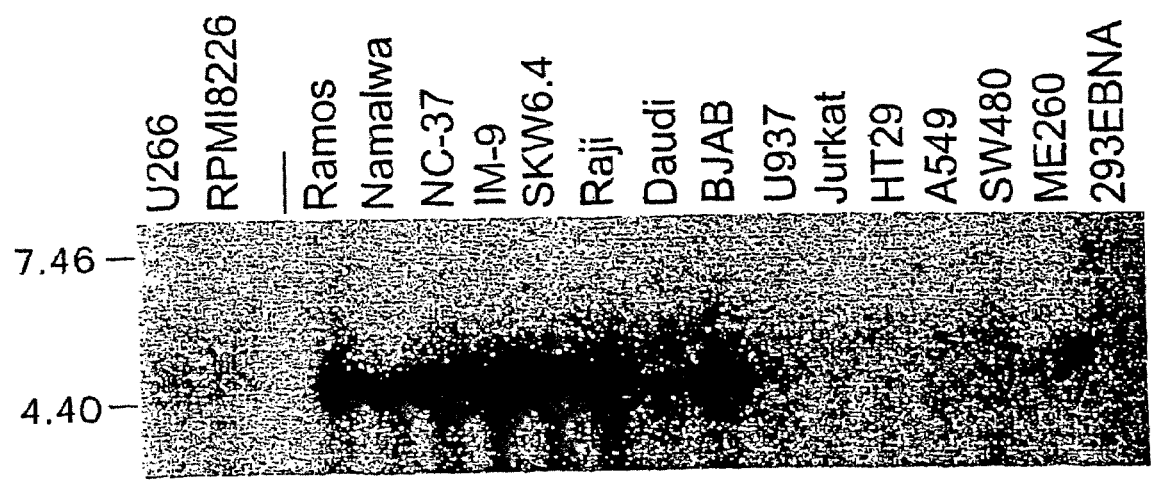
FIG. 11 shows the result of Northern blot analysis of 20 µg of total RNA isolated from various cell lines. The blot was probed with an EcoNI restriction fragment of JST576 and exposed for 4 days. The ability of the cell lines to bind BAFF, as determined by FACS analysis, is indicated below the lane.

The mRNA for BAFF-R appears to predominately expressed in the immune system organs at this level of detection. The highest level is in the spleen and lymph nodes, but mRNA was also apparent in PBLs, thymus, small intestine and colon (FIG. 10A, B and C). The approximate size of the message is 4.5 kb; there appears to be two mRNA populations in the samples where the gene is not highly expressed. Two mRNAs may exist in the spleen and lymph nodes as well. This may indicate that BAFF-R has alternative polyA addition sites or that the RNA undergoes alternative splicing. When a number of cell lines were examined for the presence of BAFF-R mRNA, the same 4.5 kb mRNA is detected. Only B cell lines express BAFF-R mRNA (FIG. 11). No mRNA is detected in the U266, RPMI8226 and Daudi cell lines or in the non-B cell lines examined.

Example 11

In this example we show that JST576 expression is restricted to the cell lines that bind BAFF.

Materials and Methods

Cell lines were purchased from ATCC and grown under the indicated conditions. Various B and non-B cell lines were grown under the appropriate conditions. RNA was prepared from approximately $10^7$ cells using the RNeasy kit (Qiagen). The RNAs were quantitated and 20 μg of each sample was run on a 1.2% formaldehyde gel as described by Sambrook et al. MOLECULAR CLONING: A LABORATORY MANUAL, 1989. The gel was blotted to a nylon membrane (BMB) and then UV cross-linked. The filter was hybridized with a JST576 labeled fragment and then washed as in Example 10. The cells were checked for their ability to bind BAFF using FACS analysis. Approximately 2.5-5×$10^5$ cells were collected, and washed. FLAG-tagged BAFF, diluted in PBS+5% FCS and 0.05% sodium azide (FACS buffer), was incubated with the cells over the concentration range (8-0.125 μg/ml) for 30 min. on ice. The cells were washed with FACS buffer and incubated, for 30 min. on ice, with the anti-FLAG monoclonal antibody M2 (Sigma) at 5 μg/ml. Again the cells were washed with FACS buffer and then incubated with a 1:5000 dilution of goat anti-mouse IgG PE conjugated antibody (Jackson Immuno Research) for 30 min. on ice. The cells were washed as above and then analyzed on a FACSCalibur flow sorter (Becton-Dickinson) using CellQuest software.

Results

The results of the BAFF binding experiments are shown in Table 1. The cell lines that bind BAFF are Ramos, Namalwa, IM-9, NC-37, Raji, BJAB and SKW6.4. The level of binding is indicated by the number of + signs. The cell lines that do not bind BAFF are U266, RPMI 8226, Daudi, U937, Jurkat, HT29, A549, SW480 and ME260. The ability of the cell lines to bind BAFF is correlated to the presence of BAFF-R mRNA shown in FIG. 11.

TABLE 1

| Cell Line | Type | BAFF Binding |
|---|---|---|
| BJAB | Burkitt lymphoma | +++ |
| IM-9 | Lymphoblast IgG | +++ |
| NC-37 | Lymphoblast EBV+ | ++ |
| Ramos | Burkitt lymphoma EBV− | ++ |
| Raji | Burkitt lymphoma | ++ |
| SKW6.4 | Lymphoblast IgM | ++ |
| Namalwa | Burkitt lymphoma | + |
| Daudi | Burkitt lymphoma EBV+ | − |
| U266 | Plasmacytoma | − |
| RPMI 8226 | Plasmacytoma | − |
| U937 | Monocyte | − |
| Jurkat | T Cell leukemia | − |
| HT29 | Colorectal adenocarcinoma | − |
| A549 | Lung carcinoma | − |
| SW480 | Colorectal adenocarcinoma | − |
| ME260 | Melanoma | − |

Example 12

This example describes the ability of a huBAFF-R:huIgG1 fusion protein that is expressed and secreted into the conditioned media by transiently transfected 293EBNA cells to co-immunoprecipitate recombinant soluble biotinylated myc-huBAFF.

Materials and Methods

293EBNA cells were transfected by Lipofectamine 2000 (LifeTechnologies) with either pJST618 which expresses huBAFF-R (aa2-71):Fc, a plasmid expressing huBCMA:huIgG1 as a positive control for BAFF binding, or a plasmid expressing huFN14:huIgG1 as a negative control for BAFF binding. After 24 hours incubation the conditioned media was harvested.

SDS-PAGE was run by mixing an equal volume of 2× SDS running buffer, with or without reducing agent, with the conditioned media and boiling for 5 minutes. The samples were then run on a 4-20% SDS polyacrylamide gel. Known quantities of purified hBCMA:Fc were run in adjacent lanes to estimate amount of hIgG1 fusion protein in the conditioned media Samples were transferred to membranes (Immobillon P, Millipore) by western blot in 0.01M CAPS pH11-10% MeOH buffer. Membranes were blocked with 5% non-fat dry milk (NFDM) in TBST, probed with 1:3000 dilution of goat anti-human IgG-HRP (Jackson ImmunoResearch) for 1 hour, washed in TBST and exposed to film. Co-immunoprecipitations were performed by incubating 200 μl of the conditioned media with 200 ng recombinant soluble human flag-BAFF in 1 ml DMEM-10% fetal bovine serum-0.1% NaN3 overnight at 4° C. Protein A-Sepharose was added and incubations continued for 2 hours. The Sepharose beads were collected by centrifugation, washed with FACS TBST buffer, and resuspended in SDS loading buffer with beta mercaptoethanol as a reducing agent. Samples were boiled 5 minutes, centrifuged briefly to pellet the Sepharose beads, and an aliquot run on SDS-PAGE. FLAG-huBAFF, 50 ng, was run as a positive control. Samples were transferred to PVDF membranes (Immobillon P, Millipore) by western blot in 0.01M CAPS pH 11/10% MeOH buffer. Membranes were blocked with 5% NFDM-TBST, probed with 1 μg/ml anti-FLAG M2-HRP for 1 hour, washed in TBST and exposed to film.

Results

Figure 12:
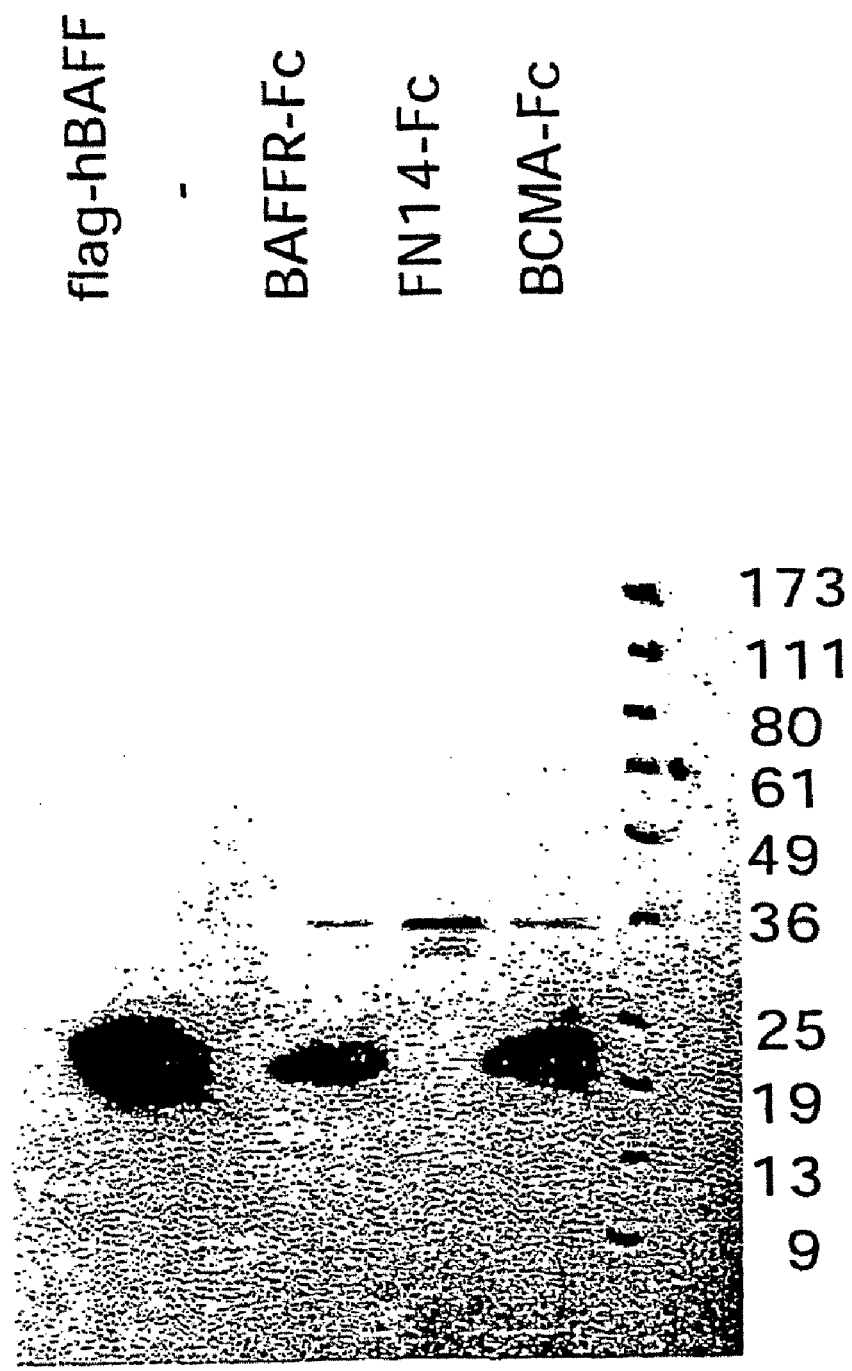
FIG. 12 shows the results of immunoprecipitation results using BAFF-R:Fc. Human BAFF is immunoprecipitated with BAFF-R:Fc or BCMA:Fc, but not Fn14-Fc. Control BAFF protein is shown in lane 1.

Co-immunoprecipitation brings down the various receptor:Fc fusions through the fusion partner interacting with protein A Sepharose. It will also bring down any proteins interacting with the R:IgG1 fusions, such as the flag-BAFF. Conditioned media from cells expressing hBCMA:Fc are able to co-inmunoprecipitate flag-BAFF, as expected, as a band that co-migrates with flag-BAFF is observed on the western blot (FIG. 12). Conditioned media from cells expressing hFN14:Fc does not co-immunoprecipitate flag-BAFF. The conditioned media from cells expressing BAFF-R:Fc are able to co-immunoprecipitate flag-BAFF. A band that co-migrates with flag-BAFF is observed on the western blot and is of similar intensity to that co-immunoprecipitated by huBCMA:huIgG1.

Example 13

This example illustrates the ability of a BAFF-R:Fc fusion protein, in this case huBAFF-R (aa2-71):huIgG1, to block the binding of huBAFF to BJAB cells.

Materials and Methods

The huBAFF-R (2-71)-huIgG1 fusion discussed in example 9 was generated and called pJST618. This construct was transiently transfected into 293EBNA cells and the conditioned media was harvested. The fusion protein was purified by acid elution from proteinA Sepharose followed by and gel filtration chromatography. Biotinylated myc-huBAFF, 200 ng/ml, was preincubated with either 50 ul FACS buffer or with five fold serial dilutions, ranging from 5 μg/ml to 200 ng/ml, of purified huBAFF-R:Fc for 30 minutes on ice. BJAB cells (2.5×10$^5$ cells) were then incubated with these solutions on ice for one hour. Cells were washed with FACS buffer and stained with SAV-PE. The cells were analyzed by FACS for PE fluorescence and the data was formatted as overlayed histograms. Alternatively, 200 ng/ml biotinylated-BAFF was pre-incubated with two-fold serial dilutions of either hBAFF-R:Fc, hTACI:Fc, or hLTBR:Fc. Cells were stained for biotinylated BAFF binding as above.

Results

FIG. 13A shows the overlay of the histograms plotted for huBAFF binding to BJAB in the presence of various concentrations of huBAFF-R:Fc. The black line labelled "A" represents background binding of SAV-PE and the red line marked "E" represents cells stained with biotinylated myc-huBAFF without pre-incubation with BAFF-R:Fc. Pre-incubation of biotinylated myc-huBAFF with 5 μg/ml of huBAFF-R:Fc results in a shift in the histogram nearly to background levels (curve B). Pre-incubation with either 1 μg/ml (curve C) or 200 ng/ml (curve D) huBAFF-R-huIgG1 resulted in an approximate four-fold decrease in biotinylated myc-huBAFF binding.

FIG. 13B shows that both BAFF-R:Fc and TACI:Fc are able to block BAFF binding to BJAB cells. Pre-incubation with LTBR:Fc has no BAFF blocking effect.

Example 14

This example describes the ability of a BAFF-R:IgG1 fusion protein to block BAFF-induced B cell proliferation.

Material and Methods

For the in vitro proliferation assay, mouse B cells were isolated from spleens of C57Bl6 mice (8 weeks old) using a B cell recovery column (column (Cellect™ Mouse B Cell Recovery Column: Cedarlane Laboratories Limited, Ontario, Canada.). Purified B cells were analyzed by FACS and >90% were found positive for B220 staining. B cells were incubated in 96-well plates (10$^5$ cells/well in 50 ml RPMI supplemented with 10% FBS) for 72 hours in the presence or absence of 2 mg/ml of goat anti-human m chain antibody (Sigma Chemical Co.); control hIgG (10 mg/ml) huBAFF-R:Fc (10 mg/ml). The samples were done plated in triplicate and with the indicated concentrations of myc-hBAFF. Cells were pulsed for an additional 18 hours with [$^3$H]thymidine (1 μCi/well) and harvested. [$^3$H]Thymidine incorporation was monitored by liquid scintillation counting. Human BAFF-R:Fc fusion protein, produced as in example 13, was used in this assay., as discussed in example 9, was generated from the supernatant of pJST618 transfected 293EBNA cells. The supernatant was harvested, loaded onto a Protein A column, eluted with acid, neutralized and then subjected to gel filtration chromatography in order to obtain aggregate-free huBAFF-R:Fc protein. The BAFF used in the assay was expressed in *Pichia pastoris* and purified by anion exchange chromatography followed by gel filtration.

Results

Figure 14:
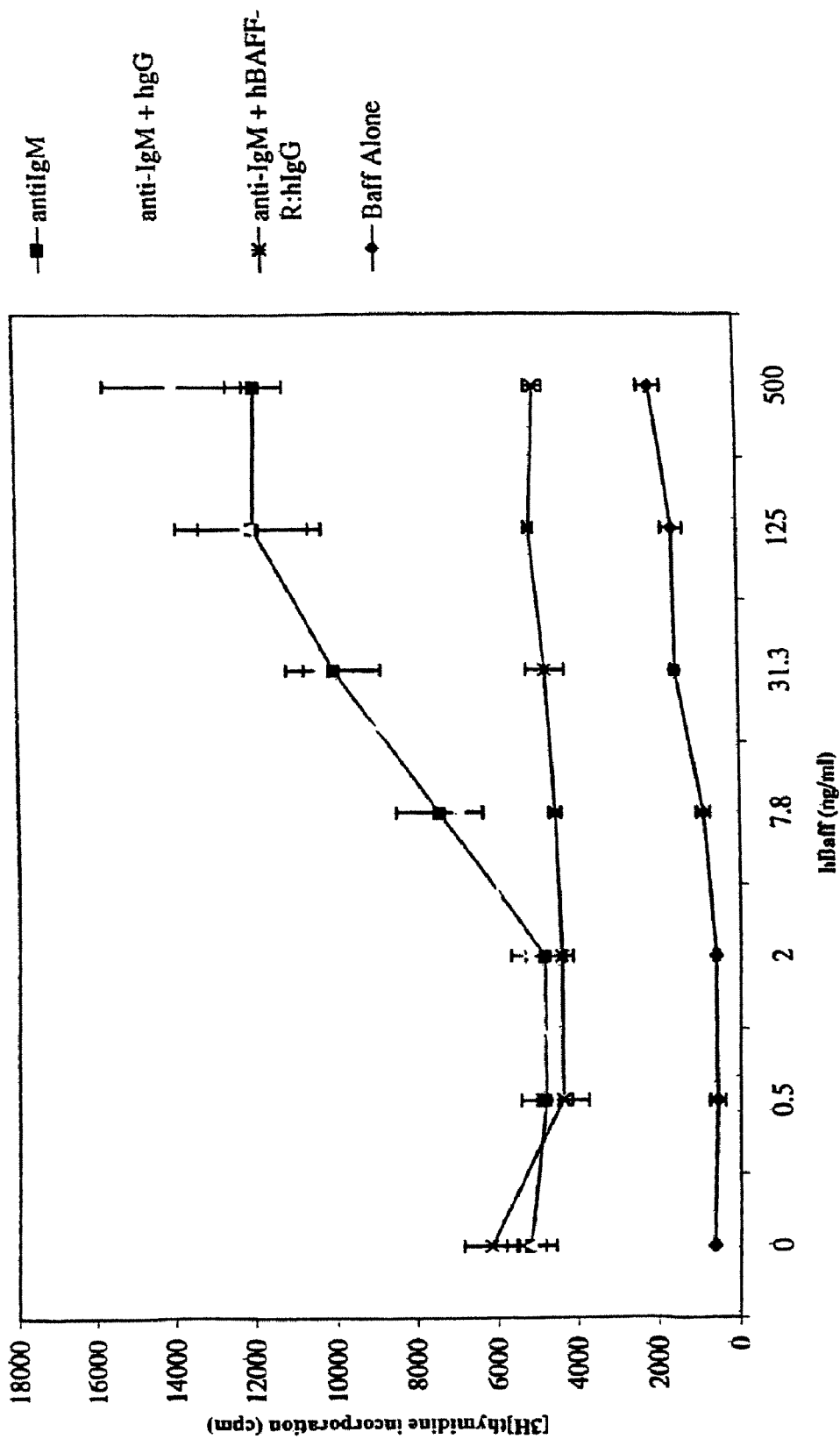
FIG. 14 shows the ability of BAFF-R:Fc to block BAFF-induced co-stimulation of splenic B cells. A graph of [$^3$H] thymidine incorporation (cpm) versus increasing amounts of hBAFF (ng/ml) is shown.

FIG. 14 shows that BAFF can costimulate B cell growth in the presence of anti-m antibodies (squares) and hIgG (triangles). BAFF alone (diamonds) is not able to induce B cell proliferation. Incubation with 10 mg/ml of huBAFF-R:Fc (stars) results in a complete inhibition of BAFF-induced B cell proliferation.

Materials and Methods

Mice

Six-week old female BALB/c mice were obtained from The Jackson Laboratory (Bar Harbor, Me.) and maintained under barrier conditions in the Biogen Animal Facility.

Reagents and Treatment Regimen

Receptor fusion proteins contain the human IgG1 Fc region. Mice (5/group) received 200 μg of fusion proteins (mouse BAFF-R-Fc or human BAFF-R:Fc ) 2×/week for 4 weeks, ip (intraperitoneally). Control mice received polyclonal human IgG (Panglobulin™) (HIgG), 200 μg 2×/week for 4 weeks. Three days after the last dose, blood was collected via the orbital sinus, then mice were euthanized and spleens, lymph nodes, and bone marrow were collected for analysis.

Flow Cytometric Analysis

At the time of sacrifice spleen weights were recorded. Single cell suspensions were prepared from spleen and blood after lysing red blood cells in a hypotonic solution. Single cell suspensions were also prepared from inguinal lymph nodes and bone marrow. Flow cytometry was performed using mAbs directed against B220, IgM, IgD and CD21. Splenic B cell subpopulations were defined as follicular (B220+, $IgM^{low}$, $CD21^{low}$), marginal zone (B220+, $IgM^{hi}CD21^{hi}$) and newly formed (B220+, $IgM^{hi}CD21-$). Briefly, ~$1.5 \times 10^6$ cells were incubated with 10 µg/ml of Fc Block (Pharmingen) for 10 min on ice to block Fc receptors, followed by addition of fluorescently tagged mAbs and incubated on ice for 30 min Cells were washed 1x and resuspended in 0.5% paraformaldehyde. Cell fluorescence data were acquired on a FACSCalibur flow cytometer (Becton Dickinson, San Jose, Calif.) and analyzed using CellQuest software (Becton Dickinson).

Results

Figure 15:
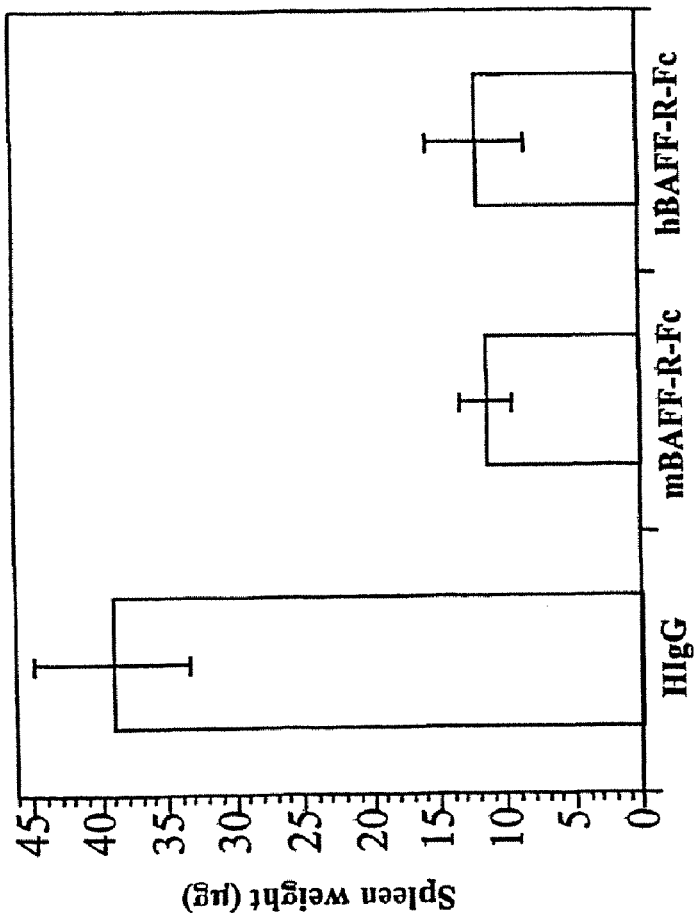
FIG. 15 shows that BAFF-R:Fc1 treatment results in a loss of peripheral B cells in normal mice.
Figure 16:
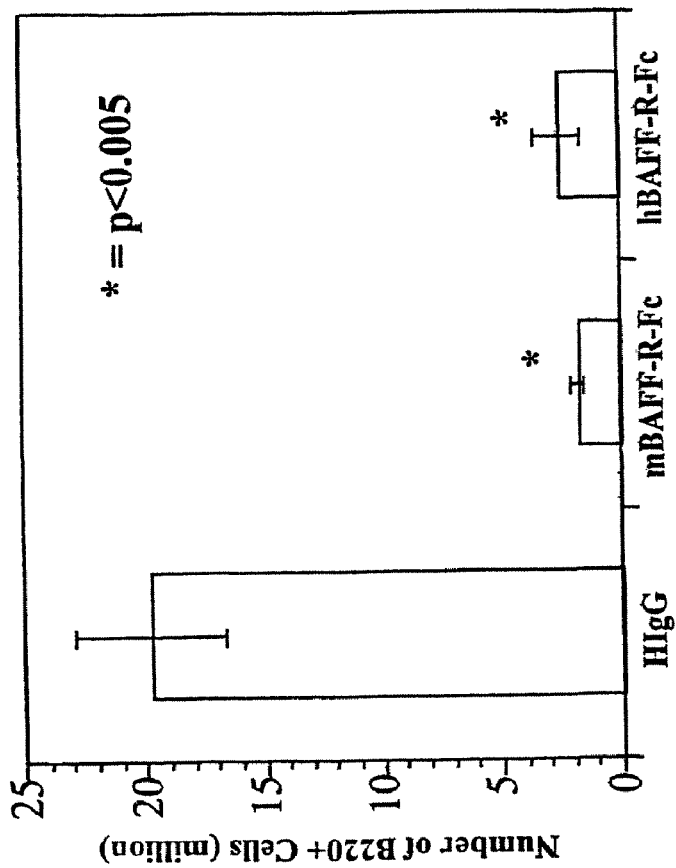
FIG. 16 shows that treatment of mice with human and mouse BAFF-R:Fc reduces the number of splenic B220+ B cells.

After a 4-week treatment course with mouse or human BAFF-R:Fc there was a marked reduction in the weight of spleens from mice treated with mouse and human BAFF-R:Fc (FIG. 15), as compared to control Human IgG-treated mice. The apparent decline in splenic cellularity was found to result from a reduction in the number of splenic B cells. The mean number of total B220+ splenic B cells in mouse and human BAFF-R:Fc-treated mice, $1.8 \times 10^6$ and $2.6 \times 10^6$ cells, respectively, was significantly reduced when compared to the number of B cells in control HIgG-treated animals, which had a mean of $19.8 \times 10^6$ cells (FIG. 16). Examination of different subpopulations of splenic B cells, follicular, marginal zone and newly formed, indicated that the number of B cells in each subset was reduced in the BAFF-R::Fc-treated mice (Table 2), although follicular and marginal zone B cells had the greatest reduction.

TABLE 2

BAFF-R::Fc Treatment Results in a Reduction in Splenic B Cell Subpopulations

| | Splenic B cell subpopulations ($10^6$ cells ± SD) | | |
|---|---|---|---|
| | Follicular | Marginal Zone | Newly formed |
| Human IgG | 14.5 ± 2.4 | 1.1 ± 0.3 | 1.5 ± 0.2 |
| mBAFF-R:Fc | 0.7 ± 0.1 | 0.06 ± 0.02 | 0.4 ± 0.1 |
| hBAFF-R:Fc | 1.4 ± 0.5 | 0.05 ± 0.02 | 0.5 ± 0.2 |

Mice received 200 µg of HIgG, mBAFF-R:Fc or hBAFF-R:Fc on days 1, 4, 8, 11, 15, 18, 22 and 25.
Mice were euthanized on day 28 and spleens were harvested for analysis of B cell subsets.

Figure 17:
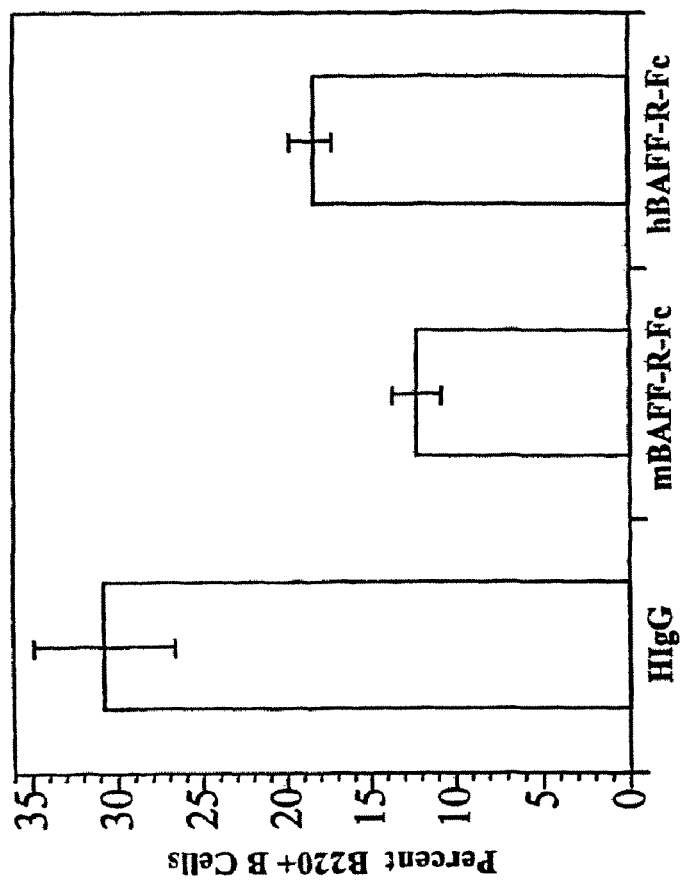
FIG. 17 shows that administration of BAFF-R:Fc to mice reduces the percentage of lymph node B220+ B cells.
Figure 18:
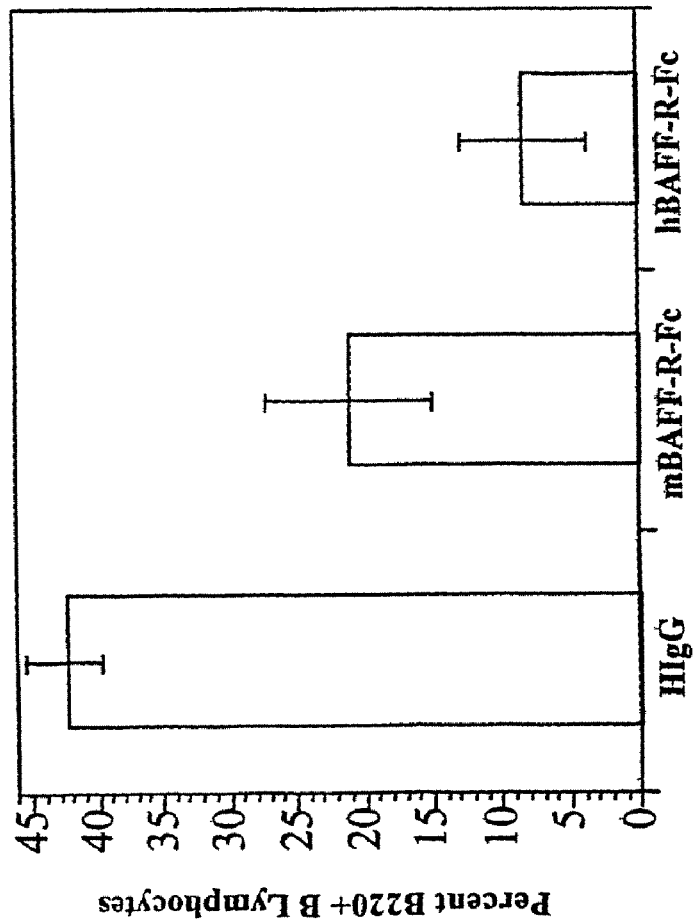
FIG. 18 shows that administration of BAFF-R:Fc to mice reduces peripheral blood B220+ B cells.

Examination of the percent of B220+B cells contained in inguinal lymph nodes (LN) showed that the mean B cell populations were markedly reduced in mouse and human BAFF-R::Fc-treated mice, 12.3% ±1.4 and 18.6% ±1.3, respectively, when compared to control HIgG-treated mice which had a mean of 30.8% ±4.1 B cells (FIG. 17). Similar results were obtained when peripheral blood B cells were examined. 42.5% ±2.9 of the lymphocytes from human IgG-treated mice were B cells, whereas only 21.2% ±6.1 and 8.3% ±4:5 of lymphocytes were B cells from mouse and human BAFF-R::Fc-treated mice, respectively (FIG. 18).

Although newly formed (immature) B cell and mature B cell populations were reduced in BAFF-R::Fc-treated mice, B cell precursors in the bone marrow remained unaffected (data not shown).

Discussion

These results suggest that in vivo blockade of BAFF with a soluble BAFF-R receptor fusion protein leads to the inhibition of B cell survival and/or maturation.

These results also suggest the potential use of a BAFF-R fusion protein as a therapeutic drug with clinical applications in B cell-mediated diseases. Diseases would include those that are autoimmune in nature such as systemic lupus erythematosus, myasthenia gravis, autoimmune hemolytic anemia, idiopathic thrombocytopenia purpura, anti-phospholipid syndrome, Chagas' disease, Grave's disease, Wegener's granulomatosis, poly-arteritis nodosa and rapidly progressive glomerulonephritis. This therapeutic agent would also have application in plasma cell disorders such as multiple myeloma, Waldenstrom's macroglobulinemia, heavy-chain disease, primary or imnunocyte-associated amyloidosis, and monoclonal gammopathy of undetermined significance (MGUS). Oncology targets would include B cell carcinomas, leukemias, and lymphomas.

Example 16

In this example, the characterization of an initial panel of mouse monoclonal antibodies raised against the extracellular domain of BAFF-R is described. All antibodies recognize the extracellular domain of BAFF-R, and a subset of these antibodies have antagonist properties in that they prevent subsequent binding of BAFF to BAFF-R.

Materials and Methods:

RBF mice were immunized and boosted with huBAFF-R:Fc. Splenocytes from the immune mouse were fused with mouse myeloma strain FL653, a derivative of strain P3-X63-Ag8.653 to generate hybridomas by standard technologies.

Conditioned media from hybridoma clones secreting antibodies against the extracellular domain of huBAFFR were assayed by FACS. FACS binding assays were performed 293EBNA cells co-transfected with plasmids expressing fill length huBAFF-R or muBAFF-R and GFP as in Example 5. Hybridoma conditioned media was diluted 1:10 in FACS buffer and incubated with the transfected cells 30 min on ice. Cells were washed with FACS buffer and binding was revealed by incubation with a 1:100 dilution of anti-mouse IgG (H+L) (Jackson ImmunoResearch) for 30 min on ice. The cells were again washed with FACS buffer and resuspended in 1% paraformaldehyde in FACS buffer. The cells were analyzed by FACS for GFP and PE fluorescence and the data was formatted in a four quadrant dot plot as described in Example 5. BAFF blocking assays were performed by incubating 10 ug/ml proteinA purified anti-BAFF-R mAb or control antibody (MOP C21) with BJAB cells for 30 min on ice. After washing, cells were incubated with 250 ng/ml biotinylatedhuBAFF for 30 min on ice. Cells were again washed and BAFF binding was revealed by incubation with SAV-PE. The cells were analyzed by FACS for PE fluorescence and data was plotted as overlayed histograms.

Results:

The supernatants from ten clones were observed to bind huBAFF-R transfected cells. The dot plots of the FACS data of four of the ten anti-BAFF-R supernatants are shown in FIG. 19A. Transfection efficiency was approximately 50%, with nearly all transfected cells shifting to the upper right quadrant after staining with supernatants. None of these ten supernatants bound to 293EBNA cells transfected with muBAFFR (data not shown). Conditioned media from the clones that were positive for binding to BAFF-R were tested for their ability to block the interaction of BAFF with the BAFF-R expressed on the surface of BJAB cells. BJAB cells express BAFFR on their surface, and express no detectable amounts of BCMA or TACI (Thompson et al. (2001) *Science* August 16). Two of the ten hybridomas, clones 2 and 9, produced mAbs that were able to block the interaction of BAFF-R with BAFF and were deposited with the American Type Culture Collection (ATCC) at 10801 University Boulevard, Manassas, Va. 20110, U.S.A. Clone 2 was deposited with the ATCC on Sep. 6, 2001 as "anti-BAFF-R clone #2.1" (IgG1-kappa isotype) and has been assigned ATCC No. PTA-3689; Clone 9 was deposited with the ATCC on Sep. 6, 2001 as "anti-BAFF-R clone #9.1" (IgG1-kappa isotype) and has been assigned ATCC No. PTA-3688). The overlays of the histograms in FIG. 19B show that preincubation of 10 µg/ml of either mAb clone 2 (curve (b)) or 9 (curve (c)) shifts the BAFF binding curve greater than ten-fold to the left, nearly to the signal of the no BAFF control (curve (a)). The rightmost histogram (curve (d)) indicates the shift when control mAb MOP C21, anti-BAFF-R non-blocking mAbs, or no protein were incubated with the cells prior to BAFF binding.

Example 17

This example describes the construction, sequence and protein characterization of amino acid substitutions in hBAFF-R(2-71)-Fc that result in increased solubility of the recombinantly expressed molecule.

Materials and Methods:

Double stranded oligonucleotide cassettes with cohesive ends were used to introduce substitutions at targeted residues by ligation into the same sites in the hBAFF-R(2-71):IgG1 gene.

Expression plasmids were transfected into 293EBNA cells using Lipofectamine 2000 as in Example 5. Aggregation was determined by running non-reducing SDS-PAGE of 20 hr post-transfection conditioned media, followed by western transfer, and detection with HRP conjugated anti-human IgG (1:100, Jackson ImmunoResearch) and ECL detection as in Example 12.

Immunoprecipitation experiments were performed utilizing 100 µl of 20 hr post-transfection conditioned media in 1 ml of DMEM/10%FBS/0.2%NaA3 with 200 ng flag-hu-BAFF. Samples were rocked for 30 min at 4° C., 30 ul protein A-Sepharose was added per tube and rocking continued for another 30 minutes. Sepharose beads were spun down and washed three times with 1 ml cold PBS. Beads were resuspended in 2×SDS reducing buffer and loaded onto 4-20% acrylamide gels. After western transfer as previously described, the ability to immunoprecipitate flag-BAFF was revealed by incubation of the filters with 1 µg/ml HRP conjugated anti-flag M2 (Sigma) followed by ECL detection.

Results:

While the human BAFF-R:Fc is highly aggregated, the murine BAFF-R:Fc is only slightly (<10%) aggregated. Deletion analysis has shown that the entire C-terminal BAFF-R moiety can be deleted from A71 to V36 (last Cys of Cysteine Rich Domain (CRD) is C35) with no decrease in aggregate formation. This would implicate the N-terminal and CRD regions of hBAFFR as being required for aggregate formation.

Figure 20:
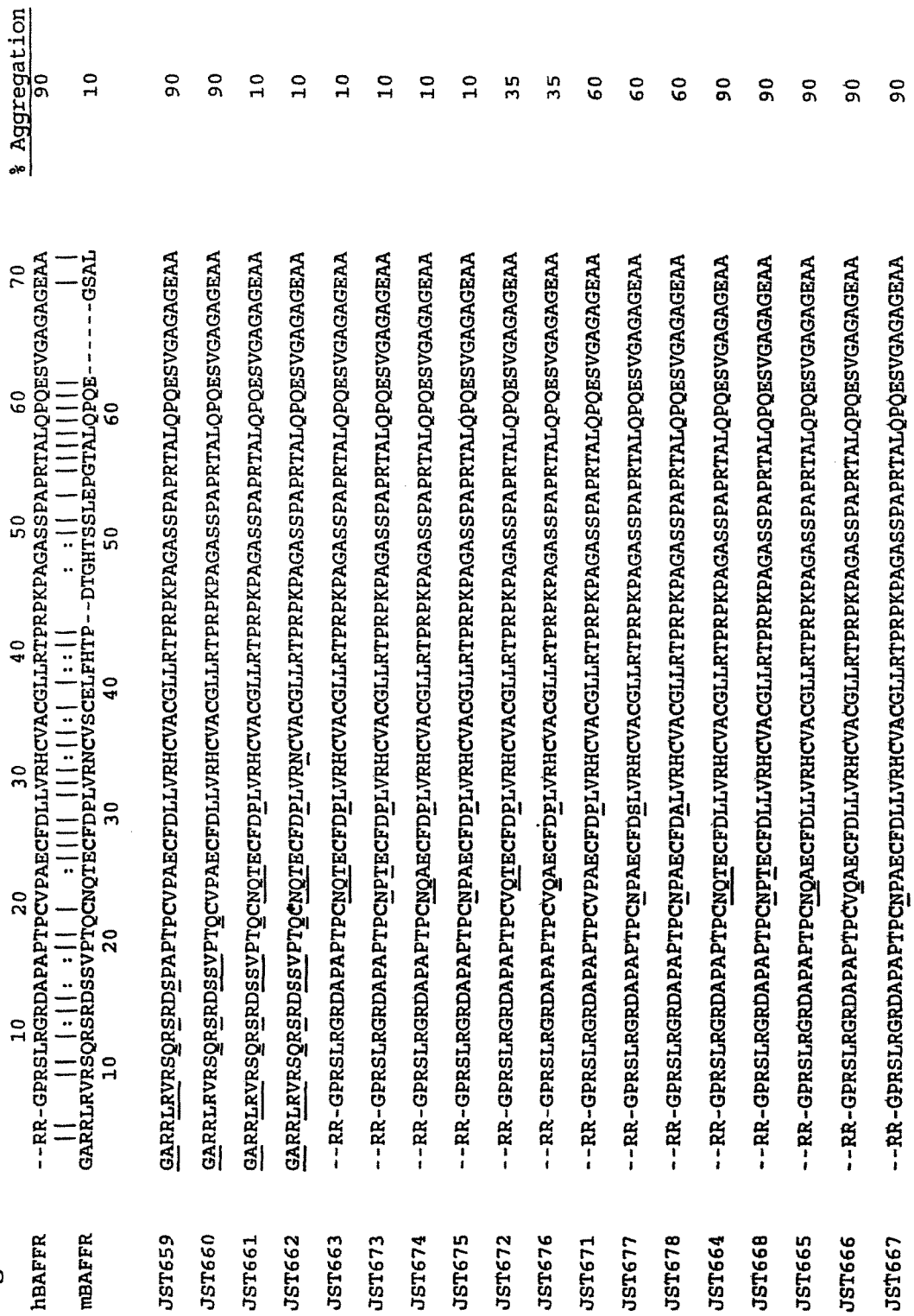
FIG. 20 shows an alignment of the amino acid sequences of human BAFF-R:Fc (hBAFF-R) and mouse BAFF-R:Fc (mBAFF-R) extracellular domains and the percentage of aggregation observed upon expression of the Fc fusion proteins containing the indicated sequences. Numbered JST clones represent the amino acid sequences showing mutations (shown in underline) in the parent sequences and the resulting aggregation of expressed protein. Shown are the partial sequences for human (amino acids 2-71 of SEQ ID NO:10; SEQ ID NO:13) and mouse (amino acids 2-71 of SEQ ID NO:9; SEQ ID NO:14) BAFF-R; and the corresponding portions for the following clones: JST659 (SEQ ID NO:15), JST660 (SEQ ID NO:16, JST661 (SEQ ID NO:17), JST662 (SEQ ID NO:18), JST663 (SEQ ID NO:19), JST673 (SEQ ID NO:20), JST674 (SEQ ID NO:21), JST675 (SEQ ID NO:22), JST672 (SEQ ID NO:23), JST676 (SEQ ID NO: 24), JST671 (SEQ ID NO:25), JST677 (SEQ ID NO:26), JST678 (SEQ ID NO:27), JST664 (SEQ ID NO:28), JST668 (SEQ ID NO:29), JST665 (SEQ ID NO:30), JST666 (SEQ ID NO: 31), and JST667 (SEQ ID NO:32).

Initially, several murine-human BAFF-R:Fc chimeras were generated in which various amounts of N-terminal human BAFF-R sequence were replaced with the homologous murine sequence and analyzed for the effect on protein aggregation. The amino acid sequence for these and subsequent substitutions into hBAFF-R:Fc are shown in FIG. 20. This figure shows the BAFF-R moiety of both the "wild type" human (FIG. 9) and murine BAFF-R:Fc, with the numbering corresponding to the amino acid residues from the full length human (FIG. 2d) (SEQ ID NO:5) or murine BAFF-R (FIG. 4b) (SEQ ID NO:9). FIG. 20 also shows the hBAFFR-R:Fc clones with substitutions, with the substituted residues indicated in bolded, red, underlined type. The chimeras containing less than the first 21 murine residues (Q21) before switching over to human appear to aggregate similar to wild type hBAFF-R:Fc; however, those that contain at least the first 39 murine residues aggregate in a markedly reduced manner, similar to mBAFF-R. Of the additional nine residues different between these two chimeric BAFF-R:Fc constructs, four of them differ between mouse and human. This would implicate at least one of the human residues between C19 and L27, a region internal to the CRD, as being required for aggregation.

Constructs replacing the human residues with those corresponding to murine at only these 4 sites or a subset thereof were made by standard techniques. When only the 4 residues V20N P21 Q A22T L27P were substituted into the human BAFFR moiety, this modified BAFF-R:Fc was not aggregated. hBAFF-R(V20N P21Q A22T L27P):Fc were still able to interact with BAFF as analyzed by-immunoprecipitation. The V20N L27P substitution also reduced aggregation of hBAFF-R:Fc from approximately 90% to about 10%. Intermediate levels of aggregation were observed with P21 Q L27P (40%), L27P (60%), V20N L27A (60%) and V20N L27S (60%). None of the following substitutions diminished protein aggregation: V20N P21 Q A22T; V20N A22T; V20N P21 Q; V20N; and P21 Q.

Example 18

This example describes p21-Arc is a protein associated with BAFF-R. The method used to determine such an interaction was immunoprecipitation.

Methods

A construct containing the cDNA encodes the intracellular domain of BAFF-R (BAFF-R-i.c.d.) with a myc tagged fused at the N-terminus was made and subcloned into CH269 plasmid at NheI (5') and XhoI (3') sites. The 293E cells were tranasfected with this construct and were lysed 72 hours after with lysis buffer containing in 150 mM NaCl, 50 mM Tris-HCl, pH7.5, 1 mM Na3VO4, 50 mM NaF and 1% Brij 97. The cell lysates were cleared with a table top centrifuge at 10,000 g for 5 minutes and were immunoprecipitated with an anti-myc monoclonal antibody, 9E10. The immunoprecipitates were separated by a 10-20% SDS-PAGE under reducing conditions and were trans-blotted onto a PVDF membrane. The blotted proteins were visualized with 0.2% Ponceau S solution and the areas corresponding to proteins specifically associated with BAFF-R were excised and subjected to N-terminal amino acid sequence analysis. An ambiguous search in the non-redundant protein database using the PATTERN SEARCH algorithm was performed for the obtained N-terminal sequence data.

Results

One of the proteins specifically associated with the myc-tagged BAFFR cytoplasmic domain has an apparent molecular weight of 21 kDa. This protein was unambiguously identified as the p21-Arc (Actin related protein complex). P21-Arc is a component of a seven subunits protein called Arp2/3 complex which was shown to be involved in the actin polymerization (Welch et al. (1997) *J. Cell Biol.* 138:357). Recently, an actin-binding protein, filamin, was reported to be associated with the tumor necrosis factor receptor-associated factor 2 (TRAF2) (Leonardi et al. (2000) *J. Biol. Chem.* 275:271). Thus, the identification of p21-Arc in the co-immunoprecipitates of BAFFR cytoplasmic domain suggests p21-Arc is either directly associated the BAFFR or indirectly associated with BAFFR via its association with TRAF2 and/or other TRAF protein which, in turn, associates with the BAFFR.

From the foregoing detailed description of the specific embodiments of the invention, it should be apparent that unique have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. An isolated antibody, or an antigen binding portion thereof, that specifically binds to an amino acid sequence selected from the group consisting of SEQ ID NO:5 and SEQ ID NO:10.

2. The antibody or antigen binding portion thereof according to claim 1, wherein the antibody specifically binds to the amino acid sequence of SEQ ID NO:10.

3. The antibody or antigen binding portion thereof according to claim 2, wherein the antibody specifically binds to the amino acid sequence of SEQ ID NO:13.

4. The antibody or antigen binding portion thereof according to claim 1, wherein the antibody is chimeric.

5. The antibody or antigen binding portion thereof according to claim 1, wherein the antibody is humanized.

6. The antibody or antigen binding portion thereof according to claim 1, wherein the antibody is monoclonal.

7. The antibody or antigen binding portion thereof according to claim 1, wherein the antibody is polyclonal.

8. The antibody or antigen binding portion thereof according to claim 1, wherein the antibody is a single chain antibody.

9. The antibody or antigen binding portion thereof according to claim 1, wherein the antibody is a Fab fragment.

10. The antibody or antigen binding portion thereof according to claim 1, wherein the antibody is a F(ab')2 fragment.

11. The antibody or antigen binding portion thereof according to claim 1, wherein the antibody blocks binding of B Cell Activating Factor of the TNF family (BAFF) to its receptor.

12. The antibody or antigen binding portion thereof according to claim 1, wherein the antibody is produced by hybridoma clone #2.1, deposited under ATCC No. PTA-3689 or binds to the same epitope as the antibody produced by hybridoma clone #2.1.

13. The antibody according to claim 12, wherein the antibody is chimeric or an antigen binding portion of the chimeric antibody.

14. The antibody according to claim 13, wherein the chimeric antibody is humanized, or an antigen binding portion of the humanized antibody.

15. The antibody or antigen binding portion thereof according to claim 1, wherein the antibody is produced by hybridoma clone #9.1 deposited under ATCC No. PTA-3688 or binds to the same epitope as the antibody produced by hybridoma clone #9.1.

16. The antibody according to claim 15, wherein the antibody is chimeric, or an antigen binding portion of the chimeric antibody.

17. The antibody according to claim 16, wherein the chimeric antibody is humanized, or an antigen binding portion of the humanized antibody.

18. A pharmaceutical composition comprising the antibody according any one of claims 1, 11, 13, 14, 16, and 17, or an antigen binding portion thereof, and a pharmaceutically acceptable carrier.

19. A method of inhibiting BAFF activity in a mammal comprising administering the pharmaceutical composition of claim 18 to the mammal.

20. The method of claim 19, wherein the mammal is human.

21. A method of treating a mammal
  for a B-cell-mediated disease or condition selected from the group consisting of an autoimmune condition, a tumorigenic condition, carcinoma, leukemia, lymphoma, organ transplantation, and Burkett's lymphoma comprising administering an effective amount of the composition of claim 18.

22. The method of claim 21, wherein the lymphoma is Burkitt's lymphoma.

23. The method of claim 21, wherein the B-cell-mediated condition is carcinoma, leukemia, or lymphoma.

24. The method of claim 21, wherein the autoimmune condition is systemic lupus erythematosus.

25. The method of claim 21, wherein the autoimmune condition is rheumatoid arthritis.

26. A kit comprising the antibody or antigen binding portion thereof according to claim 1 in a container and instructions for use.

27. An isolated cell that produces the antibody or antigen binding portion thereof according to any one of claims 1 and 11-17.

28. The cell of claim 27, wherein the cell is a hybridoma.

29. The cell of claim 28, wherein the hybridoma is clone #2.1, deposited under ATCC No. PTA-3689, or clone #9.1, deposited under ATCC No. PTA-3688.

30. A method of making an antibody or an antigen binding portion thereof, comprising culturing the cell of claim 27 and recovering the antibody or antigen binding portion thereof.

31. The antibody or antigen binding portion thereof produced by the method of claim 30.

32. A method of detecting a BAFF-R polypeptide, said method comprising:
  (a) providing a biological sample; and
  (b) contacting the sample with the antibody or antigen binding portion thereof according to claim 1,
  wherein the presence of an antibody-antigen complex indicates the presence of BAFF-R polypeptide in the biological sample.

33. The method of claim 32, wherein the antibody is chimeric.

34. The method of claim 32, wherein the antibody is humanized.

35. The method of claim 32, wherein the antibody is a single-chain antibody.

36. The method of claim 32, wherein the antibody is a Fab fragment.

37. The method of claim 32, wherein the antibody is produced by hybridoma clone #2.1, deposited under ATCC No. PTA-3689 or binds to the same epitope as the antibody produced by hybridoma clone #2.1.

38. The method of claim 32, wherein the antibody is produced by hybridoma clone #9.1, deposited under ATCC No. PTA-3688 or binds to the same epitope as the antibody produced by hybridoma clone #9.1.

39. The method of claim 32, wherein the biological sample is obtained from a mammal.

40. The method of claim 39, wherein the mammal is human.

41. The method of claim 39, wherein the mammal has a B-cell-mediated condition selected from the group consisting of: an autoimmune condition, a tumorigenic condition, a B-cell carcinoma, leukemia, lymphoma, organ transplantation, and Burkitt's lymphoma.

42. The method of claim 41, wherein the B-cell mediated condition is B cell carcinoma, leukemia, or lymphoma.

43. The method of claim 41, wherein the autoimmune condition is systemic lupus erythematosus.

44. The method of claim 41, wherein the autoimmune condition is rheumatoid arthritis.

* * * * *

UNITED STATES PATENT AND TRADEMARK OFFICE
CERTIFICATE OF CORRECTION

PATENT NO. : 7,638,327 B2  Page 1 of 1
APPLICATION NO. : 11/426236
DATED : December 22, 2009
INVENTOR(S) : Christine M. Ambrose and Jeffrey S. Thompson It is certified that error appears in the above-identified patent and that said Letters Patent is hereby corrected as shown below:

In claim 18, column 107, line 32, "according any" should read --according to any--.

Signed and Sealed this

Twenty-third Day of February, 2010

David J. Kappos
*Director of the United States Patent and Trademark Office*

UNITED STATES PATENT AND TRADEMARK OFFICE
CERTIFICATE OF CORRECTION

PATENT NO.        : 7,638,327 B2                              Page 1 of 1
APPLICATION NO. : 11/426236
DATED             : December 29, 2009
INVENTOR(S)       : Ambrose et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 490 days.

Signed and Sealed this

Ninth Day of November, 2010

David J. Kappos
*Director of the United States Patent and Trademark Office*

SEQUENCE LISTING

```
<160> NUMBER OF SEQ ID NOS: 37

<210> SEQ ID NO 1
<211> LENGTH: 1201
<212> TYPE: DNA
<213> ORGANISM: Homo sapiens

<400> SEQUENCE: 1
gcaccatgag gcgagggccc cggagcctgc ggggcaggga cgcgccagcc cccacgccct      60
gcgtcccggc cgagtgcttc gacctgctgg tccgccactg cgtggcctgc gggctcctgc     120
gcacgccgcg gccgaaaccg ggtaaggggg acccacgggg cgcgcggcgc cggcagctgc     180
ggggagaacg gggcccccgat cgccagggcg caggcagagc cccgaccccc ggggcgccg     240 agggctgaaa ggaccctgtg ggcagggcct ggaggggccc gcgatcaccg cgtggccctc     300
accgccgcct ctctccctcc ccttgtccac cgccccccgg ctgtccctcc cctccccggc     360
cagcctcgcc cccctccgcc cctccccgtc cccgctcctc cctcccctcg gcccctggc     420 ctccctccct gtccctccc gaagcagccg gggcagcag ccctgcgccc aggacggcgc     480
tgcagccgca ggagtcggtg ggcgcggggg ccggcgaggc ggcgctgccc ctgcccgggc     540
tgctctttgg cgccccccgcg ctgctgggcc tggcactggt cctggcgctg gtcctggtgg     600
gtctggtgag ctggaggcgg cgacagcggc ggcttcgcgg cgcgtcctcc gcagaggccc     660
ccgacggaga caaggacgcc ccagagcccc tggacaaggt catcattctg tctccgggaa     720
tctctgatgc cacagctcct gcctggcctc ctcctgggga agacccagga accacccac      780 ctggccacag tgtccctgtg ccagccacag agctgggctc cactgaactg gtgaccacca     840
agacggccgg ccctgagcaa caatagcagg gagccggcag gaggtggccc ctgccctccc     900
tctggacccc cagccagggg cttggaaatc aaattcagct cttcactcca gcatgcacat     960
gccctctttc tgggaccagg ctaaccctgc agaagcacag acactacaga ccacagcatt    1020
cagcccccat ggagtttggt gtgcttgcct ttggcttcag acctcaccat ctttgacagc    1080
ccttgaaggt ggtagcccag ctcctgttcc tgtgccttca aaaggctggg gcactatgag    1140
taaaagaccg cttttaaaat ggggaaggca ccattaagcc aaaatgaatc tgaaaaaaga    1200
c                                                                   1201

<210> SEQ ID NO 2
<211> LENGTH: 992
<212> TYPE: DNA
<213> ORGANISM: Homo sapiens

<400> SEQUENCE: 2
```

```
gtcgacccac gcgtccgccc acgcgtccgg tgcggcggcg tcggcaccat gaggcgaggg      60
ccccggagcc tgcggggcag ggacgcgcca gcccccacgc cctgcgtccc ggccgagtgc     120
ttcgacctgc tggtccgcca ctgcgtggcc tgcgggctcc tgcgcacgcc gcggccgaaa     180
ccgggtaagg gggacccacg gggcgcgcgg cgccggcagc tgcggggaga acggggcccc     240
gatcgccagg gcgcaggcag agccccgacc ccgggggcg ccgagggctg aaaggaccct     300
gtgggcaggg cctggagggg cccgcgatca ccgcgtggcc ctcaccgccg cctctctccc     360
tccccttgtc caccgccccc cggctgtccc tcccctcccc ggccagcctc gcccccctcc     420
gcccctcccc gtcccgctc ctccctcccc tcggcccct ggcctcctc cctgtccct      480 cccgaagcag ccggggccag cagccctgcg cccaggacgg cgctgcagcc gcaggagtcg     540
gtgggcgcgg gggccggcga ggcggcgctg cccctgcccg ggctgctctt tggcgccccc     600
gcgctgctgg gcctggcact ggtcctggcg ctggtcctgg tgggtctggt gagctggagg     660
cggcgacagc ggcggcttcg cggcgcgtcc tccgcagagg cccccgacgg agacaaggac     720
gccccagagc ccctggacaa ggtcatcatt ctgtctccgg gaatctctga tgccacagct     780
cctgcctggc ctcctcctgg ggaagaccca ggaaccaccc cacctggcca cagtgtccct     840
gtgccagcca cagagctggg ctccactgaa ctggtgacca ccaagacggc cggccctgag     900
caacaatagc agggagccgg caggaggtgg cccctgccct ccctctggac ccccagccag     960
gggcttggaa atcaaattca gctcttcact cc                                  992

<210> SEQ ID NO 3
<211> LENGTH: 906
<212> TYPE: DNA
<213> ORGANISM: Homo sapiens

<400> SEQUENCE: 3
ggcgcgccgc accatgaggc gagggccccg gagcctgcgg ggcagggacg cgccagcccc      60
cacgccctgc gtccggccg agtgcttcga cctgctggtc cgccactgcg tggcctgcgg     120
gctcctgcgc acgccgcggc cgaaaccggc agcgggggcc agcagccctg cgcccaggac     180
ggcgctgcag ccgcaggagt cggtgggcgc ggggccggc gaggcggcgc tgcccctgcc     240
cgggctgctc tttggcgccc ccgcgctgct gggcctggca ctggtcctgg cgctggtcct     300
ggtgggtctg gtgagctgga ggcggcgaca gcggcggctt cgcggcgcgt cctccgcaga     360 ggccccgac ggagacaagg acgccccaga gccctggac aaggtcatca ttctgtctcc     420
gggaatctct gatgccacag ctcctgcctg gcctcctcct ggggaagacc caggaaccac     480
cccacctggc cacagtgtcc ctgtgccagc cacagagctg gctccactg aactggtgac     540 caccaagacg gccggccctg agcaacaata gcagggagcc ggcaggaggt ggcccctgcc     600
ctccctctgg accccagcc aggggcttgg aaatcaaatt cagctcttca ctccagcatg     660
cacatgccct ctttctggga ccaggctaac cctgcagaag cacagacact acagaccaca     720
gcattcagcc cccatggagt ttggtgtgct tgcctttggc ttcagacctc accatctttg     780
acagcccttg aaggtggtag cccagctcct gttcctgtgc cttcaaaagg ctggggcact     840
atgagtaaaa gaccgctttt aaaatgggga aggcaccatt aagccaaaat gaatctgaaa     900
aaagac                                                               906

<210> SEQ ID NO 4
<211> LENGTH: 903
<212> TYPE: DNA
<213> ORGANISM: Homo sapiens
```

<400> SEQUENCE: 4

```
ggcgcgccgc accatgaggc gagggccccg gagcctgcgg ggcagggacg cgccagcccc      60
cacgccctgc gtcccggccg agtgcttcga cctgctggtc cgccactgcg tggcctgcgg     120
gctcctgcgc acgccgcggc cgaaaccggc cggggccagc agccctgcgc ccaggacggc     180
gctgcagccg caggagtcgg tgggcgcggg ggccggcgag gcggcgctgc ccctgccccg     240
gctgctcttt ggcgccccccg cgctgctggg cctggcactg gtcctggcgc tggtcctggt    300
gggtctggtg agctggaggc ggcgacagcg cggcttcgc ggcgcgtcct ccgcagaggc      360
ccccgacgga gacaaggacg ccccagagcc cctggacaag gtcatcattc tgtctccggg    420
aatctctgat gccacagctc ctgcctggcc tcctcctggg gaagacccag gaaccacccc    480
acctggccac agtgtccctg tgccagccac agagctgggc tccactgaac tggtgaccac    540
caagacggcc ggccctgagc aacaatagca gggagccggc aggaggtggc ccctgccctc    600
cctctggacc cccagccagg ggcttggaaa tcaaattcag ctcttcactc cagcatgcac    660
atgccctctt tctgggacca ggctaaccct gcagaagcac agacactaca gaccacagca    720
ttcagccccc atggagtttg tgtgcttgc ctttggcttc agacctcacc atctttgaca    780
gcccttgaag gtggtagccc agctcctgtt cctgtgcctt caaaaggctg gggcactatg    840
agtaaaagac cgcttttaaa atggggaagg caccattaag ccaaaatgaa tctgaaaaaa    900
gac                                                                    903
```

<210> SEQ ID NO 5
<211> LENGTH: 185
<212> TYPE: PRT
<213> ORGANISM: Homo sapiens

<400> SEQUENCE: 5

```
Met Arg Arg Gly Pro Arg Ser Leu Arg Gly Arg Asp Ala Pro Ala Pro
  1               5                  10                  15

Thr Pro Cys Val Pro Ala Glu Cys Phe Asp Leu Leu Val Arg His Cys
             20                  25                  30

Val Ala Cys Gly Leu Leu Arg Thr Pro Arg Pro Lys Pro Ala Ala Gly
         35                  40                  45

Ala Ser Ser Pro Ala Pro Arg Thr Ala Leu Gln Pro Gln Glu Ser Val
     50                  55                  60

Gly Ala Gly Ala Gly Glu Ala Ala Leu Pro Leu Pro Gly Leu Leu Phe
 65                  70                  75                  80

Gly Ala Pro Ala Leu Leu Gly Leu Ala Leu Val Leu Ala Leu Val Leu
                 85                  90                  95

Val Gly Leu Val Ser Trp Arg Arg Arg Gln Arg Arg Leu Arg Gly Ala
            100                 105                 110

Ser Ser Ala Glu Ala Pro Asp Gly Asp Lys Asp Ala Pro Glu Pro Leu
        115                 120                 125

Asp Lys Val Ile Ile Leu Ser Pro Gly Ile Ser Asp Ala Thr Ala Pro
    130                 135                 140

Ala Trp Pro Pro Pro Gly Glu Asp Pro Gly Thr Thr Pro Pro Gly His
145                 150                 155                 160

Ser Val Pro Val Pro Ala Thr Glu Leu Gly Ser Thr Glu Leu Val Thr
                165                 170                 175

Thr Lys Thr Ala Gly Pro Glu Gln Gln
            180                 185
```

<210> SEQ ID NO 6
<211> LENGTH: 1187
<212> TYPE: DNA
<213> ORGANISM: Homo sapiens

<400> SEQUENCE: 6

```
gggcgcctac aatctcagct actcgggagg ctgaggcaga gaattgtttg aacccgggag        60
gcagagcttg cagtgagccg agatagcgcc attgcactcc agcctgggcg acagagcgag       120
actccgtctc aaaaaaaaaa aagaaaaga aagggggggcc ccaggcgagc tcggtcccac       180
ccagcaggcg ggggcggggc agggcagagt gctcccccccg ccccccgctt cctcccccgag      240
ggccccggag cccagctcag cctcagtccc cgcagcttgt gcggcggcgt cggcaccatg       300
aggcgagggc cccggagcct gcggggcagg gacgcgccag ccccacgcc ctgcgtcccg        360
gccgagtgct tcgacctgct ggtccgccac tgcgtggcct gcgggctcct gcgcacgccg       420
cggccgaaac cggccgggc cagcagccct gcgcccagga cggcgctgca gccgcaggag       480
tcggtgggcg cgggggccgg cgaggcggcg ctgcccctgc ccgggctgct ctttggcgcc       540
cccgcgctgc tgggcctggc actggtcctg gcgctggtcc tggtgggtct ggtgagctgg       600
aggcggcgac agcggcggct tcgcggcgcg tcctccgcag aggccccccga cggagacaag      660
gacgccccag agccctggga caaggtcatc attctgtctc cgggaatctc tgatgccaca       720
gctcctgcct ggcctcctcc tggggaagac ccaggaacca cccccacctgg ccacagtgtc      780
cctgtgccag ccacagagct gggctccact gaactggtga ccaccaagac ggccggccct      840
gagcaacaat agcagggagc cggcaggagg tggcccctgc cctccctctg gaccccagc       900
caggggcttg gaaatcaaat tcagctcttc actccagcat gcacatgccc tctttctggg       960
accaggctaa ccctgcagaa gcacagacac tacagaccac agcattcagc ccccatggag      1020
tttggtgtgc ttgcctttgg cttcagacct caccatcttt gacagccctt gaaggtggta     1080
gcccagctcc tgttcctgtg ccttcaaaag gctggggcac tatgagtaaa agaccgcttt     1140
taaaatgggg aaggcaccat taagccaaaa tgaatctgaa aaaagac                    1187
```

<210> SEQ ID NO 7
<211> LENGTH: 266
<212> TYPE: PRT
<213> ORGANISM: Homo sapiens

<400> SEQUENCE: 7

```
Thr Arg Glu Ala Glu Leu Ala Val Ser Arg Asp Ser Ala Ile Ala Leu
1               5                   10                  15

Gln Pro Gly Arg Gln Ser Glu Thr Pro Ser Gln Lys Lys Lys Lys
            20                  25                  30

Arg Lys Gly Gly Pro Arg Arg Ala Arg Ser His Pro Ala Gly Gly Gly
        35                  40                  45

Gly Ala Gly Gln Ser Ala Pro Pro Ala Pro Arg Phe Leu Pro Glu Gly
    50                  55                  60

Pro Gly Ala Gln Leu Ser Leu Ser Pro Arg Ser Leu Cys Gly Val
65                  70                  75                  80

Gly Thr Met Arg Arg Gly Pro Arg Ser Leu Arg Gly Arg Asp Ala Pro
                85                  90                  95

Ala Pro Thr Pro Cys Val Pro Ala Glu Cys Phe Asp Leu Leu Val Arg
            100                 105                 110

His Cys Val Ala Cys Gly Leu Leu Arg Thr Pro Arg Pro Lys Pro Ala
        115                 120                 125
```

```
Gly Ala Ser Ser Pro Ala Pro Arg Thr Ala Leu Gln Pro Gln Glu Ser
        130                 135                 140
Val Gly Ala Gly Ala Gly Glu Ala Ala Leu Pro Leu Pro Gly Leu Leu
145                 150                 155                 160
Phe Gly Ala Pro Ala Leu Leu Gly Leu Ala Leu Val Leu Ala Leu Val
                165                 170                 175
Leu Val Gly Leu Val Ser Trp Arg Arg Gln Arg Arg Leu Arg Gly
        180                 185                 190
Ala Ser Ser Ala Glu Ala Pro Asp Gly Asp Lys Asp Ala Pro Glu Pro
        195                 200                 205
Leu Asp Lys Val Ile Ile Leu Ser Pro Gly Ile Ser Asp Ala Thr Ala
        210                 215                 220
Pro Ala Trp Pro Pro Gly Glu Asp Pro Thr Thr Pro Pro Gly
225                 230                 235                 240
His Ser Val Pro Val Pro Ala Thr Glu Leu Gly Ser Thr Glu Leu Val
                245                 250                 255
Thr Thr Lys Thr Ala Gly Pro Glu Gln Gln
        260                 265

<210> SEQ ID NO 8
<211> LENGTH: 1943
<212> TYPE: DNA
<213> ORGANISM: Mus musculus

<400> SEQUENCE: 8
gaattcggca cgagcccaga ctcggaactg tcccagctgc atgaggcggc gacatgggcg      60
ccaggagact ccgggtccga agccagagga gccgggacag ctcggtgccc acccagtgca     120
atcagaccga gtgcttcgac cctctggtga aaactgcgt gtcctgtgag ctcttccaca     180
cgccggacac tggacataca agcagcctgg agcctgggac agctctgcag cctcaggagg     240
gctccgcgct gagacccgac gtggcgctgc tcgtcggtgc cccgcactc ctgggactga     300
tactggcgct gaccctggtg gtctagtga gtctggtgag ctggaggtgg cgtcaacagc     360
tcaggacggc ctccccagac acttcagaag gagtccagca agagtccctg gaaaatgtct     420
ttgtaccctc ctcagaaacc cctcatgcct cagctcctac ctggcctccg ctcaaagaag     480
atgcagacag cgccctgcca cgccacagcg tcccggtgcc cgccacagaa ctgggctcca     540
ccgagctggt gaccaccaag acagctggcc cagagcaata gcagcagtgg aggctggaac     600
ccagggatct ctactgggct tgtggacttc acccaacagc ttgggaaaga acttggccct     660
tcagtgacgg agtcctttgc ctgggggggcg aaccggcag aaccagacac tacaggccac     720
atgagattgc ttttgtgtta gctcttgact tgagaacgtt ccatttctga gatggttttt     780
aagcctgtgt gccttcagat ggttggatag acttgagggt tgcatattta atctctgtag     840
tgagtcggag actggaaact taatctcgtt ctaaaaattt tggattactg ggctggaggt     900
atggctcagc agttcggttt gtgtgctgtt ctagccgagg actccagttg ttcagcttcc     960
cggaactcag atctggcagc ttaagaccac ctgtcactcc agcccctgga acatccttgc    1020
ctccaaaggc accagcactc atttgctcta gagcacacac acacacacac acacacacac    1080
acacacacac acacacacat atgcatgcat gcacacttaa aaatgtcaaa attagcggct    1140
ggagaaattc atggtcaaca gcgcttactg tgattccaga ggatgagagt ttgattccca    1200
gaatgcactg cggtggctc attactgagc ataactttg cttcagggga cctgatgcct    1260
ctggacttca tgggcatctg tattcacgtg cacatcctac acacacacac acacacacac    1320
```

-continued

```
acagacatac acacacacac actcttttac aaatgataaa atataagata ggcatggtgg    1380
tacacacctt taatcccaac attggggaag caaaggcagg caggtaactg agttggaggc    1440
catcctggtc tacatagcaa gttccaggct aaccagagct aaatggtgag accaagtctc    1500
aaaataatac tcccccccca aaaaaaaaaa acttttaaat tttgatttt ttcttttatt     1560 attattttt atattaattt catggtgttt agaagtggta tacttagatg gtgactaaga     1620
ggaggtaaag ccatcaggac tgagccccta acatacaagg agaaagcaga gacaatgaac    1680
acgcccctct cctgctgtgt gccagctctg gaccaccagc cagagggcaa tcatcagatg    1740
tgggccctag aaccttcaga gccgaaagct aaatcaatct catttctttg taaagctatt    1800
tagccttagg tgttttgtta cggtgatata aatggacta acacaggcac tatgagtaag     1860
aagctttcct ttgagctggg aaaggtactg ttaaaccaaa attaatctga ataaaaaaag    1920
gctaagggga agacacttaa aaa                                            1943
```

```
<210> SEQ ID NO 9
<211> LENGTH: 175
<212> TYPE: PRT
<213> ORGANISM: Mus musculus

<400> SEQUENCE: 9

Met Gly Ala Arg Arg Leu Arg Val Arg Ser Gln Arg Ser Arg Asp Ser
1               5                   10                  15

Ser Val Pro Thr Gln Cys Asn Gln Thr Glu Cys Phe Asp Pro Leu Val
            20                  25                  30

Arg Asn Cys Val Ser Cys Glu Leu Phe His Thr Pro Asp Thr Gly His
        35                  40                  45

Thr Ser Ser Leu Glu Pro Gly Thr Ala Leu Gln Pro Gln Glu Gly Ser
    50                  55                  60

Ala Leu Arg Pro Asp Val Ala Leu Leu Gly Ala Pro Ala Leu Leu
65                  70                  75                  80

Gly Leu Ile Leu Ala Leu Thr Leu Val Gly Leu Val Ser Leu Val Ser
                85                  90                  95

Trp Arg Trp Arg Gln Gln Leu Arg Thr Ala Ser Pro Asp Thr Ser Glu
            100                 105                 110

Gly Val Gln Gln Glu Ser Leu Glu Asn Val Phe Val Pro Ser Ser Glu
        115                 120                 125

Thr Pro His Ala Ser Ala Pro Thr Trp Pro Pro Leu Lys Glu Asp Ala
    130                 135                 140

Asp Ser Ala Leu Pro Arg His Ser Val Pro Val Pro Ala Thr Glu Leu
145                 150                 155                 160

Gly Ser Thr Glu Leu Val Thr Thr Lys Thr Ala Gly Pro Glu Gln
                165                 170                 175
```

```
<210> SEQ ID NO 10
<211> LENGTH: 184
<212> TYPE: PRT
<213> ORGANISM: Homo sapiens

<400> SEQUENCE: 10

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
```

```
                35                  40                  45
Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
 65                  70                  75                  80

Ala Pro Ala Leu Leu Gly Leu Ala Leu Val Leu Ala Leu Val Leu Val
                 85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180
```

<210> SEQ ID NO 11
<211> LENGTH: 963
<212> TYPE: DNA
<213> ORGANISM: Homo sapiens
<220> FEATURE:
<221> NAME/KEY: sig_peptide
<222> LOCATION: (1)..(63)
<223> OTHER INFORMATION: encodes signal peptide
<220> FEATURE:
<221> NAME/KEY: misc_feature
<222> LOCATION: (64)..(66)
<223> OTHER INFORMATION: introduces restriction site
<220> FEATURE:
<221> NAME/KEY: misc_feature
<222> LOCATION: (67)..(276)
<223> OTHER INFORMATION: encodes BAFF-R extracellular region
<220> FEATURE:
<221> NAME/KEY: misc_feature
<222> LOCATION: (277)..(279)
<223> OTHER INFORMATION: introduces restriction site
<220> FEATURE:
<221> NAME/KEY: misc_feature
<222> LOCATION: (280)..(960)
<223> OTHER INFORMATION: encodes human IgG1 Fc

<400> SEQUENCE: 11
atggagacag acacactcct gttatgggtg ctgctgctct gggttccagg ttccactggt    60
gacgtcaggc gagggccccg gagcctgcgg ggcaggacg cgccagcccc cacgccctgc   120
gtcccggccg agtgcttcga cctgctggtc cgccactgcg tggcctgcgg gctcctgcgc   180
acgccgcggc cgaaaccggc cggggccagc agccctgcgc caggacggc gctgcagccg   240 caggagtcgg tgggcgcggg ggccggcgag gcggcggtcg acaaaactca cacatgccca   300
ccgtgcccag cacctgaact cctgggggga ccgtcagtct tcctcttccc cccaaaaccc   360
aaggacaccc tcatgatctc ccggacccct gaggtcacat gcgtggtggt ggacgtgagc   420
cacgaagacc ctgaggtcaa gttcaactgg tacgtgacg gcgtggaggt gcataatgcc   480
aagacaaagc cgcgggagga gcagtacaac agcacgtacc gtgtggtcag cgtcctcacc   540
gtcctgcacc aggactggct gaatggcaag gagtacaagt gcaaggtctc caacaaagcc   600
ctcccagccc ccatcgagaa aaccatctcc aaagccaaag ggcagcccg agaaccacag   660

```
gtgtacaccc tgcccccatc ccgggatgag ctgaccaaga accaggtcag cctgacctgc    720
ctggtcaaag gcttctatcc cagcgacatc gccgtggagt gggagagcaa tgggcagccg    780
gagaacaact acaagaccac gcctcccgtg ttggactccg acggctcctt cttcctctac    840
agcaagctca ccgtggacaa gagcaggtgg cagcagggga acgtcttctc atgctccgtg    900
atgcatgagg ctctgcacaa ccactacacg cagaagagcc tctccctgtc tcccgggaaa    960
tga                                                                  963

<210> SEQ ID NO 12
<211> LENGTH: 320
<212> TYPE: PRT
<213> ORGANISM: Homo sapiens
<220> FEATURE:
<221> NAME/KEY: SIGNAL
<222> LOCATION: (1)..(21)
<223> OTHER INFORMATION: signal sequence
<220> FEATURE:
<221> NAME/KEY: MISC_FEATURE
<222> LOCATION: (22)..(22)
<223> OTHER INFORMATION: encoded by region introducing restriction site
<220> FEATURE:
<221> NAME/KEY: PEPTIDE
<222> LOCATION: (23)..(92)
<223> OTHER INFORMATION: BAFF-R extracellular domain
<220> FEATURE:
<221> NAME/KEY: MISC_FEATURE
<222> LOCATION: (93)..(93)
<223> OTHER INFORMATION: encoded by region introducing restriction site
<220> FEATURE:
<221> NAME/KEY: PEPTIDE
<222> LOCATION: (94)..(320)
<223> OTHER INFORMATION: Human IgG1 Fc

<400> SEQUENCE: 12

Met Glu Thr Asp Thr Leu Leu Leu Trp Val Leu Leu Leu Trp Val Pro
1               5                   10                  15

Gly Ser Thr Gly Asp Val Arg Arg Gly Pro Arg Ser Leu Arg Gly Arg
            20                  25                  30

Asp Ala Pro Ala Pro Thr Pro Cys Val Pro Ala Glu Cys Phe Asp Leu
        35                  40                  45

Leu Val Arg His Cys Val Ala Cys Gly Leu Leu Arg Thr Pro Arg Pro
    50                  55                  60

Lys Pro Ala Gly Ala Ser Ser Pro Ala Pro Arg Thr Ala Leu Gln Pro
65                  70                  75                  80

Gln Glu Ser Val Gly Ala Gly Ala Gly Glu Ala Ala Val Asp Lys Thr
                85                  90                  95

His Thr Cys Pro Pro Cys Pro Ala Pro Glu Leu Leu Gly Gly Pro Ser
            100                 105                 110

Val Phe Leu Phe Pro Pro Lys Pro Lys Asp Thr Leu Met Ile Ser Arg
        115                 120                 125

Thr Pro Glu Val Thr Cys Val Val Val Asp Val Ser His Glu Asp Pro
    130                 135                 140

Glu Val Lys Phe Asn Trp Tyr Val Asp Gly Val Glu Val His Asn Ala
145                 150                 155                 160

Lys Thr Lys Pro Arg Glu Glu Gln Tyr Asn Ser Thr Tyr Arg Val Val
                165                 170                 175

Ser Val Leu Thr Val Leu His Gln Asp Trp Leu Asn Gly Lys Glu Tyr
            180                 185                 190

Lys Cys Lys Val Ser Asn Lys Ala Leu Pro Ala Pro Ile Glu Lys Thr
        195                 200                 205
```

```
Ile Ser Lys Ala Lys Gly Gln Pro Arg Glu Pro Gln Val Tyr Thr Leu
    210                 215                 220

Pro Pro Ser Arg Asp Glu Leu Thr Lys Asn Gln Val Ser Leu Thr Cys
225                 230                 235                 240

Leu Val Lys Gly Phe Tyr Pro Ser Asp Ile Ala Val Glu Trp Glu Ser
                245                 250                 255

Asn Gly Gln Pro Glu Asn Asn Tyr Lys Thr Thr Pro Pro Val Leu Asp
                260                 265                 270

Ser Asp Gly Ser Phe Phe Leu Tyr Ser Lys Leu Thr Val Asp Lys Ser
                275                 280                 285

Arg Trp Gln Gln Gly Asn Val Phe Ser Cys Ser Val Met His Glu Ala
    290                 295                 300

Leu His Asn His Tyr Thr Gln Lys Ser Leu Ser Leu Ser Pro Gly Lys
305                 310                 315                 320

<210> SEQ ID NO 13
<211> LENGTH: 70
<212> TYPE: PRT
<213> ORGANISM: Homo sapiens

<400> SEQUENCE: 13

Arg Arg Gly Pro Arg Ser Leu Arg Gly Arg Asp Ala Pro Ala Pro Thr
1               5                   10                  15

Pro Cys Val Pro Ala Glu Cys Phe Asp Leu Leu Val Arg His Cys Val
                20                  25                  30

Ala Cys Gly Leu Leu Arg Thr Pro Arg Pro Lys Pro Ala Gly Ala Ser
            35                  40                  45

Ser Pro Ala Pro Arg Thr Ala Leu Gln Pro Gln Glu Ser Val Gly Ala
        50                  55                  60

Gly Ala Gly Glu Ala Ala
65                  70

<210> SEQ ID NO 14
<211> LENGTH: 65
<212> TYPE: PRT
<213> ORGANISM: Mus musculus

<400> SEQUENCE: 14

Gly Ala Arg Arg Leu Arg Val Arg Ser Gln Arg Ser Arg Asp Ser Ser
1               5                   10                  15

Val Pro Thr Gln Cys Asn Gln Thr Glu Cys Phe Asp Pro Leu Val Arg
                20                  25                  30

Asn Cys Val Ser Cys Glu Leu Phe His Thr Pro Asp Thr Gly His Thr
            35                  40                  45

Ser Ser Leu Glu Pro Gly Thr Ala Leu Gln Pro Gln Glu Gly Ser Ala
        50                  55                  60

Leu
65

<210> SEQ ID NO 15
<211> LENGTH: 73
<212> TYPE: PRT
<213> ORGANISM: Homo sapiens
<220> FEATURE:
<221> NAME/KEY: VARIANT
<222> LOCATION: (1)..(1)
<223> OTHER INFORMATION: substitution
<220> FEATURE:
<221> NAME/KEY: VARIANT
<222> LOCATION: (2)..(2)
```

<223> OTHER INFORMATION: substitution
<220> FEATURE:
<221> NAME/KEY: VARIANT
<222> LOCATION: (5)..(5)
<223> OTHER INFORMATION: substitution
<220> FEATURE:
<221> NAME/KEY: VARIANT
<222> LOCATION: (6)..(6)
<223> OTHER INFORMATION: substitution
<220> FEATURE:
<221> NAME/KEY: VARIANT
<222> LOCATION: (7)..(7)
<223> OTHER INFORMATION: substitution
<220> FEATURE:
<221> NAME/KEY: VARIANT
<222> LOCATION: (10)..(10)
<223> OTHER INFORMATION: substitution
<220> FEATURE:
<221> NAME/KEY: VARIANT
<222> LOCATION: (12)..(12)
<223> OTHER INFORMATION: substitution
<220> FEATURE:
<221> NAME/KEY: VARIANT
<222> LOCATION: (15)..(15)
<223> OTHER INFORMATION: substitution

<400> SEQUENCE: 15

Gly Ala Arg Arg Leu Arg Val Arg Ser Gln Arg Ser Arg Asp Ser Pro
1               5                   10                  15

Ala Pro Thr Pro Cys Val Pro Ala Glu Cys Phe Asp Leu Leu Val Arg
            20                  25                  30

His Cys Val Ala Cys Gly Leu Leu Arg Thr Pro Arg Pro Lys Pro Ala
        35                  40                  45

Gly Ala Ser Ser Pro Ala Pro Arg Thr Ala Leu Gln Pro Gln Glu Ser
    50                  55                  60

Val Gly Ala Gly Ala Gly Glu Ala Ala
65                  70

<210> SEQ ID NO 16
<211> LENGTH: 73
<212> TYPE: PRT
<213> ORGANISM: Homo sapiens
<220> FEATURE:
<221> NAME/KEY: VARIANT
<222> LOCATION: (1)..(1)
<223> OTHER INFORMATION: substitution
<220> FEATURE:
<221> NAME/KEY: VARIANT
<222> LOCATION: (2)..(2)
<223> OTHER INFORMATION: substitution
<220> FEATURE:
<221> NAME/KEY: VARIANT
<222> LOCATION: (10)..(10)
<223> OTHER INFORMATION: substitution
<220> FEATURE:
<221> NAME/KEY: VARIANT
<222> LOCATION: (12)..(12)
<223> OTHER INFORMATION: substitution
<220> FEATURE:
<221> NAME/KEY: VARIANT
<222> LOCATION: (15)..(15)
<223> OTHER INFORMATION: substitution
<220> FEATURE:
<221> NAME/KEY: VARIANT
<222> LOCATION: (16)..(16)
<223> OTHER INFORMATION: substitution
<220> FEATURE:
<221> NAME/KEY: VARIANT
<222> LOCATION: (17)..(17)
<223> OTHER INFORMATION: substitution
<220> FEATURE:
<221> NAME/KEY: VARIANT
<222> LOCATION: (20)..(20)

-continued

```
<223> OTHER INFORMATION: substitution

<400> SEQUENCE: 16

Gly Ala Arg Arg Leu Arg Val Arg Ser Gln Arg Ser Arg Asp Ser Ser
1               5                   10                  15

Val Pro Thr Gln Cys Val Pro Ala Glu Cys Phe Asp Leu Leu Val Arg
                20                  25                  30

His Cys Val Ala Cys Gly Leu Leu Arg Thr Pro Arg Pro Lys Pro Ala
                35                  40                  45

Gly Ala Ser Ser Pro Ala Pro Arg Thr Ala Leu Gln Pro Gln Glu Ser
            50                  55                  60

Val Gly Ala Gly Ala Gly Glu Ala Ala
65                  70

<210> SEQ ID NO 17
<211> LENGTH: 73
<212> TYPE: PRT
<213> ORGANISM: Homo sapiens
<220> FEATURE:
<221> NAME/KEY: VARIANT
<222> LOCATION: (1)..(1)
<223> OTHER INFORMATION: substitution
<220> FEATURE:
<221> NAME/KEY: VARIANT
<222> LOCATION: (2)..(2)
<223> OTHER INFORMATION: substitution
<220> FEATURE:
<221> NAME/KEY: VARIANT
<222> LOCATION: (5)..(5)
<223> OTHER INFORMATION: substitution
<220> FEATURE:
<221> NAME/KEY: VARIANT
<222> LOCATION: (6)..(6)
<223> OTHER INFORMATION: substitution
<220> FEATURE:
<221> NAME/KEY: VARIANT
<222> LOCATION: (7)..(7)
<223> OTHER INFORMATION: substitution
<220> FEATURE:
<221> NAME/KEY: VARIANT
<222> LOCATION: (10)..(10)
<223> OTHER INFORMATION: substitution
<220> FEATURE:
<221> NAME/KEY: VARIANT
<222> LOCATION: (12)..(12)
<223> OTHER INFORMATION: substitution
<220> FEATURE:
<221> NAME/KEY: VARIANT
<222> LOCATION: (15)..(15)
<223> OTHER INFORMATION: substitution
<220> FEATURE:
<221> NAME/KEY: VARIANT
<222> LOCATION: (16)..(16)
<223> OTHER INFORMATION: substitution
<220> FEATURE:
<221> NAME/KEY: VARIANT
<222> LOCATION: (17)..(17)
<223> OTHER INFORMATION: substitution
<220> FEATURE:
<221> NAME/KEY: VARIANT
<222> LOCATION: (20)..(20)
<223> OTHER INFORMATION: substitution
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (23)..(23)
<223> OTHER INFORMATION: substitution
<220> FEATURE:
<221> NAME/KEY: VARIANT
<222> LOCATION: (24)..(24)
```

-continued

```
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 17
```

Gly Ala Arg Arg Leu Arg Val Arg Ser Gln Arg Ser Arg Asp Ser Ser
1               5                   10                  15

Val Pro Thr Gln Cys Asn Gln Thr Glu Cys Phe Asp Pro Leu Val Arg
                20                  25                  30

His Cys Val Ala Cys Gly Leu Leu Arg Thr Pro Arg Pro Lys Pro Ala
            35                  40                  45

Gly Ala Ser Ser Pro Ala Pro Arg Thr Ala Leu Gln Pro Gln Glu Ser
    50                  55                  60

Val Gly Ala Gly Ala Gly Glu Ala Ala
65                  70

```
<210> SEQ ID NO 18
<211> LENGTH: 73
<212> TYPE: PRT
<213> ORGANISM: Homo sapiens
<220> FEATURE:
<221> NAME/KEY: VARIANT
<222> LOCATION: (1)..(1)
<223> OTHER INFORMATION: substitution
<220> FEATURE:
<221> NAME/KEY: VARIANT
<222> LOCATION: (2)..(2)
<223> OTHER INFORMATION: substitution
<220> FEATURE:
<221> NAME/KEY: VARIANT
<222> LOCATION: (5)..(5)
<223> OTHER INFORMATION: substitution
<220> FEATURE:
<221> NAME/KEY: VARIANT
<222> LOCATION: (6)..(6)
<223> OTHER INFORMATION: substitution
<220> FEATURE:
<221> NAME/KEY: VARIANT
<222> LOCATION: (7)..(7)
<223> OTHER INFORMATION: substitution
<220> FEATURE:
<221> NAME/KEY: VARIANT
<222> LOCATION: (10)..(10)
<223> OTHER INFORMATION: substitution
<220> FEATURE:
<221> NAME/KEY: VARIANT
<222> LOCATION: (12)..(12)
<223> OTHER INFORMATION: substitution
<220> FEATURE:
<221> NAME/KEY: VARIANT
<222> LOCATION: (15)..(15)
<223> OTHER INFORMATION: substitution
<220> FEATURE:
<221> NAME/KEY: VARIANT
<222> LOCATION: (16)..(16)
<223> OTHER INFORMATION: substitution
<220> FEATURE:
<221> NAME/KEY: VARIANT
<222> LOCATION: (17)..(17)
<223> OTHER INFORMATION: substitution
<220> FEATURE:
<221> NAME/KEY: VARIANT
<222> LOCATION: (20)..(20)
<223> OTHER INFORMATION: substitution
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (23)..(23)
```

```
<223> OTHER INFORMATION: substitution
<220> FEATURE:
<221> NAME/KEY: VARIANT
<222> LOCATION: (24)..(24)
<223> OTHER INFORMATION: substitution
<220> FEATURE:
<221> NAME/KEY: VARIANT
<222> LOCATION: (29)..(29)
<223> OTHER INFORMATION: substitution
<220> FEATURE:
<221> NAME/KEY: VARIANT
<222> LOCATION: (33)..(33)
<223> OTHER INFORMATION: substitution

<400> SEQUENCE: 18

Gly Ala Arg Arg Leu Arg Val Arg Ser Gln Arg Ser Arg Asp Ser Ser
1               5                   10                  15

Val Pro Thr Gln Cys Asn Gln Thr Glu Cys Phe Asp Pro Leu Val Arg
            20                  25                  30

Asn Cys Val Ala Cys Gly Leu Leu Arg Thr Pro Arg Pro Lys Pro Ala
        35                  40                  45

Gly Ala Ser Ser Pro Ala Pro Arg Thr Ala Leu Gln Pro Gln Glu Ser
    50                  55                  60

Val Gly Ala Gly Ala Gly Glu Ala Ala
65                  70

<210> SEQ ID NO 19
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (23)..(23)
<223> OTHER INFORMATION: substitution
<220> FEATURE:
<221> NAME/KEY: VARIANT
<222> LOCATION: (24)..(24)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 19

Arg Arg Gly Pro Arg Ser Leu Arg Gly Arg Asp Ala Pro Ala Pro Thr
1               5                   10                  15

Pro Cys Asn Gln Thr Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 20
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
```

```
<220> FEATURE:
<221> NAME/KEY: VARIANT
<222> LOCATION: (24)..(24)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 20

Arg Arg Gly Pro Arg Ser Leu Arg Gly Arg Asp Ala Pro Ala Pro Thr
1               5                   10                  15

Pro Cys Asn Pro Thr Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 21
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (23)..(23)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 21

Arg Arg Gly Pro Arg Ser Leu Arg Gly Arg Asp Ala Pro Ala Pro Thr
1               5                   10                  15

Pro Cys Asn Gln Ala Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 22
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 22

Arg Arg Gly Pro Arg Ser Leu Arg Gly Arg Asp Ala Pro Ala Pro Thr
1               5                   10                  15
```

```
Pro Cys Asn Pro Ala Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 23
<211> LENGTH: 70
<212> TYPE: PRT
<213> ORGANISM: Homo sapiens
<220> FEATURE:
<221> NAME/KEY: VARIANT
<222> LOCATION: (23)..(23)
<223> OTHER INFORMATION: substitution
<220> FEATURE:
<221> NAME/KEY: VARIANT
<222> LOCATION: (24)..(24)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 23

Arg Arg Gly Pro Arg Ser Leu Arg Gly Arg Asp Ala Pro Ala Pro Thr
1               5                   10                  15

Pro Cys Val Gln Thr Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 24
<211> LENGTH: 70
<212> TYPE: PRT
<213> ORGANISM: Homo sapiens
<220> FEATURE:
<221> NAME/KEY: VARIANT
<222> LOCATION: (23)..(23)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 24

Arg Arg Gly Pro Arg Ser Leu Arg Gly Arg Asp Ala Pro Ala Pro Thr
1               5                   10                  15

Pro Cys Val Gln Ala Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70
```

```
<210> SEQ ID NO 25
<211> LENGTH: 70
<212> TYPE: PRT
<213> ORGANISM: Homo sapiens
<220> FEATURE:
<221> NAME/KEY: VARIANT
<222> LOCATION: (29)..(29)
<223> OTHER INFORMATION: substitution

<400> SEQUENCE: 25

Arg Arg Gly Pro Arg Ser Leu Arg Gly Arg Asp Ala Pro Ala Pro Thr
1               5                   10                  15

Pro Cys Val Pro Ala Glu Cys Phe Asp Pro Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 26
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 26

Arg Arg Gly Pro Arg Ser Leu Arg Gly Arg Asp Ala Pro Ala Pro Thr
1               5                   10                  15

Pro Cys Asn Pro Ala Glu Cys Phe Asp Ser Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

<210> SEQ ID NO 27
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (29)..(29)
<223> OTHER INFORMATION: substitution

<400> SEQUENCE: 27

Arg Arg Gly Pro Arg Ser Leu Arg Gly Arg Asp Ala Pro Ala Pro Thr
1               5                   10                  15

Pro Cys Asn Pro Ala Glu Cys Phe Asp Ala Leu Val Arg His Cys Val
            20                  25                  30
```

```
Ala Cys Gly Leu Leu Arg Thr Pro Arg Pro Lys Pro Ala Gly Ala Ser
            35                  40                  45

Ser Pro Ala Pro Arg Thr Ala Leu Gln Pro Gln Glu Ser Val Gly Ala
        50                  55                  60

Gly Ala Gly Glu Ala Ala
65                  70

<210> SEQ ID NO 28
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (23)..(23)
<223> OTHER INFORMATION: substitution
<220> FEATURE:
<221> NAME/KEY: VARIANT
<222> LOCATION: (24)..(24)
<223> OTHER INFORMATION: substitution

<400> SEQUENCE: 28

Arg Arg Gly Pro Arg Ser Leu Arg Gly Arg Asp Ala Pro Ala Pro Thr
1               5                   10                  15

Pro Cys Asn Gln Thr Glu Cys Phe Asp Leu Leu Val Arg His Cys Val
            20                  25                  30

Ala Cys Gly Leu Leu Arg Thr Pro Arg Pro Lys Pro Ala Gly Ala Ser
            35                  40                  45

Ser Pro Ala Pro Arg Thr Ala Leu Gln Pro Gln Glu Ser Val Gly Ala
        50                  55                  60

Gly Ala Gly Glu Ala Ala
65                  70

<210> SEQ ID NO 29
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (24)..(24)
<223> OTHER INFORMATION: substitution

<400> SEQUENCE: 29

Arg Arg Gly Pro Arg Ser Leu Arg Gly Arg Asp Ala Pro Ala Pro Thr
1               5                   10                  15

Pro Cys Asn Pro Thr Glu Cys Phe Asp Leu Leu Val Arg His Cys Val
            20                  25                  30

Ala Cys Gly Leu Leu Arg Thr Pro Arg Pro Lys Pro Ala Gly Ala Ser
            35                  40                  45

Ser Pro Ala Pro Arg Thr Ala Leu Gln Pro Gln Glu Ser Val Gly Ala
        50                  55                  60

Gly Ala Gly Glu Ala Ala
65                  70

<210> SEQ ID NO 30
<211> LENGTH: 70
```

```
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution
<220> FEATURE:
<221> NAME/KEY: VARIANT
<222> LOCATION: (23)..(23)
<223> OTHER INFORMATION: substitution

<400> SEQUENCE: 30
```

Arg Arg Gly Pro Arg Ser Leu Arg Gly Arg Asp Ala Pro Ala Pro Thr
1               5                   10                  15

Pro Cys Asn Gln Ala Glu Cys Phe Asp Leu Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

```
<210> SEQ ID NO 31
<211> LENGTH: 70
<212> TYPE: PRT
<213> ORGANISM: Homo sapiens
<220> FEATURE:
<221> NAME/KEY: VARIANT
<222> LOCATION: (23)..(23)
<223> OTHER INFORMATION: substitution

<400> SEQUENCE: 31
```

Arg Arg Gly Pro Arg Ser Leu Arg Gly Arg Asp Ala Pro Ala Pro Thr
1               5                   10                  15

Pro Cys Val Gln Ala Glu Cys Phe Asp Leu Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

Gly Ala Gly Glu Ala Ala
65                  70

```
<210> SEQ ID NO 32
<211> LENGTH: 70
<212> TYPE: PRT
<213> ORGANISM: Homo sapiens
<220> FEATURE:
<221> NAME/KEY: VARIANT
<222> LOCATION: (22)..(22)
<223> OTHER INFORMATION: substitution

<400> SEQUENCE: 32
```

Arg Arg Gly Pro Arg Ser Leu Arg Gly Arg Asp Ala Pro Ala Pro Thr
1               5                   10                  15

Pro Cys Asn Pro Ala Glu Cys Phe Asp Leu Leu Val Arg His Cys Val
            20                  25                  30

Ala Cys Gly Leu Leu Arg Thr Pro Arg Pro Lys Pro Ala Gly Ala Ser
        35                  40                  45

Ser Pro Ala Pro Arg Thr Ala Leu Gln Pro Gln Glu Ser Val Gly Ala
    50                  55                  60

```
<210> SEQ ID NO 33
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 33
ggccgagtgc ttcgacctgc t                                        21

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 34
ggtccgccac tgcgtggcct g                                        21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 35
caccaagacg gccggccctg a                                        21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 36
gggcgcctac aatctcagct a                                        21

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 37
ggcggaccag caggtcgaag cactc                                    25
```

Gly Ala Gly Glu Ala Ala
65              70